(12) United States Patent
Davé et al.

(10) Patent No.: US 10,751,288 B2
(45) Date of Patent: Aug. 25, 2020

(54) DRY PROCESSED SURFACE COATED ENGINEERING EXCIPIENTS

(71) Applicant: New Jersey Institute of Technology, Newark, NJ (US)

(72) Inventors: Rajesh N. Davé, Princeton, NJ (US); Liang Chen, Newark, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 31 days.

(21) Appl. No.: 15/684,371

(22) Filed: Aug. 23, 2017

(65) Prior Publication Data

US 2018/0055775 A1    Mar. 1, 2018

Related U.S. Application Data

(60) Provisional application No. 62/378,384, filed on Aug. 23, 2016.

(51) Int. Cl.
*A61K 9/28* (2006.01)
*A61K 31/192* (2006.01)
*A61K 9/20* (2006.01)

(52) U.S. Cl.
CPC .......... *A61K 9/2813* (2013.01); *A61K 9/2054* (2013.01); *A61K 9/2095* (2013.01); *A61K 9/28* (2013.01); *A61K 31/192* (2013.01)

(58) Field of Classification Search
CPC .......... A61K 9/14; A61K 9/16; A61K 9/2095; A61K 9/2072; A61K 9/2086; A61K 9/2018; A61K 9/2054
See application file for complete search history.

(56) References Cited

U.S. PATENT DOCUMENTS

| | | |
|---|---|---|
| 6,197,369 B1 | 3/2001 | Watano et al. |
| 6,746,693 B2 | 6/2004 | Staniforth et al. |
| 6,833,185 B2 | 12/2004 | Zhu et al. |
| 6,858,231 B2 | 2/2005 | Sherwood et al. |
| 6,866,867 B2 | 3/2005 | Staniforth et al. |
| 6,936,277 B2 | 8/2005 | Staniforth et al. |
| 8,252,370 B1 | 8/2012 | Young et al. |
| 2007/0053846 A1 | 3/2007 | Dave et al. |
| 2018/0116966 A1* | 5/2018 | Kothari ................ A61K 9/1623 |

OTHER PUBLICATIONS

Zhou et al., Preparation and Characterization of Surface-Engineered Coarse Microcrystalline Cellulose Through Dry Coating with Silica Nanoparticles. Journal of Pharmaceutical Sciences, vol. 101, No. 11, Nov. 2012, p. 4258-4266 (Year: 2012).*

(Continued)

*Primary Examiner* — Lakshmi S Channavajjala
(74) *Attorney, Agent, or Firm* — Lerner, David, Littenberg, Krumholz & Mentlik, LLP

(57) ABSTRACT

Pharmaceutical blends are disclosed herein. In some embodiments, a pharmaceutical blend includes a cohesive active pharmaceutical ingredient (API) and a dry coated pharmaceutical excipient. The dry coated pharmaceutical excipient is present in an amount of about 1 wt % to 99 wt %, based on the total weight of the pharmaceutical blend. The dry coated pharmaceutical excipient includes a core and a shell surrounding the core, wherein the shell partially covers the core of the pharmaceutical excipient.

22 Claims, 73 Drawing Sheets

(56) References Cited

OTHER PUBLICATIONS

CAB-O-SIL M-5 Untreated fumed silica. product sheet 2004 Cabot Corporation, 2 pages. (Year: 2004).*

Hydrophobic fumed silica. AEROSIL. product sheet, 2 pages, Feb. 12, 2019. (Year: 2019).*

Chattoraj et al., "Profoundly improving flow properties of a cohesive cellulose powder by surface coating with nano? silica through comilling", Journal of Pharmaceutical Sciences, vol. 100, No. 11, Nov. 2011, pp. 4943-4952.

Chen et al., "Fluidization of coated group C powders", AICHE Journal, vol. 54, No. 1, Jan. 2008, pp. 104-121.

Fichtner et al., "Effect of Surface Energy on Powder Compactibility", Pharmaceutical Research, vol. 25, No. 12, Dec. 2008, pp. 2750-2759.

Han et al., "Passivation of high-surface-energy sites of milled ibuprofen crystals via dry coating for reduced cohesion and improved flowability", Journal of Pharmaceutical Sciences, vol. 102, No. 7, Jul. 2013, pp. 2282-2296.

Huang et al. "Flow and bulk density enhancements of pharmaceutical powders using a conical screen mill: A continuous dry coating device", Chemical Engineering Science, vol. 125, Mar. 2015, pp. 209-224.

Huang et al., "Improved blend and tablet properties of fine pharmaceutical powders via dry particle coating", International Journal of Pharmaceutics, vol. 478, Issue 2, Jan. 2015, pp. 447-455.

Jallo et al., "Explaining Electrostatic Charging and Flow of Surface-Modified Acetaminophen Powders as a Function of Relative Humidity Through Surface Energetics", Journal of Pharmaceutical Sciences vol. 104, Issue 7, Jul. 2015, pp. 2225-2232.

Jallo et al., Improvement of flow and bulk density of pharmaceutical powders using surface modification, International Journal of Pharmaceutics, vol. 423, Issue 2, Feb. 2012, pp. 213-225.

Pfeffer et al., "Synthesis of engineered particulates with tailored properties using dry particle coating", Powder Technology, vol. 117, Issues 1-2, Jun. 2001, pp. 40-67.

Sun, Decoding Powder Tabletability: Roles of Particle Adhesion and Plasticity, Journal of Adhesion Science and Technology, vol. 25, Issue 4-5, Jan. 2011, pp. 483-499.

Sun, "Setting the bar for powder flow properties in successful high speed tableting", Powder Technology, vol. 201, Issue 1, Jul. 2010, pp. 206-108.

Tye et al., "Evaluation of the effects of tableting speed on the relationships between compaction pressure, tablet tensile strength, and tablet solid fraction", Journal of Pharmaceutical Science, vol. 94, No. 3, Mar. 2005, pp. 465-472.

Yang et al., "Dry particle coating for improving the flowability of cohesive powders", Powder Technology, vol. 158, Issues 1-3, Oct. 2005, pp. 21-33.

Zhou et al., "Preparation and Characterization of Surface-Engineered Coarse Microcrystalline Cellulose Through Dry Coating with Silica Nanoparticles", Journal of Pharmaceutical Sciences, vol. 101, Issue 11, Nov. 2012, pp. 4258-4266.

* cited by examiner

DRY PROCESSED SURFACE COATED ENGINEERING EXCIPIENTS

CROSS-REFERENCE TO RELATED APPLICATIONS

This application claims priority to U.S. provisional patent application No. 62/378,384, filed Aug. 23, 2016, the disclosure of which is incorporated herein by reference in its entirety.

FIELD OF THE DISCLOSURE

The present disclosure relates to coated pharmaceutical excipients, pharmaceutical blends including the same, and methods of making the same.

BACKGROUND

Excipients are utilized in pharmaceutical tablet formulation in roles such as lubricants, disintegrants, glidants as well as filler-binders Bolhuis, G. K., Armstrong, N. A., Excipients for direct compaction—An update. Pharmaceutical Development and Technology 11, 111-124 (2006); Jivraj, M., Martini, L. G., Thomson, C. M., An overview of the different excipients useful for the direct compression of tablets. Pharmaceutical Science & Technology Today 3, 58-63 (2000)). As a binder, an excipient facilitates the consolidation of powders into tablets. This is a process of reducing pores in a powder bed while creating interparticulate bonds to prepare a compact solid unit dosage. The structure of the powder sample in a die changes and consolidation is brought about by combined actions such as particle rearrangement, plastic deformation, and fragmentation. Another role of the excipients is to negate poor flow, packing density, and compaction properties of the active pharmaceutical ingredients (APIs). For example, when the API is made of fine particles that are cohesive, the importance of achieving good flow and packing of a blend by the inclusion of an excipient is very important. Unfortunately, because API particles are cohesive, such impact is significant unless the drug loading is relatively low, such as about 10 wt % or more preferably about 5 wt %. If the drug loading is higher than about 10%, direct compaction cannot be employed, and granulation such as dry roller compaction or wet granulation may be necessary.

Fine excipients improve tablet strength due to larger available surface area. During powder compaction, particles undergo rearrangement, fragmentation, elastic and plastic deformation. The mechanical integrity of the powder compact is provided by interparticle bonds, which include solid bridges, intermolecular forces, and mechanical interlocking. As explained by the bonding area and bonding strength (BABS) model (Sun et al., Decoding Powder Tabletability: Roles of Particle Adhesion and Plasticity, Journal of Adhesion Science and Technology, 25:4-5, 483-499 (2011)), the strength of a tablet is the result of the increased bonding area due to densification and bonding strength between particles. From this theoretical perspective, fine excipients are advantageous to increase bonding area. However, fine excipients have poor flow and hence currently available fine excipients do not satisfy all the desired requirements. For example, Avicel 105 has superior compaction properties mainly attributed its large bonding surface area (Leuenberger, H., Application of percolation theory in powder technology. Advanced Powder Technology 10, 323-352 (1999); Shi, L., Sun, C. C., 2011. Overcoming poor tabletability of pharmaceutical crystals by surface modification. Pharmaceutical Research 28, 3248-3255 (2011)). However, its fine particle size (~20 μm) makes it very cohesive, leading to relatively low bulk density, flowability (Castellanos, A., The relationship between attractive interparticle forces and bulk behaviour in dry and uncharged fine powders. Advances in Physics 54, 263-276 (2005); Chen, Y., Jallo, L., Quintanilla, M. A. S., Dave, R., 2010. Characterization of particle and bulk level cohesion reduction of surface modified fine aluminum powders. Colloids and Surfaces A: Physicochemical and Engineering Aspects 361, 66-80 (2010); Geldart, D., Abdullah, E. C., Verlinden, A., 2009. Characterisation of dry powders. Powder Technology 190, 70-74 (2009); Huang, Z., Scicolone, J. V., Gurumuthy, L., Davé, R. N., Flow and bulk density enhancements of pharmaceutical powders using a conical screen mill: A continuous dry coating device. Chemical Engineering Science 125, 209-224 (2015)). That leads to consequent handling and feeding problems in pharmaceutical industrial processing. Another example is Avicel 200, which has excellent flow properties. However, the large particle size of Avicel 200 (~200 μm) results in poor compactability relative to Avicel 105 (Rojas, J., Kumar, V., Comparative evaluation of silicified microcrystalline cellulose II as a direct compression vehicle. International Journal of Pharmaceutics 416, 120-128 (2011)).

Various attempts to improved excipients have been made based on the use of MCC along with flow and compaction promoting agents such as silica and surfactants. The processes for preparing the excipients are variations of granulation and/or spray drying, requiring use of additional materials such as liquids, solvents, binder. In addition, the excipients require drying and subsequent processing to produce the required size distributions. See as examples, U.S. Pat. Nos. 6,746,693; 6,858,231; 6,866,867; and 6,936,277. One commercial example of this type of excipient is PROSOLV® SMCC.

The use of flow promoting agents such as silica by itself does not lead to improved compaction properties. Examples are shown where dry blending of the similar ingredients does not lead to improved compaction properties as compared to the same ingredients that undergo wet granulation type processes that create intimate contact between microcrystalline cellulose (MCC) and silica. The addition of silica may reduce the free surface energy of the mixture because, in most cases, silica has lower surface energy than the excipient. However, the presence of silica can lead to inferior compaction properties since lower surface energy leads to weaker tablets. For example, in Fichtner, F., et al., Effect of surface energy on powder compactibility. Pharmaceutical Research 25, 2750-2759 (2008), decrease in tablet strength correlated to the decrease in powder surface energy at constant tablet porosities. Thus, dry processing of an ordinary excipient with silica is not expected to lead to improved tablet compaction properties, even though the flow may be enhanced because of silica.

Dry processing has been shown to be of benefit in enhancing the flow of a variety of powder materials, usually by mixing with glidants, such as fumed or colloidal silica, titania, talc, etc. These "dry blending" techniques and processes have been shown to enhance the flowability of cohesive particles. For example, U.S. Pat. No. 6,833,185 (the '185 patent) describes dry blending of fluidization additives with cohesive powders. The fluidization additives are characterized by a smaller size and lesser mean particle density relative to the cohesive fine powders to which they are added. Of note, "dry blending" in the '185 patent merely blends the fluidization additives with the underlying cohesive powders and does not affect a "coating" of the additives onto (or with respect to) the underlying cohesive powders, as would be the case in "dry coating". This was made clear in Yang, J., et al., Dry particle coating for improving the flowability of cohesive powders. Powder Technology 158, 21-33 (2005), where flow enhancement of cornstarch was examined as a result of "dry blending" with silica compared to "dry coating" with silica. It was shown that flow enhancements are significantly better after dry coating with the same amount of silica instead of ordinary blending.

Researchers from the New Jersey Institute of Technology (NJIT) have investigated dry coating techniques that are superior to dry blending. For example, dry particle coating concepts and techniques are described by Pfeffer et al. in an article entitled "Synthesis of engineered particulates with tailored properties using dry particle coating," Powder Technology 117 (2001), pgs. 40-67, the contents of this article are incorporated herein by reference in its entirety. Here, a dry particle coating may be used to create new-generation materials by combining different powders having different physical and chemical properties to form composites. The new-generation materials described by Pfeffer et al. exhibit unique functionalities and/or improved characteristics relative to known materials. Pfeffer et al. describe techniques for mechanically coating materials ranging in size from 1-200 µm with submicron particles in the absence of a liquid (e.g., a solvent, binder or water).

Dry coating is best done using mixing devices that have higher process intensity. Devices known in the literature for dry coating include, the Hybridizer by Nara Machinery, Japan; the Mechanofusion and its newer variations by Hosokawa Micron, Japan; the Magnetically Assisted Impaction Coating by Aveka, Minnesota; and even a V-blender with in intensifier bar. More recent investigations from New Jersey Institute of Technology (NJIT) and others have revealed that a variety of other high intensity mixing devices may be used. For example, a high-intensity vibration unit called LabRAM, and its larger scale versions from Resodyn, Montana, may be used successfully. Likewise, a conical mill, e.g. Quadro Comil models, may be used under certain conditions to achieve dry coating as disclosed in Huang et al, 2015 (referenced above). U.S. Pat. No. 8,252,370 (the '370 patent) discloses another continuous method where simultaneous milling and coating may be accomplished. As will be apparent to those skilled in art, devices that can provide high intensity mixing actions without significant attrition may be used for dry coating. In dry coating, the finer particles, typically called the guest particles, are coated on to coarser particles, typically called the host particles. FIGS. 1a-e of the present application illustrates this concept for nano-silica coated onto cornstarch. Note that FIG. 1a is a typical un-coated, as received cornstarch particle.

Dry coating is gaining significant interest for pharmaceutical applications. It has been shown that dry coating with flow enhancing agents leads to reduced cohesion, improved flow, increased packing density, and even reduced electrostatic tendency. Observed property enhancements are attributed to intimate coating and spreading of the materials such as nano-silica, as discussed in various publications, see for example, Chen, Y., et al., Fluidization of coated group C powders. AIChE Journal 54, 104-121 (2008); Han, X., et al., Simultaneous micronization and surface modification for improvement of flow and dissolution of drug particles. International Journal of Pharmaceutics 415, 185-195 (2011); and Jallo, L. J., et al., Improvement of flow and bulk density of pharmaceutical powders using surface modification. International Journal of Pharmaceutics 423, 213-225 (2012).

As an example of dramatic improvements in bulk density and flow, FIGS. 2a-b of the present application illustrates that if there is no silica or dry coating, how packing density decreases and cohesion increases as ibuprofen is micronized down to sizes ranging from about 28 to 5 microns. In contrast, if simultaneous dry coating is done while milling, the decrease in bulk density and increase in cohesion are significantly eliminated. Also, the properties improve drastically as compared to simple silica blending as shown for 5 and 28 micron sized powders. In addition, dry coating with hydrophilic silica has also been shown to greatly reduce electrostatic charging tendency, for example, in Jallo, L. J., et al., "Explaining Electrostatic Charging and Flow of Surface-Modified Acetaminophen Powders as a Function of Relative Humidity Through Surface Energetics", Journal of Pharmaceutical Sciences, 104, 2225-2232 (2015).

Chen et al. 2008 (referenced above) demonstrates that mechanistic models can predict how the extent of guest particle coverage impacts reduction in particle cohesion forces which lead to reduced cohesion and hence improved flow and packing. Based on the contact model developed by Chen et al. 2008, an important factor called guest particle surface area coverage (SAC) is identified. While the derivation assumes that host and guest particles are monodisperse, the guest particles are uniformly coated on to host particles, and that the amount is only sufficient to create a monolayer, the relationship between the guest wt % and percentage SAC (in range 0 to 100) is given by the Equation (1). Here N is the average number of guest particles per host particle, d is the diameter of the guest, D is the diameter of the host, and $\rho_d$ and $\rho_D$ are material densities of guest and host respectively.

$$\text{Wt \%} = \frac{(Nd^3\rho_d)}{(D^3\rho_D) + (Nd^3\rho_d)} \times 100\% \qquad (1)$$

$$SAC = \frac{N \times \frac{\pi d^2}{4}}{4\pi \left(\frac{d+D}{2}\right)^2} \times 100\% = \frac{N \times d^2}{4(d+D)^2} \times 100\% \approx \frac{N \times d^2}{4D^2} \times 100\% \qquad (2)$$

In Equation (1), given a desired SAC, given by Equation (2), N and guest wt % can be computed. It is shown through particle contact models that desired SAC is between about 1 and 100%. In addition, these contact models also indicate that the desired size of the silica particle should be in range about 5 nm to 30 nm. In this invention, selection of the best silica considers these and other factors such as its impact on flow and bonding strength. If the coating device is efficient and the host and guest materials have compatibility based on their surface free energy as disclosed in Huang et al. 2015, coating can indeed be very uniform and theoretical SAC predicted from these equations would be fairly close to experimental, as shown in Yang et al. 2005.

Overall, the prior efforts have attempted to disclose various aspects of better compacting excipients that include silica, surfactant and other materials, they have not shown how dry processing can lead to better compacting excipients. Rather, it has been demonstrated that dry blending did not provide improved compaction properties, see for example, Chattoraj, S., et al., Profoundly improving flow properties of a cohesive cellulose powder by surface coating with nano-silica through comilling. Journal of Pharmaceutical Sciences 100, 4943-4952 (2011); Zhou, Q., et al., "Preparation and Characterization of Surface-Engineered Coarse Microcrystalline Cellulose Through Dry Coating with Silica Nanoparticles," Journal of Pharmaceutical Sciences, 101:4258-4266 (2012). It was shown that dry coating of silica on fine (Avicel® 105), and coarse (Avicel 102) excipients may be achieved using many passes of a conical milling device, e.g., comil. The resulting product was found to have enhanced flow. These dry coated excipients produced weaker 100% MCC placebo tablets, although the tablet strength was found to be still acceptable for Avicel 105 as long as sufficiently high compaction force was used. This work did not show tablet compaction using pharmaceutical blends of API and dry coated excipients. However, it is expected that blending the dry coated excipients with poorly flowing and poorly compacting APIs, tablets would not achieve sufficient compaction. The prior art suggests that dry coating will lead to poorer compaction properties because it is likely to lead to reduced surface energy after dry coating (Sun, C., "Decoding Powder Tabletability: Roles of Particle Adhesion and Plasticity," Journal of Adhesion Science and Technology, 25:483-499 (2011); Fichtner, et al. 2008; Etzler, F. M., et al., Tablet tensile strength: An adhesion science perspective. Journal of Adhesion Science and Technology 25, 501-519 (2011); and Han, X., et al., Passivation of high-surface-energy sites of milled ibuprofen crystals via dry coating for reduced cohesion and improved flowability. Journal of Pharmaceutical Sciences 102, 2282-2296 (2013)).

For commercially available excipients, one or more properties, e.g., flow, packing density, compaction, hydrophobicity, is sacrificed in order to meet a specific property. For example, finer grades of Avicel, e.g., PH105, have better compaction properties, largely attributed to higher surface area, but its finer size makes it poorly flowing and less dense. For example, PROSOLV® SMCC, hereafter "Prosolv", a commercially available excipient considered to have good flow, density and compaction properties, contains large amounts (~2%) of nano-silica. Higher silica content negatively impact flexibility in formulating tablets since total silica amounts must be kept within physiologically acceptable limits. In addition, the manufacturing process such as in Prosolv may have bigger environmental footprint and extra steps in processing.

There is a need for improved excipients that have superior flow properties while, at the same time, producing a pharmaceutical tablet with sufficient strength. There is also a need for excipients that facilitate direct compaction even at relatively large drug loadings, for example, 20 wt %, 30 wt %, or even as high as 50 wt % or higher. Thus, there is a need in the art for an excipient having good flow property, good packing density, and good compactibility. The excipient should have a fine size, e.g., D50 under 50 microns. In some embodiments, a particle size where D90<90 microns is preferred. The excipient should also have a simplified manufacturing scheme and minimal use of silica or other flow promoting agents. The role of an excipient is to allow preparing better blend formulations so that even for fine and cohesive API powders, the blend can be produced having good flow (measured by FFC, for example), good bulk density, and importantly, good binding properties for making tablets while reducing the amount of excipient required. It would be beneficial to have excipients that can be used in lesser amounts so that the drug amount in a tablet, i.e., percent drug loading, can be increased. There is also an important consideration with respect to manufacturing process used to go from a blend to tableting. Most desired route is what is called direct compression or compaction. In that case, the blend is directly converted to a tablet using a high-speed tableting machine. If the blend does not have desirable flow, bulk density and compaction properties, the next option is dry granulation, which is usually done via roller compaction. This processing route adds a few steps to manufacturing process but avoids use of liquids and associated need of drying which is the case for wet granulation. Thus, good excipients may facilitate wider use of direct compression; failing which, roller compaction and thus avoid use of wet granulation. For example, it is suggested by Sun, 2010, and Shi et al., 2011 (Sun, C. C., 2010. Setting the bar for powder flow properties in successful high speed tableting. Powder Technol. 201, 106-108; Shi, L., Chattoraj, S., Sun, C. C., 2011. Reproducibility of flow properties of microcrystalline cellulose—Avicel PH102. Powder Technol. 212, 253-257) that the bulk density and the FFC (at 3 kPa consolidation stress) of Avicel® 102 may be used as benchmark values to assess suitability of a blend for high-speed direct compaction tableting. These values are: bulk density of about 0.325 g/mL and FFC of just under 7. Based on this recommendation a person skilled in art can develop a guideline for blend suitability for direct compression, roller compaction, and wet granulation as: Direct compression possible when FFC>about 7, and BD>about 0.32 g/mL; roller compaction when FFC>about 3, and BD>about 0.27 g/mL; otherwise, wet granulation may be necessary. Though this recommendation can act as a guideline to one of ordinary skill in the art, it does not include binding properties and corresponding tablet mechanical properties.

Since direct compression is the easiest path to tablet manufacturing, excipients need to be developed that facilitate direct compression or compaction of tablets even at relatively large drug loadings, for example, 20 wt %, 30 wt %, or even 50 wt % and higher. The excipients should also facilitate roller compaction when very high drug loading may not allow for direct compression at much higher drug loadings, for example, about 70 wt % or higher. Therefore, excipients with excellent binding properties that enable broader ranges of blend formulations than previously possible are desirable.

Developing formulations at higher drug loadings become more challenging when the API is fine or cohesive. A cohesive API has poor flow and bulk density; typically, FFC is 3 or lower, and bulk density is about 0.2 or lower. A good example of this is micronized acetaminophen (mAPAP) which has D50 of about 10 microns and was a subject of an interesting study by Huang et al., "Improved blend and tablet properties of fine pharmaceutical powders via dry particle coating," *International Journal of Pharmaceutics*, Vol. 478(2) p 447-455 (2015). This study considered the API (mAPAP) before and after dry coating, where dry coating using a hydrophobic silica R972P was intended to improve flow (FFC) and bulk density of mAPAP. In this study, mAPAP was considered as a model cohesive API and dry coated mAPAP was considered as not cohesive because the study showed (refer to FIG. 1 in Huang et al., 2015) that as-received mAPAP had FFC of about 2 and bulk density of about 0.2 g/mL; and after dry coating with R972P, FFC increased to about 4 and bulk density nearly doubled.

This study also considered blends of mAPAP and an excipient at 10 wt %, 30 wt %, and 60 wt % drug loading. As was shown in FIG. 3 of Huang et al. 2015, for 10% drug loading with using fine excipients (combination of Avicel 105® and Lactose 450), the difference between FFC and bulk density for mAPAP with and without dry coating was not significant. However, when drug loading was 30% or 60%, the non-dry coated API (mAPAP) had poor flow (FFC of below 3) and those blends cannot be used for direct compression tableting. In contrast, the dry coated API was not cohesive, where the FFC increased considerably and so did bulk density. This study showed that having a better excipient is highly desirable as drug loading increases beyond about 10% for cohesive APIs. The blend (FIG. 3 of Huang et al. 2015) also considered a dry coating excipient including Avicel 105® in combination with a dry coated API, and the results indicate that as drug loading increases, there is only a marginal impact of better flowing excipient. Such results are consistent with our results for well-flowing excipients such as Avicel® 102 and Prosolv® 90 HD, which do not provide good flow for even 30 wt % mAPAP blends (see FIG. 17(b)), and for 60% mAPAP loading, they are very poor in terms of FFC and bulk density of mAPAP blends (see FIG. 17(c)).

As discussed above, FFC and bulk density are necessary conditions for direct compression but are not alone sufficient since binding properties are also important. Huang et al., 2015 showed what happens to tablet strength for cohesive (as-received mAPAP) and not cohesive (dry coated mAPAP) APIs. As shown in FIG. 6 of Huang et al., 2015 compared to placebo tablets, the blend tablets had reduced strength for both fine and coarse set of excipient blends. However, these results indicate that even when the tablet strength is drastically reduced, when the API was dry coated, the tablet strength loss was lesser. It has been shown that the tablet strength becomes lower when surface energy is reduced by Nazik A. El Gindy and Magda W. Samaha, Tensile strength of some pharmaceutical compacts and their relation to surface free energy, International Journal of Pharmaceutics, 13:35-46; Effect of surface energy on powder compactibility, Pharmaceutical Research, Vol. 25, No. 12, 2750-2759 (1983); Frank M. Etzler, et al., Tablet Tensile Strength: An Adhesion Science Perspective, Journal of Adhesion Science and Technology, 25:4-5, 501-519 (2011). This explains why the blends had poorer tablet strength since surface energy of mAPAP is higher than the excipients. For blends, Etzler et al., 2011 propose equations that indicate that the strength of a compact of a mixture is proportional to surface energy of individual constituents, weighted by an exponent that is their individual surface area fractions (see equation 21 of Etzler et al., 2011). Thus, when an excipient is dry coated, which reduces its surface energy, will lead to poorer compact strength. Therefore, based on the studies of Huang et al., 2015, one of ordinary skill in the art would conclude that dry coated excipients would produce blends having sufficient table strength. Moreover, the work of Huang et al. 2015 was to show that dry coating a fine cohesive API eliminates the influence of the excipients (see FIG. 5 of Huang et al. 2015) in terms of blend FFC and bulk density. In terms of their fortuitous results for tablet strength of dry coated mAPAP blends being higher than corresponding blends of as received mAPAP, Changquan Calvin Sun, Decoding Powder Tabletability: Roles of Particle Adhesion and Plasticity, Journal of Adhesion Science and Technology, 25:4-5, 483-499 (2011) offers a partial explanation. Sun 2011 discussed that the bonding area-bonding strength (BABS) model should be considered, which suggests that both the bonding strength, considered related to surface energy, and bonding area have an impact. Sun 2011 stated that; "The BABS model can explain the observations that particle size influences tabletability of plastic powders but not of brittle powders." Further, " . . . tabletability of lubricated powders is better than that of unlubricated powders for brittle materials". Thus, for the API (mAPAP), which is brittle material, compared to the excipient (microcrystalline cellulose (MCC) and Avicel® grades) which are ductile, one of ordinary skill in the art would not expect adverse impact of dry coating APIs based on Huang et al. 2015. In addition, dry coated mAPAP has significantly reduced agglomeration as compared to as-received mAPAP, hence its effective bonding area is higher, which as per BABS model explain why tablet strength for dry coated mAPAP blends is higher than as-received mAPAP. On the other hand, for ductile excipients, dry coating would not be advisable since doing so would lead to poorer tablet strength in a blend since the excipients would have reduced surface energy, hence bonding strength and unlike brittle, more cohesive APIs, corresponding increase in surface area is unlikely to compensate for reduced bonding strength.

There is a need in the art for an excipient having good flow property, good packing density, and good compactibility not just by itself but in blends at higher drug loadings, in particular for cohesive APIs. Excipients like Avicel 102® and grades of Prosolv® have excellent compaction properties by themselves, but are poor in blends of cohesive APIs, even when the API is dry coated.

SUMMARY

Since an excipient has better binding properties when it is fine and has larger surface area, the excipient should have a fine size, e.g., D50 under 50 microns. More preferably, it should have D50 under 35 microns and D90<80 microns is preferred. However, fine excipients have poor flow. Dry coating improves upon these deficiencies and surprisingly, it is found that dry coating does not have detrimental effect on tablet strength of blends of cohesive APIs at high drug loadings. The excipient should also have a simplified manufacturing scheme and minimal use of silica or other flow promoting agents. Accordingly, dry coated excipients can be produced by a manufacturing process that does not require use of any liquids via simultaneous milling and dry coating. Dry coated excipients can also advantageously be used to form cohesive API blends by direct compression or roller compaction without the need for wet granulation.

In some embodiments, a pharmaceutical blend includes a cohesive active pharmaceutical ingredient (API) and a coated pharmaceutical excipient. The coated pharmaceutical excipient may be present in an amount of about 1 wt % to 99 wt %, based on the total weight of the pharmaceutical blend. The coated pharmaceutical excipient may comprise a core and a shell surrounding the core, wherein the shell partially covers the core of the pharmaceutical excipient.

In some embodiments, the core comprises one more selected from the group consisting of microcrystalline cellulose (MCC), pre-gelatinized starch, lactose, mannitol, polyols, dibasic calcium phosphate dehydrate, calcium carbonate, croscarmellose sodium, confectioner sugar, etc.

In some embodiments, the shell comprises one or more compounds selected from the group consisting of glidants, lubricants, surfactants, such as, silica, titania, talc, magnesium stearate, steric acid, sodium dodecyl sulfate, etc.

In some embodiments, the silica comprises hydrophilic silica having a specific surface area ranging from about 175 $m^2/g$ to about 225 $m^2/g$.

In some embodiments, the silica comprises a functionalized hydrophobic having a specific surface area ranging from about 90 $m^2/g$ to about 130 $m^2/g$.

In some embodiments, the cohesive API is a non-coated cohesive API.

In some embodiments, the cohesive API has a bulk density ranging from about 0.05 g/mL to 0.5 g/mL and an flow function coefficient (FFC) ranging from about 1.0 to 3.5.

In some embodiments, the shell is present in an amount ranging from about 0.01 wt % to about 1.95 wt %, based on the weight of the core.

In some embodiments, the shell is present in an amount ranging from about 0.05 wt % to about 1.0 wt %, based on the weight of the core.

In some embodiments, the API is present in an amount ranging from about 20 wt % to about 99 wt %, based on the total weight of the pharmaceutical blend.

In some embodiments, the API is present in an amount ranging from about 20 wt % to about 60 wt %, based on the total weight of the pharmaceutical blend.

In some embodiments, the bulk density of the coated pharmaceutical excipient ranges from about 0.3 g/mL to about 0.7 g/mL.

In some embodiments, an flow function coefficient (FFC) of the coated pharmaceutical excipient ranges from 3 to 30.

In some embodiments, the bulk density of the pharmaceutical blend ranges from about 0.2 g/mL to about 0.99 g/mL.

In some embodiments, the flowability of the pharmaceutical blend ranges from about 2 to about 30.

In some embodiments, the excipient has a D50 particles size ranging from about 20 to about 50 microns, and wherein the shell is present in an amount of about 0.01 wt % to about 1 wt %, based on the total weight of the core.

In some embodiments, the shell comprises discrete particles having an average particle size ranging from about 5 nm to 35 nm disposed on the surface of the core.

In some embodiments, the core comprises microcrystalline cellulose (MCC) having a D50 particle size ranging from about 20 to about 40 microns.

In some embodiments, a pharmaceutical tablet is made from the blend, the tablet having a porosity ranging from about 0.05 to about 0.35 and a tensile strength ranging from about 1 MPa to about 10 MPa.

In some embodiments, a coated pharmaceutical excipient includes a core and a shell surrounding the core. In some embodiments, the shell partially covers the core of the pharmaceutical excipient. In some embodiments, the excipient has a D50 particle size ranging from about 20 to about 50 microns. In some embodiments, the shell is present in an amount of about 0.01 wt % to about 1 wt %, based on the total weight of the core.

In some embodiments, the shell comprises discrete particles having an average particle size ranging from about 5 nm to 35 nm disposed on the surface of the core.

In some embodiments, the core comprises microcrystalline cellulose (MCC) having a D50 particle size ranging from about 20 to about 40 microns.

In some embodiments, a method of forming a pharmaceutical tablet includes compressing a blend of a cohesive API and a coated pharmaceutical excipient to compress the blend into a pharmaceutical tablet, wherein the method does not include a wet granulation step.

In some embodiments, the coated pharmaceutical excipient is present in an amount of about 1 wt % to 99 wt %, based on the total weight of the blend.

In some embodiments, the coated pharmaceutical excipient comprises a core and a shell surrounding the core.

In some embodiments, the shell partially covers the core of the pharmaceutical excipient.

In some embodiments, the excipient has a D50 particle size ranging from about 20 to about 50 microns, and wherein the shell is present in an amount of about 0.01 wt % to about 1 wt %, based on the total weight of the core.

In some embodiments, the shell comprises discrete particles having an average particle size ranging from about 5 nm to 35 nm disposed on the surface of the core.

In some embodiments, the core comprises microcrystalline cellulose (MCC) having a D50 particle size ranging from about 20 to about 40 microns.

DETAILED DESCRIPTION

Figure 1A:
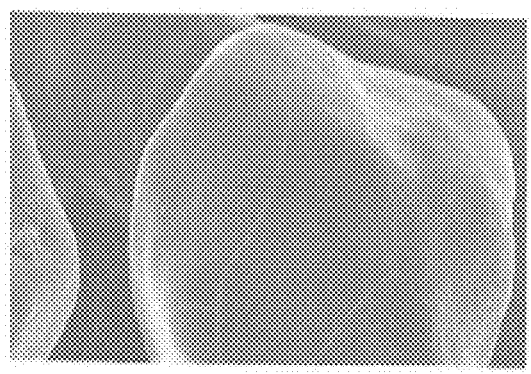
FIGS. 1a-e are, respectively, scanning electron microscope (SEM) images of nano-silica dry coated onto cornstarch, uncoated cornstarch, nano-silica dry coated onto cornstarch at 0.05 wt %, nano-silica dry coated onto cornstarch at 0.02 wt %, and nano-silica dry coated onto cornstarch at 0.5 wt %.
Figure 1B:
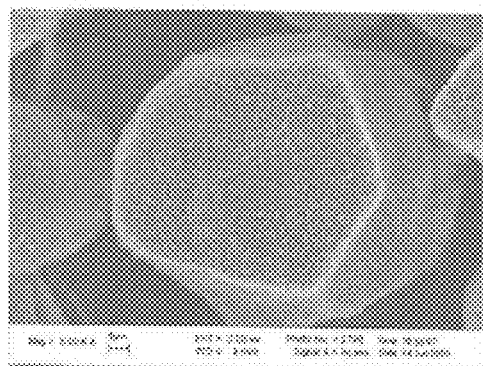
Figure 1C:
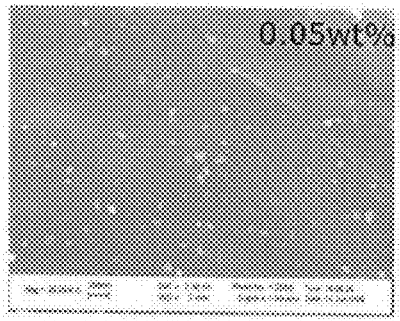
Figure 1D:
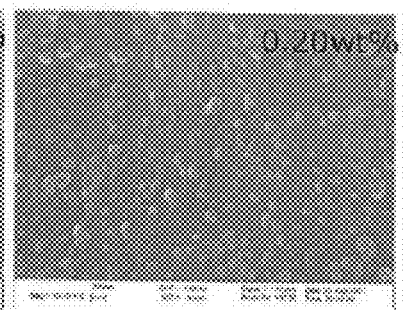
Figure 1E:
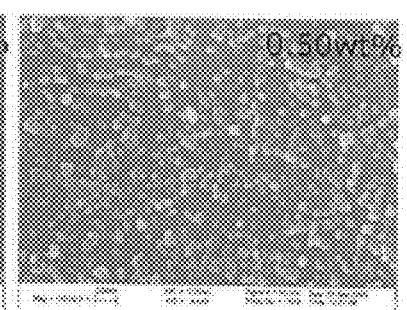
Figure 2A:
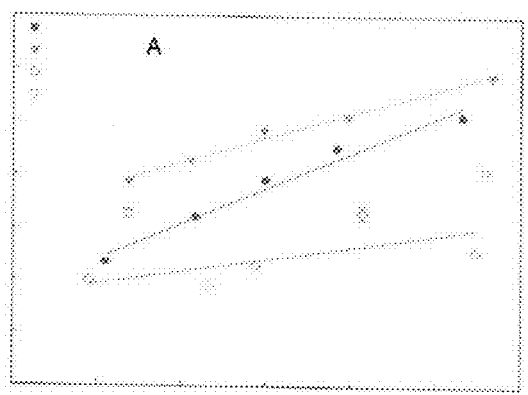
FIGS. 2a-b are, respectively, plots showing improved powder bulk density and reduced cohesion before and after nano-silica dry coating onto various sizes of milled ibuprofen.
Figure 2B:
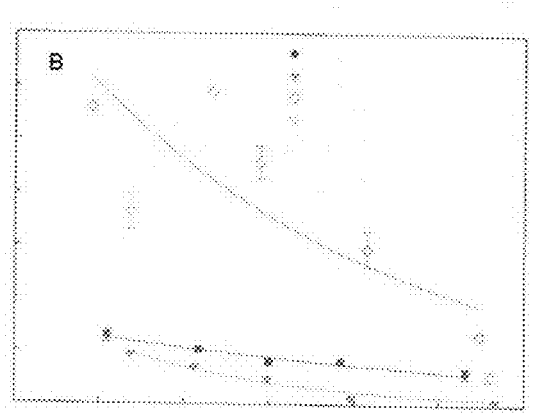
Figure 3A:
FIGS. 3a-h are, respectively, SEM images of Lactose 350, Lactose 450, Pharmatose® DCL11, Avicel® 101, Avicel® 102, Avicel® 105, Avicel® 200, and Prosolv® 90 HD.
Figure 3B:
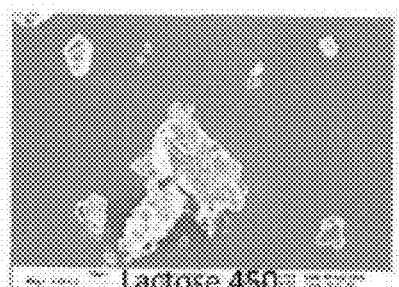
Figure 3C:
Figure 3D:
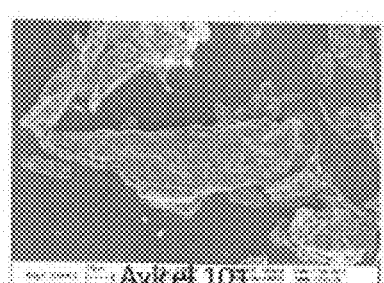
Figure 3E:
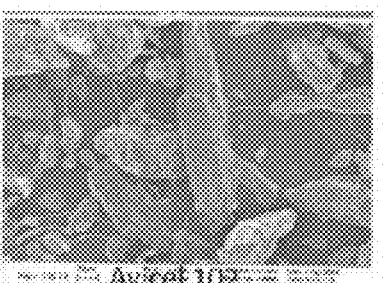
Figure 3F:
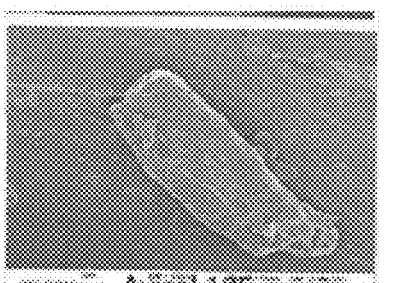
Figure 3G:
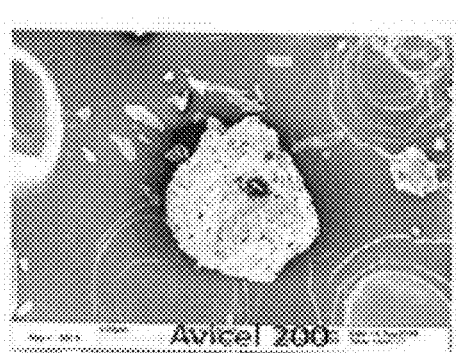
Figure 3H:
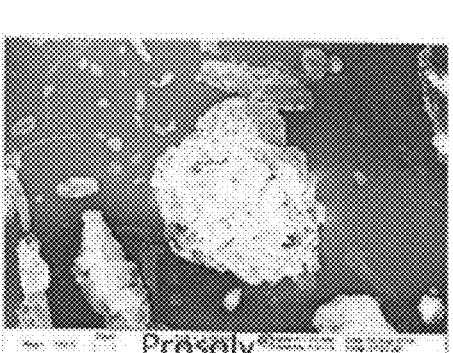
Figure 4A:
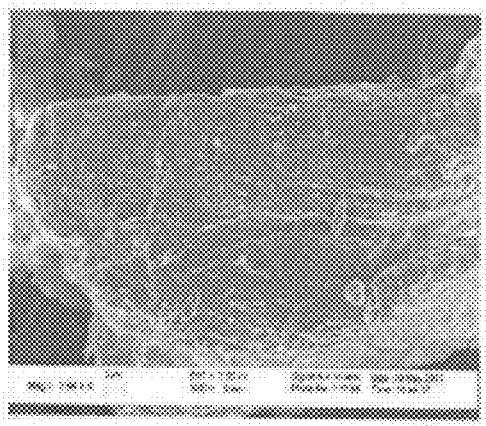
FIGS. 4a-d are, respectively, SEM images of dry coated Avicel® 101 with 1 wt % M5P, dry coated Avicel® 101 with 1 wt % R972P, dry coated lactose 350 with 1 wt % M5P, and dry coated lactose 350 with 1 wt % R972P.
Figure 4B:
Figure 4C:
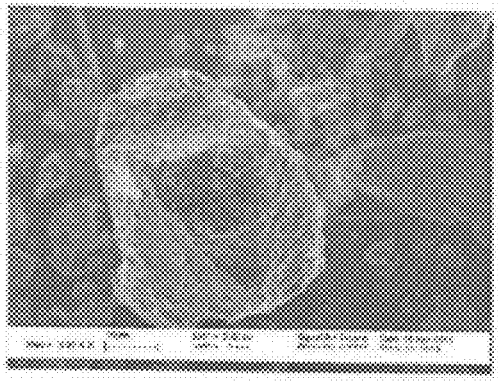
Figure 4D:
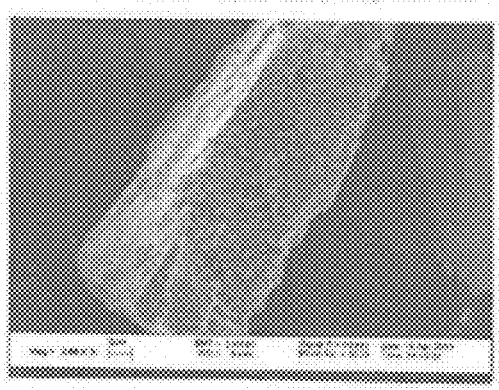

Dry coating excipients, pharmaceutical blends including the same, and methods of making the same are disclosed herein.

General

It should be understood that a description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.3, 3, 4, 5, 5.7 and 6. This applies regardless of the breadth of the range.

Unless noted otherwise, particle size distribution provided herein is volume based particle size distribution was measured by a laser diffraction particle analyzer (Rodos/Helos system, Sympatec, NJ). Size statistics in terms of $d_{10}$, $d_{50}$ and $d_{90}$ are reported, which are the values of the particle diameter at 10%, 50% and 90% respectively in the cumulative volumetric particle size distribution. In the Rodos/Helos system, the Rodos device works by venturi principle to disperse the powder, and the Helos unit uses laser diffraction principles of Fraunhofer Enhanced Evaluation (FREE) and Mie Extended Evaluation (MIEE) theories of light scattering to determine the particle size. Size statistics of $d_{10}$, $d_{50}$ and $d_{90}$ at dispersion pressure of 0.1 bar are reported utilizing the FREE theory, the details for which can be found in Han et al. "Passivation of high surface energy sites of milled ibuprofen crystals via dry coating," *Journal of Pharmaceutical Sciences*, Vol. 102(7), 1-15 (2013) and Jallo et al. "Improvement of flow and bulk density of pharmaceutical powders using surface modification," *International Journal of Pharmaceutics*, 423 213-225 (2012).

Unless otherwise noted, bulk density and flowability, i.e., flow function coefficient (FFC), as provided herein is obtained using a Freeman FT4 powder tester (Freeman Technologies Ltd., Worcestershire, UK), where the bulk density and the flow function coefficient (FFC) were defined as the ratio of consolidation stress to the unconfined yield stress. The FFC was evaluated from a shear test under the consolidation pressure of 3 kPa. Detailed procedures for both may be found in Freeman et al., Measuring the flow properties of consolidated, conditioned and aerated powders—A comparative study using a powder rheometer and a rotational shear cell. Powder Technology 174, 25-33 (2007) and Huang et al., Flow and bulk density enhancements of pharmaceutical powders using a conical screen mill: A continuous dry coating device. Chemical Engineering Science 125, 209-224 (2015).

Though FFC is the flowability measure used herein, one of ordinary skill in the art would recognize that other flow indices can be used, such as angle of repose, Carr index, Hausner ratio, flow through orifice testing device, and others. Further, one of ordinary skill in the art would be able to use a suitable ring shear tester or equivalent to determine FFC at low pre-consolidation in a manner comparable to FT4. A classification of powder flow behavior based on FFC is defined by Schulze, D., Powders and Bulk Solids. Springer (2008) according to the FFC value: "FFC<1—not flowing, 1<FFC<2—very cohesive, 2<FFC<4—cohesive, 4<FFC<10—easy flowing, and FCC>10—free-flowing".

Bulk density was measured through a standard FT4 testing procedure that first conditions the powder to yield very repeatable results for the bulk density as discussed in the detailed procedures of Freeman, et al. mentioned above. Prior to powder characterization the powder was conditioned to remove stress or excess air from the powder bed by passing a conditioning blade through the powder bed. This process will be referred to as the conditioning cycle. The conditioned bulk density was measured by loading the powder samples into the 25 ml split vessel above the minimum fill level. After a conditioning cycle was performed the vessel was split to remove the top portion of the powder; the density was determined from the mass of the remaining powder in the 25 ml vessel.

For compaction studies as discussed herein, tablets of individual excipients or blends including excipients were prepared under four different compaction forces (0.5, 1.0, 1.5, and 2.0 metric tons) with a 500 mg powder sample using a stainless die of 0.5 inch inner diameter with flat-faced round punch. The procedure described here for tablet compaction test is used in all subsequent examples, unless stated otherwise. The die and the punch were cleaned by alcohol wipes before each compression. Tablets were placed vertical on the holder of texture analyzer model TA-XT Plus (Texture Technologies Corp., USA) and probe moves at 10 mm/s till the tablet breaks. The maximum breaking force was recorded. The tensile strength was calculated from equation below, where F is the tablet breaking force, $D_t$ is the tablet diameter, and t is the thickness of the tablet as discussed in Fell, et al., Determination of Tablet Strength by the Diametral-Compression Test, Journal of Pharmaceutical Sciences 59, 688-691 (1970).

$$\sigma = \frac{2F}{\pi D_t t} \quad (3)$$

First, the apparent particle density, $\square_{app}$, for each powder (also referred to as the gas pycnometric and true density of particles) was determined using a helium multipycnometer (Model MVP-6DC, Quantachrome instruments, FL, 33426, USA; repeated five time to get an average). After this is determined, the porosity of each tablet ($\varepsilon$) was calculated from the apparent particle density ($\rho_{app}$) and the diameter (D), thickness (t) and weight (w) of the tablets using the following equation. All quantities are in SI units.

$$\varepsilon = 1 - \frac{4w}{\pi t D^2 \rho_{app}} \quad (4)$$

In addition to measuring the porosity of the tablets, the porosity of a powder sample, and its complement, packing fraction can be also determined as follows. The porosity was calculated from their measured bulk density using the Freeman FT4 powder tester (Freeman Technology Ltd., UK). The material was filled into 25 mm×25 ml splitting cylindrical vessel. The powder was first "conditioned" with a twisted blade (helix angle of −5°, 23.5 mm in diameter, tip speed of 100 mm/s) which was performed to remove excess air, remove any historic effect of the material, and to create a uniform powder bed. After conditioning, the vessel was split to remove excess powder to obtain a volume of 25 ml. The mass of the material in the vessel is recorded to obtain the bulk density (mass of powder/volume of vessel). The measurement was performed in triplicate and found to be highly reproducible with standard relative deviations <2% in most cases. The porosity c is then calculated from equation below, $$\varepsilon = 1 - \frac{\rho_b}{\rho_p} \quad (5)$$

where $\rho_b$ is the bulk density and $\rho_p$ is the particle (true) density of the host material that can be measured using a pycnometer mentioned before. The packing fraction is simply 1−ε.

Dry Coated Excipients

Excipients can be used as diluents and to promote tabletability. For example, excipients can be brittle or non-brittle, water soluble or insoluble. It is preferable that excipients have advantageous properties such as good flow, good packing density, and good compactibility. Dry coating of excipients can be used to improve upon excipient properties.

The dry coated excipients can be in the form of primary or secondary particles. The dry coated excipients can be in a regular shape, such as spherical, or an irregular shape. The dry coated excipients can range in particle size up to about 500 microns. In some embodiments, the particle size ranges from about 10 microns to about 300 or even 500 microns. In some embodiments, the particle size ranges from about 20 microns to about 200 microns. In some embodiments, the particle size ranges from about 20 to about 50 microns. In some embodiments, the particle size ranges from about 20 to about 40 microns. In some embodiments, the particle size ranges from about 20 to about 45 microns.

Dry coated excipients include a host material and a guest material. The host material and guest material may be in the form of a core-shell structure, where the host material is the core and the guest material is the shell. The guest material at least partially covers the surface of the host material. In some embodiments, the guest material may resemble discrete particles on the surface of the host material.

The host material can be of any suitable shape, such as spherical or an irregular shape. The host material may be any suitable pharmaceutical excipient. Exemplary pharmaceutical excipients include one or more of cellulosic materials such as microcrystalline cellulose (MCC), hydroxyl propyl methyl cellulose (HPMC) or hypromellose, hydroxyl propyl cellulose (HPC), lactose and its derivatives, mannitol and other polyols, variety of starches including pre-gelatinized, dibasic calcium phosphate dehydrate, calcium carbonate, croscarmellose sodium, confectioner sugar, plain or anhydrous calcium phosphate, and others. In some embodiments, the host material comprises microcrystalline cellulose (MCC) having a particle size ranging from about 20 to about 40 microns.

Several exemplary commercial excipients (e.g., host material) are provided in Table 1 along with nominal particle sizes and density. These commercial excipients include, cornstarch (available from Argos), Lactose 350 (DFE Pharma, USA), Lactose 450 (DFE Pharma, USA, Avicel® 101 (FMC Biopolymer, USA), Avicel® 102 (FMC Biopolymer. USA), Avicel® 105 (FMC Biopolymer, USA), Avicel® 200 (FMC Biopolymer, USA), and Pharmatose® DCL11 (DFE Pharma, USA). FIG. 1a depicts a scanning electron microscopy (SEM) micrograph of cornstarch. FIGS. 3a-h depict SEM micrographs of, respectively, Lactose 350, Lactose 450, Pharmatose® DCL11, Avicel® 101, Avicel® 102, Avicel® 105, Avicel® 200, and Prosolv® HD 90 (JRS Pharma, USA). As shown in an as-received (A.R.) state, Pharmatose® DCL11, Avicel® 200, and Prosolv® are granulated, whereas the other commercial excipients depicted in FIG. 3 are not.

TABLE 1

| Excipients | Particle Size (μm) | | | True Density (g/mL) |
| --- | --- | --- | --- | --- |
| | D10 | D50 | D90 | |
| Micronized APAP | 2 | 10 | 37 | 1.29 |
| Cornstarch | N/A | 15 | N/A | 1.45 |
| Avicel ® 101 | 22 | 66 | 164 | 1.56 |
| Avicel ® 102 | 32 | 122 | 244 | 1.56 |
| Avicel ® 105 | 7 | 19 | 40 | 1.56 |
| Avicel ® 200 | 57 | 186 | 324 | 1.56 |
| Lactose 350 | 3 | 26 | 78 | 1.54 |
| Lactose 450 | 3 | 17 | 48 | 1.54 |
| Pharmatose ® DCL11 | 43 | 112 | 205 | 1.54 |

The host material may have an average particle size ranging from about 2 microns to about 500 microns. In some embodiments, the average particle size ranges from about 5 microns to about 200 microns. In some embodiments, the average particles size ranges from about 10 microns to about 120 microns. In some embodiments, the particle size ranges from about 20 microns to about 200 microns. In some embodiments, the particle size ranges from about 20 to about 50 microns. In some embodiments, the particle size ranges from about 20 to about 40 microns. In some embodiments, the particle size ranges from about 20 to about 45 microns.

The guest material may be a material that improves properties of the host material. The guest material may improve one or more of flowability, bulk density, or tableting properties of the host material. The guest material may be one or more of a dry coating nano-silica, or another fine additive that is hydrophobic, hydrophilic, or combination thereof. The guest material may include a functionalized hydrophobic silica (e.g., R972P discussed below). Functionalization can include post chemical treatment with alkoxysilanes, silazanes, siloxanes, and the like. The guest material may include one or more compounds, such as glidants, lubricants, surfactants, including silica, titania, talc, magnesium stearate, steric acid, sodium dodecyl sulfate. Exemplary guest materials include one or more of hydrophilic fumed silica Cab-o-sil M-5P (M5P, Cabot, U.S.A), Aerosil 200 hydrophilic fumed silica (A200, Evonik, U.S.A) and hydrophobic Aerosil R972 Pharma (R972P, Evonik, U.S.A). Properties of the aforementioned guest particles are provided in Table 2.

TABLE 2

| Guest | Primary Particle Size (nm) | Specific Surface Area (m²/g) | True Density (g/mL) | Hydrophilicity |
| --- | --- | --- | --- | --- |
| M5P | 20 | ~200 | 2.2 | hydrophilic |
| R972P | 20 | 90-130 | 2.65 | hydrophobic |
| A200 | 12 | 175-225 | 2.2 | hydrophilic |

The guest material at least partially covers the surface of the host material. In some embodiments, guest material comprises discrete particles having an average particle size ranging from about 5 nm to 35 nm disposed on the surface of the host material. The guest material may be present in an amount ranging from 0.01 wt % to 5 wt %, based on the weight of the host material. In some embodiments, the guest may be present in an amount ranging from 0.1 wt % to 2 wt %, based on the weight of the host material. In some embodiments, the guest may be present in an amount ranging from 0.01 wt % to 1.95 wt %, based on the weight of the host material. In some embodiments, the guest may be present in an amount ranging from 0.05 wt % to 1 wt %, based on the weight of the host material. More preferably, the guest may be present so as to achieve specific surface area coverage (SAC) by adjusting an amount of the guest material ranging from 0.2 wt % to 1.5 wt %, based on the weight of the host material. In such cases, the SAC can range from 1% to 150%. In some embodiments, SAC can range from 10% to 90%. The amount of silica and theoretical SAC are interchangeable provided that the amount of silica is no more than what would be required to achieve 100% theoretical SAC and is estimated using the equations provided. Further, amongst these three silica choices, A200 may be the best choice because of its smaller size, which also leads to lower silica wt % required for a given theoretical SAC. In addition, it has slightly higher specific surface energy than R972P, making it more preferable from the adverse impact on its bonding strength.

Flowability of the dry coated excipients expressed in FFC may range from 1 to 30. In some embodiments, the FFC ranges from 3 to 30. In some embodiments, flowability may range from 4 to 15.

Bulk density of the dry coated excipients may range from 0.2 g/mL to 1.2 g/mL. In some embodiments, bulk density may range from 0.35 g/mL to 0.9 g/mL. In some embodiments, the bulk density of the coated pharmaceutical excipient ranges from about 0.3 g/mL to about 0.7 g/mL.

Tensile strength of a 0.5 inch inner diameter tablet of the dry coated excipient formed at about 114 MPa force of the dry coated excipients may range from 1 MPa to 12 MPa. In some embodiments, tensile strength may range from 2 MPa to 10 MPa.

Porosity of a 0.5 inch diameter tablet of the dry coated excipient formed at about 114 MPa force of the dry coated excipients may range from 0.05 to 0.40. In some embodiments, porosity may range from 0.1 to 0.3.

Method of Making Dry Coated Excipients

Dry coated excipients can be made by surface modification of the host material using a dry mechanical device for blending the host material with the guest material. The dry coating process eliminates use of liquids, solvents, liquid-binders, wet processing followed by drying and additional steps. The methods of making a dry coated excipient do not necessarily require excessive amounts of the guest material. The methods apply the guest material to surfaces of the host material, resulting in a dry coated excipient that is in the form of a core-shell structure, and not a mixture of host material granules and guest material granules.

The method may optionally begin by determining host-guest compatibility and guest material amount as discussed herein.

The method may include mixing the host material and the guest material using a surface modification device, such as a LabRAM device, or another surface modification device as discussed herein. Optionally, the host and guest materials can be pre-mixed prior to entry into the surface modification device. Pre-mixing can be performed in any suitable mixing device, such as a V-blender or the like. Pre-mixing can be used to achieve a more uniform mix of the host and guest materials. Pre-mixing may be beneficial for continuously operating dry coating devices, such as a Comil. In addition, pre-mixing can also allow for improved feeder performance in a continuous operation that is highly desirable for manufacturing productivity.

The host material and guest material may be provided to the surface modification device in varying amounts, depending on factors, such as the average particle size of the host and/or guest materials, the desired surface area coverage, and the like. In some embodiments, the amount of host material may range from about 95% to about 99.99%, based on the total weight of the mixture. In some embodiments, the amount of guest material may range from 0.01% to about 5%, based on the total weight of the mixture.

Optionally, in addition to the host and guest materials, other materials can be provided to the surface modification device, such as media particles like sugar beads, polymeric beads, or even magnetic or metallic beads that impart additional mixing and de-agglomerating forces to achieve better dry coating. Such particles are separated, for example, by sieving or other suitable means to separate these particles from the final dry coated excipient.

In most subsequent examples, unless otherwise stated, standard dry coating conditions used for MAIC, LabRAM, and comil are based on conditions that lead to proper silica coating. Operating conditions and coating effectiveness were chosen similar to what is described in L. J. Jallo, C. Ghoroi, L. Gurumurthy, U. Patel, R. N. Davé, "Improvement of flow and bulk density of pharmaceutical powders using surface modification," *International Journal of Pharmaceutics*, 423, 213-225 (2012), which is incorporated herein by reference. Standard process conditions are as follows, unless otherwise specifically noted in the Example section herein. One of ordinary skill in the art would be able to manipulate these conditions to achieve desired coating. For MAIC (magnetically assisted impaction coating), a constant magnet-to-sample ratio of 1:2 (e.g., about 0.5 grams of magnetic particles per 1 gram of total powders) and a constant field strength, controlled using a Variac 14V (AC) variable transformer, of about 12 mT were used. Magnetic particles used are made of barium ferrite coated with polyurethane and have irregular shapes and dimensions ranging from about 0.8 to about 1.4 mm Typical cylindrical jar of size about 250 ml was used and the processing time was about 10 minutes. For the LabRAM, the process intensity was set so that it was about 75 G at vibration frequency of about 60 Hz, and a cylindrical jar size of size about 300 ml was used and the processing time was 5 minutes. For comil, pre-blending was done using a V-blender, operated at about 25 rpm along with the I-bar at the rotating speed of about 3600 rpm for about 10 minutes. This pre-blend was fed using a screw feeder described herein at the feed rate of about 10 grams per minute in to a comil operated at the impeller speed of about 1300 rpm, using screen size about 457 microns.

Selection of Guest Particle Amount

The weight percent (wt %) of guest material described herein is in reference to a target of 100% surface area coverage (SAC) of the host particles with a monolayer of guest particles. While it is not always possible, for the sake of calculations, it was assumed that all guest particles were de-agglomerated and of the same size, that both host and guest particles were spherical, and that the host and guest particles would not deform during the dry coating process. Based on these assumptions, the weight percentage of guest particles for 100% surface coverage was calculated using Equations (1) and (2). These equations are most useful when the host particle size is taken as the volume to surface mean value; often described as D(3,2) instead of D50. D(3,2) is also called the Sauter mean diameter, defined as the diameter of a sphere that has the same volume/surface area ratio as a typical particle of interest. In the examples shown herein, most cases involve a cap of 1 wt %. For illustrative purpose, examples for various excipients are shown using two types of silica and for both cases of 1 wt % and equivalent to 100% SAC amounts. Although the examples employ those two levels, with some experimentation and based on the available particle contact models, those skilled in art could select the amounts in the range covered by these two levels, namely equivalent of 100% SAC and 1 wt %. In certain cases, lesser amounts may be used since it is expected that less guest material will have less adverse impact on tablet hardness. Table 3 shows under simplifying assumptions how much theoretical SAC may be achieved for several excipients when 1 wt % guest material is used. Table 3 also shows at what weight percent (wt %), 100% theoretical SAC could be achieved.

TABLE 3

| Host | D(3, 2) (μm) | Wt % of M5P for 100% SAC | Wt % of A200 for 100% SAC | Wt % of R972P for 100% SAC | Theoretical % of SAC by 1 wt % of A200 | Theoretical % of SAC by 1 wt % of M5P | Theoretical % of SAC by 1 wt % of R972P |
|---|---|---|---|---|---|---|---|
| Avicel ® 101 | 45 | 0.25 | 0.15 | 0.30 | 667 | 402 | 334 |
| Avicel ® 102 | 67 | 0.17 | 0.10 | 0.20 | 990 | 598 | 496 |
| Avicel ® 105 | 13 | 0.83 | 0.52 | 0.99 | 192 | 120 | 100 |
| Lactose 350 | 9 | 1.22 | 0.76 | 1.46 | 132 | 81 | 68 |
| Lactose 450 | 7 | 1.53 | 0.97 | 1.84 | 103 | 65 | 54 |
| Pharmatose ® DCL11 | 74 | 0.15 | 0.093 | 0.19 | 1079 | 647 | 537 |

Consider a fine excipient such as Avicel® 105 for which one could select a SAC lower than 100% to reduce the adverse impact on its compaction properties. For achieving 90% SAC of A200, the amount of A200 selected will be 0.468 wt %. However, in order to achieve a same 90% SAC of A200, the amount of A200 selected will be 0.09 wt % if the excipient were Avicel® 102. Likewise, for achieving 50% SAC using A200, the amount of A200 selected will be 0.255 wt % for Avicel® 105.

Compatibility of Guest-Host

For a given excipient, selection of a desirable guest material may vary depending on an objective. For example, a guest material may need to be hydrophobic, hydrophilic, or adjustable hydrophobicity. If the purpose is to alter wettability, the guest material may be selected accordingly. Host material-guest material compatibility can also be a selection factor. For example, an assessment based on surface energy could be made if a selected guest material does not spread on to the host surface. For this purpose, a spreading coefficient ($^{B/A}\lambda$) of guest material B on host material A has been proposed as shown in Equation (6).

$$^{B/A}\lambda = 4\left[\frac{^A\gamma_d{}^B\gamma_d}{^A\gamma_d + {^B\gamma_d}} + \frac{^A\gamma_p{}^B\gamma_p}{^A\gamma_p + {^B\gamma_p}} - \frac{^B\gamma_p + {^B\gamma_d}}{2}\right] \quad (6)$$

In Equation (3), $^A\gamma_d$ and $^B\gamma_d$ are dispersive components, and $^A\gamma_p$ and $^B\gamma_p$ are Lewis acid-base components of surface energy of the two materials. If the spreading coefficient is greater than or equal to 0, complete spreading of guest material B over host material A can be expected to occur. Another useful measure based on surface energy values of a host material and a guest material is given in equation (6) as an absolute difference in spreading coefficients (ΔSC).

$$\Delta SC = |^{B/A}\lambda - ^{A/B}\lambda| \quad (7)$$

If ΔSC>10, guest material B will spread on host material A. If ΔSC<5, spreading of guest material B can be poor, although it is possible that high intensity prolonged processing could provide sufficient spreading because of high compaction forces that result during the process. Such forces are both accounted for in the purely surface energy based assessment. If 5≤ΔSC≤10, spreading of guest material B can occur but will not be as good as for the case of ΔSC>10.

This selection strategy is utilized in some of the example disclosed herein. In some embodiments, A200 as a guest material can provide superior results to other silica materials.

Surface Modification Process Using Dry Coating

A variety of high intensity mixing devices could be used for surface modification. As exemplary illustrations, LabRAM and MAIC are used as batch devices, and comil is used as a continuously operating device. Through illustrative examples, their typical operating conditions are provided along with guidelines on how to optimize their operations. The examples reveal how such devices could provide comparable products.

LabRAM Device:

The LabRAM (Resodyne Corporation, USA) is a high-intensity vibrational bench top mixer employing a low frequency, high intensity vibration mode resulting in accelerations up to 100 times the force of gravity. This may lead to intense motion of powders including collisional actions which help in uniform mixing of the material within relatively short time. Due to the intense vibration of the process, guest particles disperse and adhere to the surface of the host particles creating a uniform layer. The vibration intensity and mixing time can be varied, by external digital controls. The automatic frequency of vibration is normally between 50-65 Hz. The acceleration and processing time are the primary parameters that control the coating process in the LabRAM. An example is provided to illustrate how this device could be optimized for dry coating performance. In addition, the fill-level of the jar may be varied so that the total powder placed occupies a height of about 30% to 99% of the available height. In some embodiment, the fill level is about 40% to 95%.

MAIC Device:

(Aveka, Inc, USA) Magnetically assisted impaction coating (MAIC) was used to coat the host materials with guest materials. The MAIC used in our experiments is a laboratory scale batch mode device that uses a circular electromagnet coil (7 cm ID, 6 cm height) to create an alternating magnetic field. This device has been used in previous publications, see for example, (Pfeffer, R., et al., Synthesis of engineered particulates with tailored properties using dry particle coating, Powder Technology, Vol. 117 1-2, Pages 40-67 (2010); Yang et al. 2005). Weighed amounts of pharmaceutical powders, nanoparticles and magnetic particles were loaded in a glass jar and then placed in the center of the coil. Upon exposure to electromagnetic field, the magnetic particles underwent rotational and translational motion, colliding with the powder, promoting mixing, and the shearing forces generated were expected to de-agglomerate the nanoparticles. All of these actions led to nanoparticles adhering to the surface of the pharmaceutical powders due to the van der Waals forces. A constant magnet-to-sample ratio of 1:2 (0.5 grams of magnetic particles per 1 gram of total powders) and a constant field strength, controlled using a Variac 14V (AC) variable transformer, of 12 mT were used for all experiments. Such conditions may be selected based on a limited optimization study and relying on the information available in the literature, see for example, Jallo et al., 2012. A cooling fan beneath the coil assisting in preventing the coil and the sample from overheating.

Comil Device:

An underdriven (model U3, Quadro Engineering, Waterloo, Ontario, Canada) Comil was used as an exemplary device for the process of surface modification of excipients through dry coating. The first suggested step in dry coating using the Comil is to pre-blend the pharmaceutical powder with the nanoparticles in ordinary low intensity mixer such as a V-blender (Patterson-Kelley, East Stroudsburg, Pa.). This is because doing so eliminates the need for continuously feeding silica nanoparticles into the Comil and assures proper weight ratios between the two constituents. The pre-blending step may also help with the feeder operation for the cohesive excipient powders. The powders were charged in the vessel of a V-blender and processed for 125 revolutions. Next, the pre-blended material was fed into the Comil using a screw feeder (M0D106M AccuRate, Schenck Process GmbH, Whitewater, Wis., USA), better representing the conditions in continuous manufacturing. Between the impeller and the screen, it is expected that large shearing forces are exerted onto the powder and the nanoparticles, creating enough force to deagglomerate the nanoparticles. Primarily through van der Waals forces, the nanosized silica subsequently would be attached to the surface of the excipient powders. After the powders flow through the screen, they are collected at the bottom of the milling chamber. The coating process can be repeated multiple times to impart further shear on the nanoparticles, break up particles, or to coat with multiple layers of guest particles. In this study, a round impeller, at a rotational speed of approximately 1,300 revolutions per minute, a screen with 457 microns round holes, and an inlet powder flow of 10 grams per minute were the processing conditions with the aim of de-agglomerating the nanoparticles as well as closely maintaining the pharmaceutical powder's primary particle size. These operating conditions were selected based on a limited design of experiment, to determine the conditions that provided good coating for a typical host-guest combination while preventing powder to build up (choking) within the Comil screen.

Fluid Energy Mill and Simultaneous Micronization and Dry Coating:

Simultaneous micronization and dry coating process involved two steps. First, a host material to be milled was pre-mixed with an amount of guest material in a v-shaped blender The resulting mixture was then milled in a fluid energy mill (FEM; Q Micronizer qualification model 1"; Sturtevant Inc., Hanover, Mass.). The method has been previously reported by Han, et al., "Simultaneous micronization and surface modification for improvement of flow and dissolution of drug particles," *International Journal of Pharmaceutics*, 415, 185-195 (2011), the entirety of which is incorporated herein by reference. The pre-mixing was done in a 4 quart V-shaped blender (Patterson-Kelley, PA, USA) with the intensifier bar. The V-blender was operated at 25 rpm with the intensifier bar rotating at 3600 rpm for 10 minutes. This pre-mix was then introduced in to the FEM using a screw feeder (M0D106M AccuRate, Schenck Process GmbH, Whitewater, Wis., USA). FEM operation was set by adjusting the feed rate, feed pressure and grinding pressure.

Blends Using Dry Coated Excipients

A blend as provided herein may be used to form a pharmaceutical tablet. The blend preferably has sufficient flowability, bulk density, and tabletability properties to form a pharmaceutical tablet.

The blend includes an API and the dry coated excipient. The API may be hydrophilic or hydrophobic, have good or poor flowability, bulk density and tabletability. The API may have a flowability expressed as FFC ranging from about 0.5 to 12.0. In some embodiments, the flowability in terms of FFC may be 1.0 to 6.0. The API may have a bulk density ranging from 0.1 g/mL to 0.8 g/mL. In some embodiments, the bulk density may be 0.15 g/mL to 0.5 g/.

Exemplary API may include one or more of ascorbic acid, ibuprofen, metformin, acetaminophen, micronized acetaminophen (mAPAP), cetirizine, indeloxazine, ondansetron, artemether, niflumic acid, diclofenac, medications for acute pain and other non-steroidal anti-inflammatory drugs. In some embodiments, the API is a cohesive API. In some embodiments, a cohesive API is an uncoated API. In some embodiments, a cohesive API has a bulk density ranging from about 0.05 g/mL to 0.5 g/mL. In some embodiments, a cohesive API has and an flow function coefficient (FFC) ranging from about 1.0 to 3.5.

The API may be present in the blend at a loading amount ranging from 0.1 wt % to 95 wt %, based on the total weight of the blend. In some embodiments, the loading amount ranges from 20 wt % to 99 wt %. In some embodiments, the loading amount ranges from 20 wt % to 60 wt %. In some embodiments, the loading amount ranges from 5 wt % to 70 wt %. Blends at low API loadings, such as 0.1 wt % to 5 wt %, by weight may have different behavior as compared to those at high drug loadings, such as 20 wt % to 70 wt % by weight. The purpose of the excipient may also differ and so would be the route for forming tablets. However, in general, it is desirable to have blends that flow well.

The dry coated excipient can be included in the blend to improve on the properties of the API such that it can be formed into a pharmaceutical tablet. In some embodiments, the tablet can be formed preferably using direct compression without need for granulation. In some embodiments, granulation cannot be avoided but may be in form of dry granulation such as roller compaction. In other embodiments, wet granulation may be necessary. The purpose of the dry coated excipient is to promote wider use of direct compression or dry granulation at high drug loadings. The dry coated excipient may be present in the blend in an amount ranging from 1 wt % to 99 wt %, based on the total weight of the blend. In some embodiments, the amount ranges from 5 wt % to 90 wt %. In some embodiments, the amount ranges from 25 wt % to 90 wt %. When present in the lower range such as 5 wt % to 25 wt %, it would be desirable if it can promote dry granulation instead of wet granulation. If present in the higher range such as it is greater than 30 wt %, it would be desirable if it promotes direct compression instead of granulation.

The blend may include one or more additives. For instance, additives may be included to affect the desired release profile of the API, or affect other blend and/or tablet properties. Additives may include one or more of disintegrants, lubricants, glidants, matrix formers, and others. Exemplary disintegrants may include crospovidine, sodium starch glycolate, croscarmellose sodium, etc. Exemplary lubricants may include magnesium stearate (MgSt), stearic acid, etc. The glidants may be various types of solica, titania, talc, etc. The matrix formers can be HPMC, starches, alginates, etc. The additive may be present in the blend in an amount ranging from 0.01 wt % to 30%, based on the total weight of the blend. In some embodiments, the amount ranges from 0.1 wt % to 5 wt %.

Flowability of the blend expressed in FFC may range from about 1 to about 30. In some embodiments, the FFC ranges from about 2 to about 30.

Bulk density of the dry coated excipients may range from about 0.2 g/mL to about 0.99 g/mL.

A blend may be prepared by mixing desired amounts of the excipient, API, and optionally one or more additives. For example, in some embodiments, the blends can be prepared by mixing at about 25 rpm for about 12 minutes in a 4 quart V blender (Patterson-Kelley, USA). Other mixing speeds and times can be used. To make a tablet, the blend may be compacted under pressure in a die. For example, in some embodiments, a tablet was prepared using Carver platen press (Carver, Inc., USA) under a compaction pressure ranging from about 30 to about 200 MPa using 500 mg of the blend. The blend was placed in a 0.5 inch inner diameter stainless die with flat-faced round punch.

Tensile strength of a 0.5 inch inner diameter tablet of the blend, made by the method described above, may range from about 1 MPa to about 10 MPa. In some embodiments, the tablet has a porosity ranging from about 0.05 to about 0.35.

Example 1

Example 1 determines the absolute difference in spreading coefficient ($\Delta SC$) for several exemplary host materials and guest materials. Further, dry coated excipients are made using these materials and the experimental results are compared with the theoretical calculations. Surface energy was measured using an automated inverse gas chromatograph (surface energy analyzer, SEA, Surface Measurement Systems Ltd., Middlesex, UK). This device and the measurement procedure have been described in detail in Han, X., et al., "Passivation of high surface energy sites of milled ibuprofen crystals via dry coating," Journal of Pharmaceutical Sciences, Vol. 102(7), 1-15 (2013). The Lifshitz-van der Waals (LW) dispersive surface energy (e.g., the dispersive components of Equation (6)) was calculated based on the Schultz method with five alkane probes (hexane, heptane, octane, nonane, and decane) (Lavielle, et al., The Role of the Interface in Carbon Fibre-Epoxy Composites. The Journal of Adhesion 23, 45-60 (1987)). The Lewis acid-base polar surface energy was calculated based on the Good-van Oss method with data from two polar probes (dichloromethane and ethyl acetate) (Van Oss, et al., Additive and non-additive surface tension components and the interpretation of contact angles. Langmuir 4, 884-891 (1988)). All measurements were performed at infinite dilution, i.e., at 3% surface area coverage. For all surface energy experiments, the samples were packed in a straight silanized glass column (4 mm ID, 30 cm long) using a tapping unit, also from SMS. The samples were then conditioned to remove impurities and moisture using the carrier gas (helium). The experimental conditions were as follows: carrier gas (helium) flow rate 10 ml/min; column temperature 303 K; detector and Injector temperature 453 K. Column conditioned for 120 minutes at 0% RH and 303 K before the probes were injected. Methane was used for dead volume corrections. The results for these measurements for the host materials and guest materials are shown in Table 4. ΔSC was mostly above 10, and, in some cases, above 5. There were two cases where ΔSC was below 5, potentially suggesting poor coating quality would be realized. In those cases, the host materials were Avicel® 101 and Lactose 350, and the guest material was M5P, a hydrophilic silica.

TABLE 4

| | LW dispersive surface energy | LW dispersive surface energy | Difference in spreading coefficient (ΔSC) | |
|---|---|---|---|---|
| | $\gamma_d$ (mJ/m²) | $\gamma_p$ (mJ/m²) | M5P | R972P |
| Host | | | | |
| Avicel ® 101 | 42.33 | 4.93 | 1.56 | 14.26 |
| Avicel ® 102 | 56.05 | 8.97 | 33.97 | 50.44 |
| Avicel ® 105 | 47.80 | 6.50 | 12.52 | 28.34 |
| Lactose 350 | 41.82 | 7.54 | 2.64 | 19.22 |
| Lactose 450 | 44.69 | 7.17 | 7.64 | 24.22 |
| Pharmatose ® DCL11 | 39.48 | 4.85 | 7.42 | 9.16 |
| Guest | | | | |
| M5P | 44.68 | 3.36 | | |
| R972P | 34 | 5.75 | | |

Avicel® 101 and Lactose 350 were used as guest materials and M5P and R972P were used as guest material to experimentally confirm ΔSC predictions from Table 4. Four dry coated excipients as shown in Table 5.

TABLE 5

| Example | Host | Guest (wt %) | Process |
|---|---|---|---|
| Ex 1.1 | Avicel ® 101 | M5P (1%) | Comil |
| Ex 1.2 | Avicel ® 101 | R972P (1%) | |
| Ex 1.3 | Lactose 350 | M5P (1%) | |
| Ex 1.4 | Lactose 350 | R972P (1%) | |

In Example 1.1 through 1.4 about 1 wt % of a guest material was added based on the weight of the host material. The dry coated excipients of Examples 1.1 through 1.4 were experimentally prepared using the Comil device with the operating conditions discussed herein. The pre-blended powders were fed into the comil (model U3, Quadro Engineering, Waterloo, Ontario, Canada) at a rotational speed of 1300 revolutions per minutes using a screen with 457 μm round holes, and the feed rate of pre-blended powder is 10 gram per minute. SEM micrographs of the resulting dry coated excipients are depicted in FIGS. 4a-d, respectively, for Examples 1.1 to 1.4. SEM imaging was done using a LEO 1530 VP Field Emission Scanning Electron Microscope equipped with an Oxford UTW X-ray detector was used. The beam energy varied in the range 1-3 kV for different samples. A thin coating of electrically conducting carbon is first deposited by a Bal-TEC 020 HR Sputtering Coater onto the sample. Coating of the samples prevents the accumulation of static electric fields, common for many pharmaceutical powders, and improves the contrast. As shown in FIG. 4, dry coating is achieved for both Avicel® 101 and Lactose 350 using both types of guest materials. However, as predicted by ΔSC in Table 4, better surface coverage is achieved with R972P, a hydrophobic silica.

Example 2

Example 2 demonstrates a general trend of a multi-asperity adhesion force model and its validation using an API as a host material.
Multi-Asperity Contact Model to Predict Reduced Cohesion Upon Dry Coating As disclosed in Chen et al., 2008 (referenced above), for a typical single asperity model such as the Rumpf model, the amount of guest material does not matter since the analysis is based on a single guest between two host materials. However, in reality, there are three contact forms, namely host-host, host-guest, and guest-guest during a contact between original particles in the presence of nano-sized guest particles. When there are few guest particles, the majority of particle contacts are host-host, and the interparticle forces are the greatest and are calculated by Equation (5), which is a simplified version of Rumpf's equation. When there is a sparse, but uniform, guest coating, host-guest contact becomes the dominant particle interaction, where the interparticle force is calculated by Equation (6). The transition from host-host to host-guest contact occurs at very low guest amounts, typically when SAC is approaching to about a value under 1%. When there is a dense coating of nanoparticles, a guest-guest contact is the dominant interaction. The transitional SAC from host-guest to guest-guest particle interaction may be of the order of about 30% for fine spherical host particles with typical nano-silica coating. For that case, Equation (10) is used to calculate the interparticle force, but the Hamaker constant is based on the coating material instead of the host material as in Equation (8).

$$F_{ad} = \frac{A}{12} \frac{D}{2} \frac{1}{z_0^2} \quad (8)$$

$$F_{ad} = \frac{Ad}{4z_0^2} + \frac{A}{24\left(\sqrt{\left(1+\frac{d}{D}\right)^2 - \frac{1.21}{SAC}\left(\frac{d}{D}\right)^2} - 1\right)^2 D} \quad (9)$$

$$F_{ad} = \frac{Ad}{24z_0^2} \quad (10)$$

In the above equations, A is the Hamaker constant (material property, a function of surface energy), d is the particle size of guest particle, $z_0$ is the minimum separation distance between two particles, typical value being 0.4 nm, and D is either the diameter (for a smooth particle) of host particle or the natural surface roughness (for rough particles, typically estimated to be about 200 nm). Since $F_{ad}$ may be computed from above equations, the granular Bing number, $Bo_g$ can also be computed from a simple relationship presented in Equation (11), where m is the mass of the particle and g is the acceleration due to gravity on earth.

$$Bo_g = \frac{F_{ad}}{mg}. \quad (11)$$

It is generally considered that the high Bond numbers, $Bo_g$ indicate poor flow due to high cohesion force as compared to particles own weight (or gravity force).

TABLE 6

| Example | Host | Guest (wt %) | SAC (%) | Process |
|---|---|---|---|---|
| Ex 2.1 | mIBU | 0 | 0 | FEM based |
| Ex 2.2 | D(3, 2) = 13.4 | 0.054 | 5 | milling followed |
| Ex 2.3 | microns | 0.108 | 10 | by dry coating |
| Ex 2.4 | | 0.324 | 30 | using LabRAM |
| Ex 2.5 | | 0.54 | 50 | |
| Ex 2.6 | | 0.81 | 75 | |
| Ex 2.7 | | 1.08 | 100 | |

In Examples 2.1 through 2.7 mIBU was used as a host material, which was milled using a Fluid Energy Mill, as described herein, down to D(3,2)=13.4 microns, using Ibuprofen 50 as a starting material (BASF, Tarrytown, N.Y., USA), having median particle size (D50) is 58 microns. In this example, the fluid energy mill was used to mill the host material only, i.e., no guest material was added. The dry coating material was amorphous hydrophilic nanosilica, M5-P, which is pharmaceutical grade (Cabot Corporation, Billerica, Mass.) and was used as a guest material. Examples 2.1 through 2.7 were made by added an amount of the guest material as shown in Table 1 to achieve a SAC ranging from 0% to 100%. The dry coated APIs were made using the LabRAM as described herein. Bulk density, porosity, and unconfined yield strength (UYS) of each Example was determined as described herein.

Figure 5A:
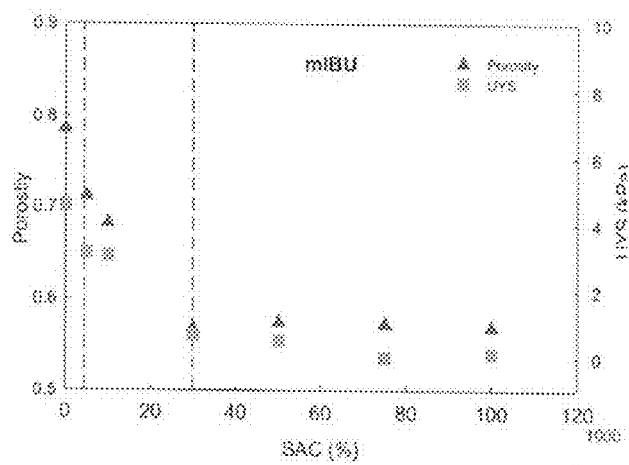
FIGS. 5a-b are, respectively, plots of porosity as a function of surface area coverage (SAC) and adhesion force as a function of SAC.
Figure 5B:
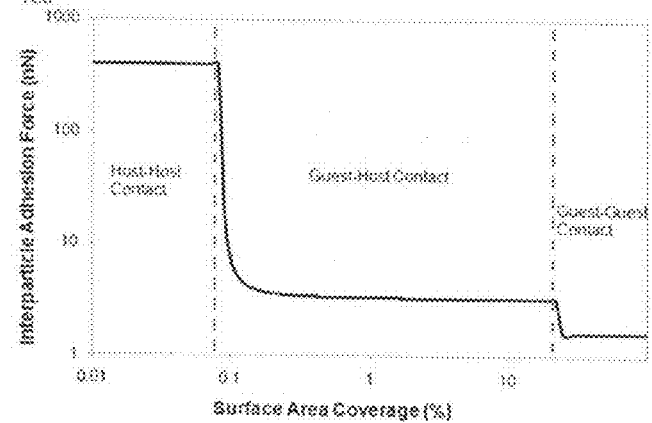

It is expected that $F_{ad}$ would reduce as SAC was increased, resulting in better packing, i.e., reduced porosity and reduced unconfined yield strength (UYS). As shown in FIG. 5a, as SAC increases from 0 to 100%, porosity and UYS are reduced, transitioning between three different regimes, where vertical dashed lines mark the transition between regimes. The regimes transition from host-host to host-guest to guest-guest contacts with increasing SAC. In FIG. 5b, the contact force model of Equations (5)-(7) is applied to an idealized host particle of about 15 microns in size dry coated with nano-silica in varying SAC amounts. The adhesion force rapidly decreases as a function of increasing SAC from the host-host contact to host-guest contact regime. At above 100% SAC, the adhesion force further decreases. The trends in adhesion force depicted for the idealized host particle of FIG. 5b are qualitatively similar to the experimental results in FIG. 5a. This comparison demonstrates the model is valid and dry coating can result in contact force reduction by over one order of magnitude. This would imply that the granular Bond number would also reduce by about one or two orders of magnitude and that indicates improved packing and flow properties as seen in the left figure.

Example 3

Example 3 shows a method of using bulk density to optimize LabRAM. The method could be extended to any dry coating device. Example 3 also shows how devices such as MAIC and LabRAM could be used as material sparing baseline dry coaters. The following dry coated excipients using Lactose 450 the host material, and R972P or M5P as the guest material were prepared as shown in Table 7.

TABLE 7

| Example | Host | Guest (1 wt %) | Process |
|---|---|---|---|
| Ex 3.1 | Lactose 450 | — | — |
| Ex 3.2 | | R972P | MAIC |
| Ex 3.3 | | M5P | |
| Ex 3.4 | | R972P | LabRAM (50%) |

TABLE 7-continued

| Example | Host | Guest (1 wt %) | Process |
|---|---|---|---|
| Ex 3.5 | | M5P | |
| Ex 3.6 | | R972P | LabRAM (70%) |
| Ex 3.7 | | M5P | |
| Ex 3.8 | | R972P | LabRAM (80%) |
| Ex 3.9 | | M5P | |
| Ex 3.10 | | R972P | LabRAM (90%) |
| Ex 3.11 | | M5P | |

Figure 6:
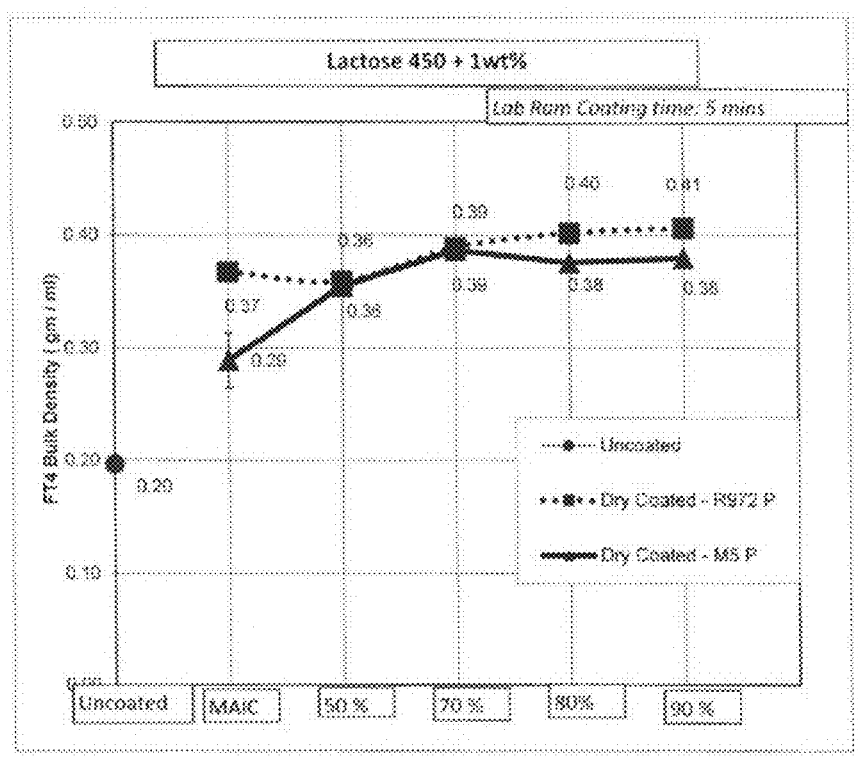
FIG. 6 depicts bulk density of several dry coated and uncoated excipients under various process conditions.
Figure 7A:
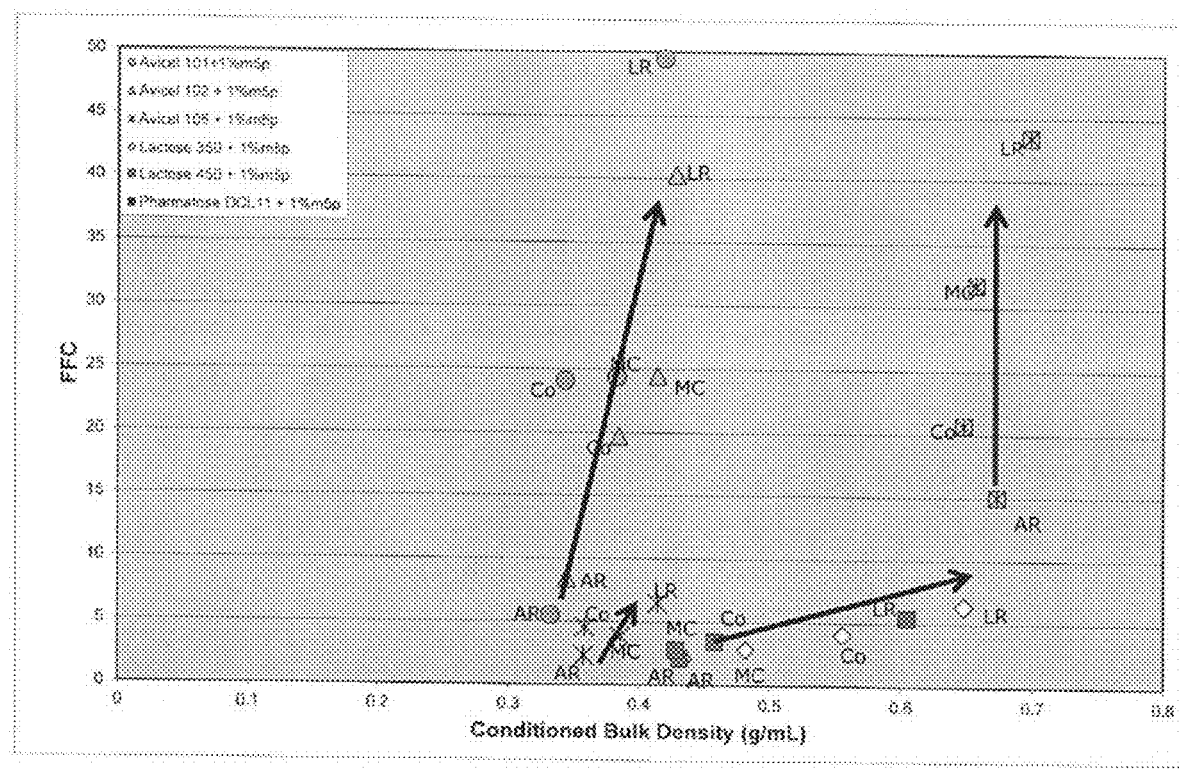
FIGS. 7a-d are, respectively, phase maps of uncoated and dry coated excipients under various process conditions at 1 wt % M5P, 100% SAC M5P, 1 wt % R972P, and 100% SAC R972P.
Figure 7B:
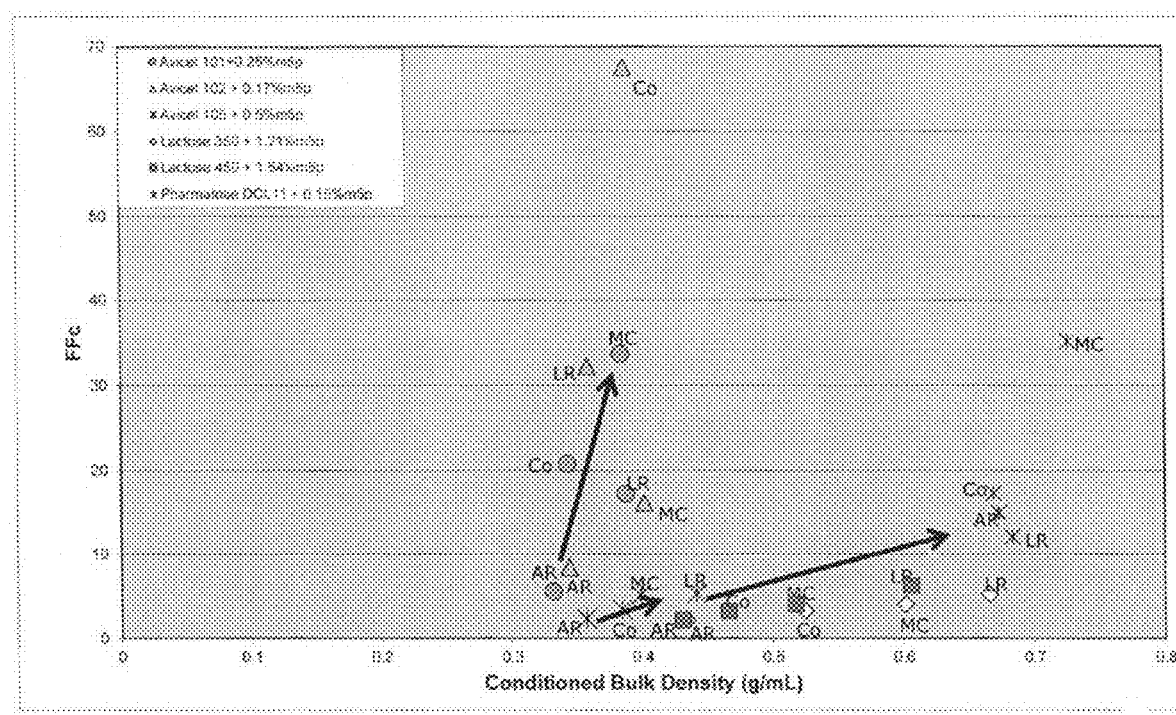
Figure 7C:
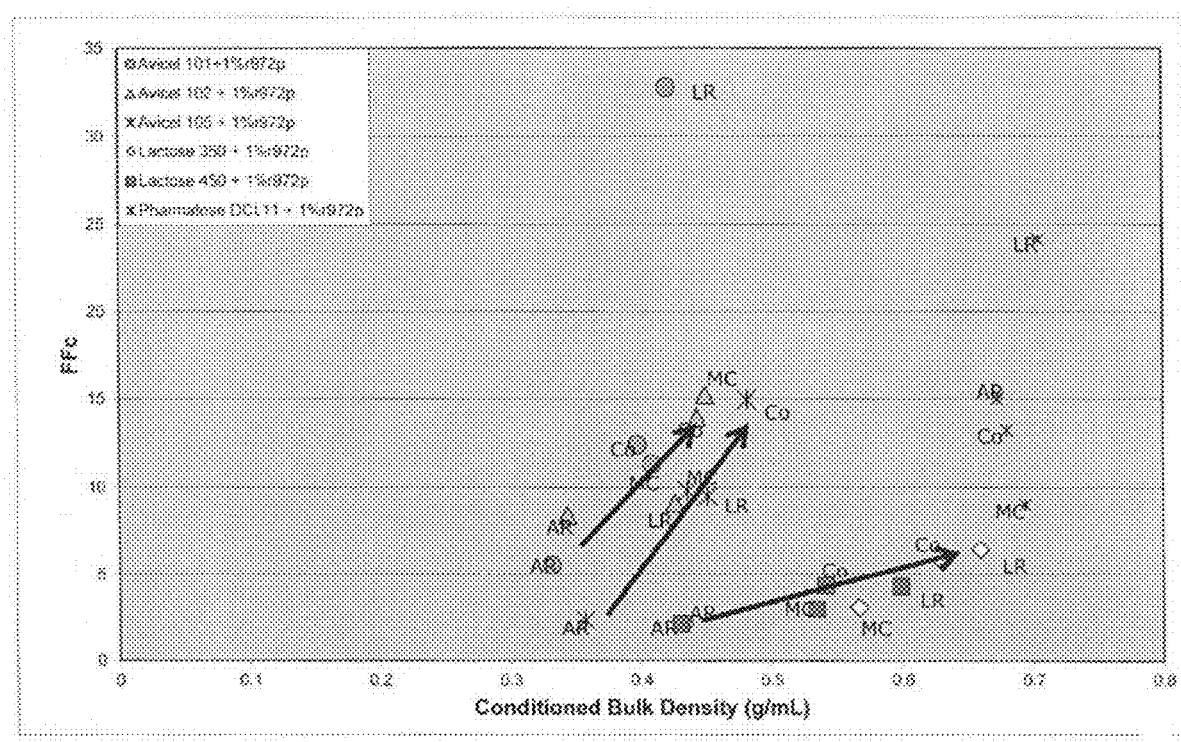
Figure 7D:
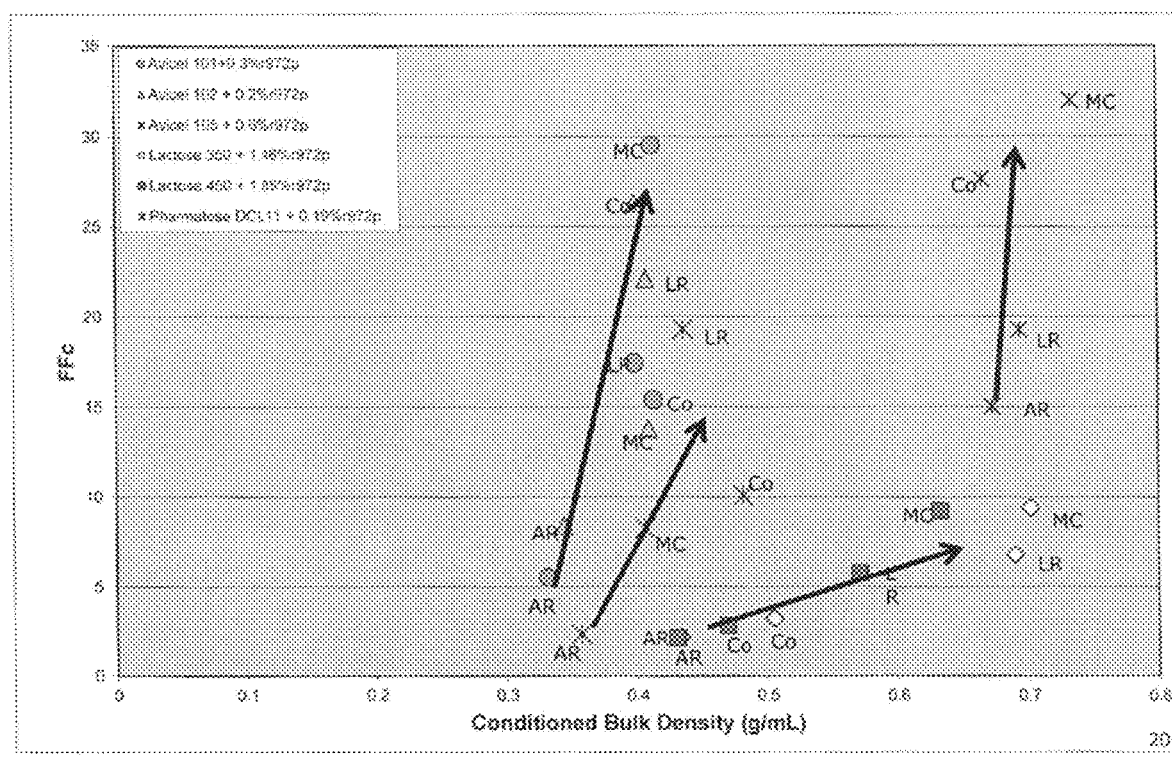

The dry coated excipients of Examples 3.1 through 3.11 were prepared as shown in Table 7 by adding about 1 wt % of the guest material based on the weight of the host material. The dry coated excipients were prepared using MAIC with conditions described herein, and LabRAM by varying process intensity values (about 50% to about 90%) at fixed process time of about 5 minutes. The fill levels were fixed in all cases, although a full-factor design of experiments (DoE) could be carried out to study all critical factors such as the process intensity, fill level, and processing time. In separate tests (not shown), it was found that the impact of fill-level was not very significant. The bulk density of each data point was measured as discussed herein. As shown in FIG. 6, the bulk density of the as received host material is low (about 0.2 g/mL), and increases with dry coating of the guest material.

As Table 4 indicates based on ΔSC, R972P should generally be a more effective guest material for Lactose 450. This result is confirmed by improved bulk density using MAIC, where FIG. 6 shows values of 0.29 and 0.37 g/ml, respectively, using M5P and R972P as guest materials. LabRAM, being a higher intensity device than MAIC, is expected to be less sensitive to the predictions based on Equation (4). FIG. 6 shows increases in bulk density for both guest particles when LabRAM is used. For M5P, 70% intensity for LabRAM is optimal. For R972P, higher intensity of LabRAM (i.e., greater than 70%) results in a bulk density nearly double that of MAIC.

Example 4

Example 4 determines the bulk density and FFC of several dry coated excipients using different dry coating devices using M5P and R972P, respectively, as guest materials and at 1 wt % and 100% SAC. The experimental examples used in Example 4 are shown in Table 8.

TABLE 8

| Example | Host | Guest | Guest (wt %) | Guest (wt % or % SAC) | Process |
|---|---|---|---|---|---|
| Ex 4.1a-c | Avicel ® 101 | M5P | 1 | 1 wt % | (a) MAIC |
| Ex 4.2a-c | Avicel ®102 | | | | (b) Comil |
| Ex 4.3a-c | Avicel ® 105 | | | | (c) |
| Ex 4.4a-c | Lactose 350 | | | | LabRAM |
| Ex 4.5a-c | Lactose 450 | | | | |
| Ex 4.6a-c | Pharmatose ® DCL11 | | | | |
| Ex 4.7a-c | Avicel ® 101 | M5P | 0.25 | 100% SAC | (a) MAIC |
| Ex 4.8a-c | Avicel ® 102 | | 0.17 | | (b) Comil |
| Ex 4.9a-c | Avicel ® 105 | | 0.5 | | (c) |
| Ex 4.10a-c | Lactose 350 | | 1.21 | | LabRAM |
| Ex 4.11a-c | Lactose 450 | | 1.54 | | |
| Ex 4.12a-c | Pharmatose ® DCL11 | | 0.15 | | |
| Ex 4.13a-c | Avicel ® 101 | R972P | 1 | 1 wt % | (a) MAIC |

TABLE 8-continued

| Example | Host | Guest | Guest (wt %) | Guest (wt % or % SAC) | Process |
|---|---|---|---|---|---|
| Ex 4.14a-c | Avicel ® 102 | | | | (b) Comil |
| Ex 4.15a-c | Avicel ® 105 | | | | (c) |
| Ex 4.16a-c | Lactose 350 | | | | LabRAM |
| Ex 4.17a-c | Lactose 450 | | | | |
| Ex 4.18a-c | Pharmatose ® DCL11 | | | | |
| Ex 4.19a-c | Avicel ® 101 | R972P | 0.3 | 100% SAC | (a) MAIC |
| Ex 4.20a-c | Avicel ® 102 | | 0.2 | | (b) Comil |
| Ex 4.21a-c | Avicel ® 105 | | 0.6 | | (c) |
| Ex 4.22a-c | Lactose 350 | | 1.46 | | LabRAM |
| Ex 4.23a-c | Lactose 450 | | 1.85 | | |
| Ex 4.24a-c | Pharmatose ® DCL11 | | 0.19 | | |

The experimental examples were made by adding the appropriate amount of guest material to achieve 1 wt % (relative to host material) or 100% SAC under the process conditions for MAIC, Comil and LabRAM shown in Table 8. The operation conditions are the standard conditions discussed in the methods section. Generally, the coating quality of each sample behaved as predicted by Equation (4). SEM micrographs (not shown) indicated coating of guest material is evident. Even when the excipient is a granule, such as for Pharmatose® DCL11, dry coating of guest material is good and visible on the surface without appreciable agglomeration of the guest material.

FIGS. 7a-d depict 2-D phase maps of FFC and bulk density for the as received and dry coated excipients listed in Table 8. The points in FIGS. 7a-d are labeled as received material (AR), and dry coated excipient using three different devices, Comil (Co), LabRAM (LR), and MAIC (MC). FIGS. 7a-d, respectively, depict 2-D phase maps for 1 wt % M5P, 100% SAC M5p, 1 wt % R972P, and 100% SAC R972P. The results generally follow predictions based on Equations (4)-(7). FFC can be interpreted as not flowing for FFC<1, very cohesive for 1<FFC<2, cohesive for 2<FFC<4, easy flowing for 4<FFC<10, and free-flowing for FFC>10.

Figure 8:
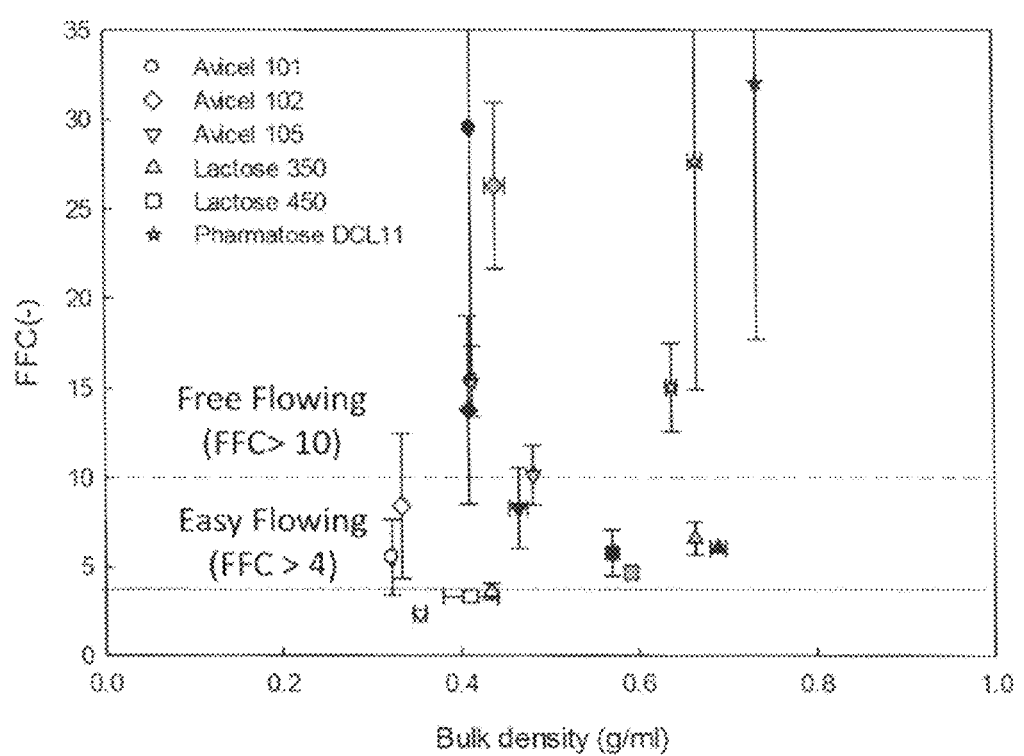
FIG. 8 shows a phase map comparing dry coated excipients at 100% SAC prepared by a batch coating device MAIC and continuous double pass coating.

FIG. 8 depicts a summary phase map that compares as received excipients (white symbol) with dry coated excipients made using MAIC (black symbol) and Comil (gray symbol). Unlike FIGS. 8a-d, which depicts average values, error bars are provided in FIG. 8 for bulk density and FFC. As shown in FIG. 8, the extent of variation is low for bulk density but more significant for FFC, as it increases beyond free flowing limit of 10. Two horizontal dashed lines demark easy flow and free flow regions in FIG. 8. As received Avicel® 105, Lactose 350, and Lactose 450 are not easy flowing, i.e., FFC<4, hence not easy flowing. However, upon dry coating at 100% SAC with R972P using Comil, Lactose 350 and 450 become easy flowing, i.e., FFC>4, and Avicel® 105 becomes nearly free-flowing, i.e., FFC>10. Bulk density enhancements are also very significant for these excipients, with largest gain for Lactose 350, followed by Lactose 450, and then Avicel® 105. It is noted that Comil need to be properly optimized in order to achieve such remarkable improvements in only 2 passes as compared to many passes as reported in Chattoraj et al., 2011, and Zhou et al., 2012 (referenced above).

The remaining excipients, Avicel® 101, Avicel® 102, and Pharmatose® DCL11 attain free flow nature, where FFC<10. Due to the nature of FFC computation, once FFC is above about 12, the differences are not indicative because all free flowing powders, which also part explains large error bars at FFC above about 12. In cases of high FFC, the bulk density, and more importantly, the packing fraction that could be estimated from bulk density and other material properties, can be a more discerning indicator of property improvement. In FIG. 8, the bulk density for Lactose 350 and Lactose 450 are most significant in terms of percentage increase compared to as received material, followed by Avicel® grades, and then Pharmatose® DCL11, which has a very high bulk density to begin with due to spherical shape in contrast to irregular fibrous nature of Avicel® grades. The data for some dry coated excipients is also summarized in Table 5 compared to Prosolv® 90 HD, which also include particle sizes; D10, D50, and D90.

TABLE 9

| Example | D10 (μm) | D50 (μm) | D90 (μm) | Bulk Density (g/mL) | FFC |
|---|---|---|---|---|---|
| Prosolv ® | 20.4 | 93.8 | 236.9 | 0.5 | 14.6 |
| Ex 4.1c | 22 | 66 | 164 | 0.4 | 17.24 |
| Ex 4.13c | 22 | 66 | 164 | 0.43 | 20.4 |
| Ex 4.2c | 32 | 122 | 244 | 0.45 | 32.23 |
| Ex 4.14c | 32 | 122 | 244 | 0.42 | 13.5 |
| Ex 4.3c | 7 | 19 | 40 | 0.45 | 5.34 |
| Ex 4.15c | 7 | 19 | 40 | 0.47 | 21.6 |
| Ex 4.4c | 3 | 26 | 78 | 0.67 | 5.22 |
| Ex 4.16c | 3 | 26 | 78 | 0.69 | 6.83 |
| Ex 4.5c | 3 | 17 | 48 | 0.61 | 6.24 |
| Ex 4.17c | 3 | 17 | 48 | 0.63 | 9.24 |
| Ex 4.6c | 43 | 112 | 205 | 0.68 | 12.1 |
| Ex 4.18c | 43 | 112 | 205 | 0.69 | 19.3 |

Example 4 demonstrates that dry coated excipients are an improvement over as received excipients in terms of flowability and bulk density. However, Example 4 does not determine the effects of dry coated excipients on compaction properties, which is discussed in Example 5.

In next set of examples, compaction results for individual excipients before and after dry coating are presented. While these were conducted for many different types of excipients, the examples will illustrate the behavior through three grades of Avicel®, which are of great interest to industry for several reasons. In subsequent work, another type of hydrophilic silica is used because of its potential for superior performance. Accordingly, instead of silica M5P, grade A200, hydrophilic silica from Degussa/Evonik Corporation is used.

Example 5

Figure 9:
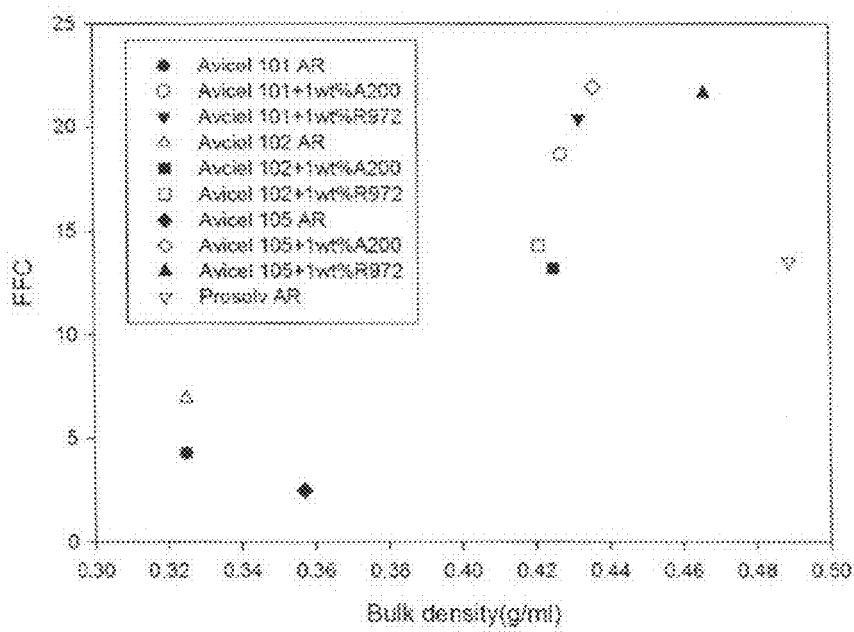
FIG. 9 is a plot of FFC and bulk density uncoated and dry coated excipients.
Figure 10A:
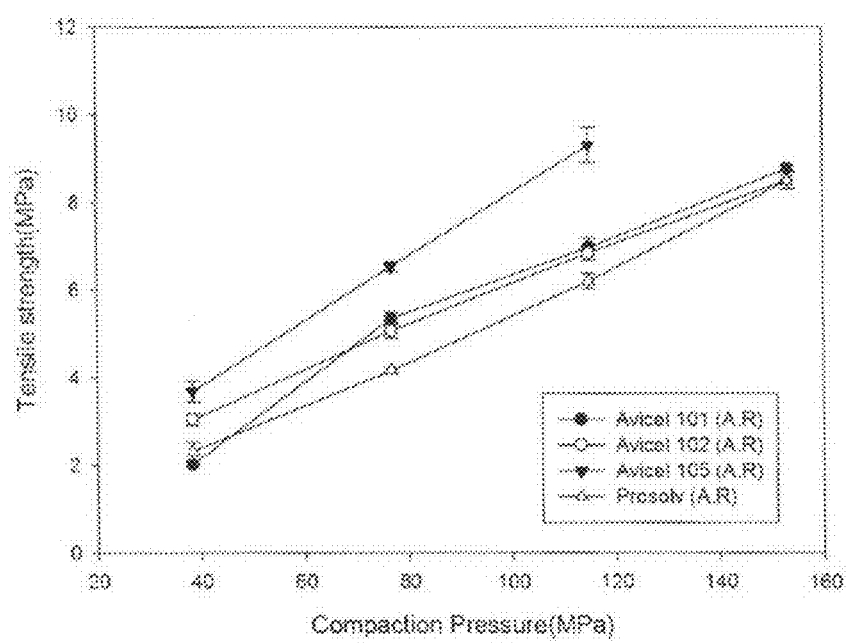
FIG. 10a-d are, respectively, plots of tensile strength as a function of compaction pressure for tablets made from as received excipients, dry coated Avicel® 105 excipients, dry coated Avicel® 101 excipients, and dry coated Avicel® 102 excipients, in comparison to Prosolv® 90 HD.
Figure 10B:
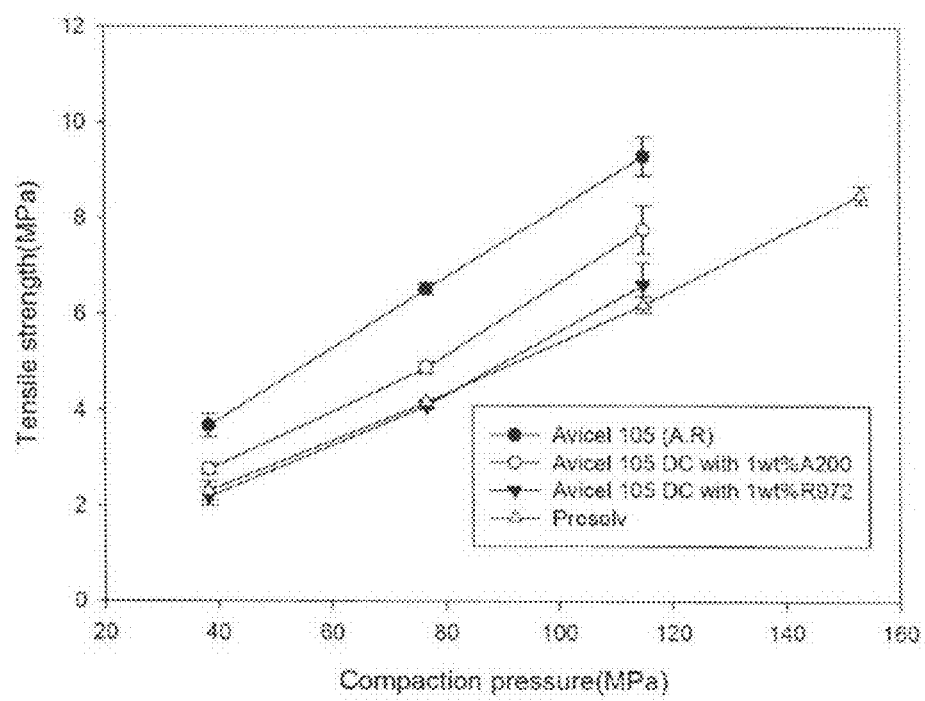
Figure 10C:
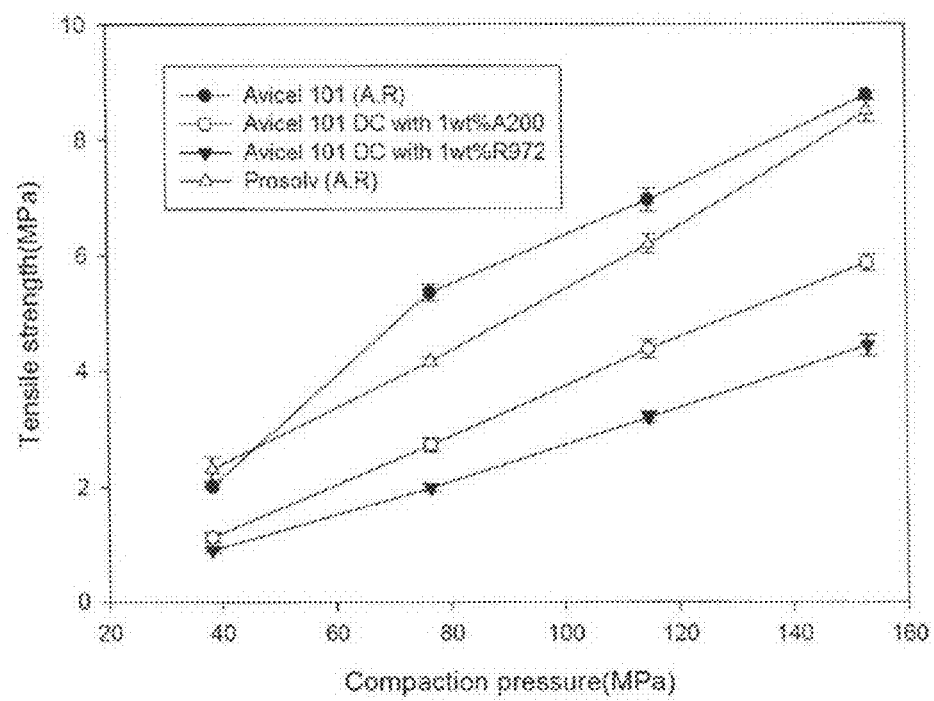
Figure 10D:
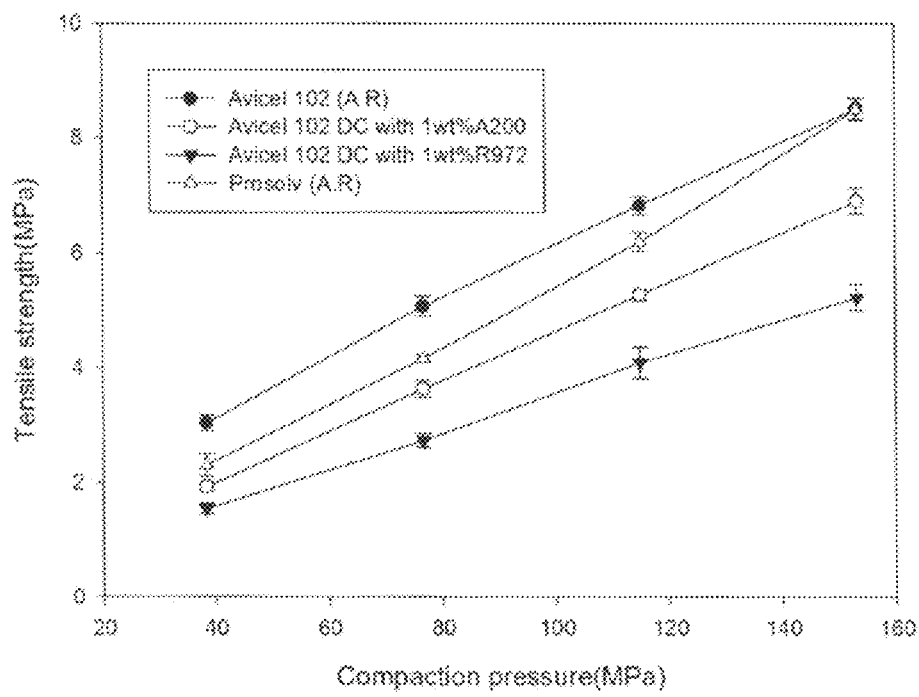

The previous example showed that even the finest grade Avicel®, i.e., Avicel® 105, had significant flow improvement after dry coating. However, although the hydrophilic silica M5P achieved easy flow category, it did not reach free flow category after dry coating for finer grade excipients such as Avicel® 105, Lactose 350 or Lactose 450. Another guest host, A200 (Degussa/Evonik Corporation) which is hydrophobic is used in place of M5P. The adhesion force predicted by Equations (5) through (7) suggests smaller particle size of A200 compared to that of M5P would be more effective. When compared with R972P, it was found that A200 can almost match R972P, which is summarized in Table 6 where all dry coated materials are free flowing powders, where FFC>10. These FFC values are average of three or more trials and dry coating was done using LabRAM under conditions similar to previous examples. A 2-D phase plot of bulk density and FFC is depicted in FIG. 9, along with commercially available MCC based specialty excipient, PROSOLV® SMCC ("Prosolv® 90 HD") as a comparison. The dry coated excipients have FFC about the same or higher than Prosolv® 90 HD. Expectedly, Prosolv® 90HD has higher bulk density being spherical and larger in size than the Avicel® grades. Nonetheless, dry coated Avicel® grades have significant improvement in bulk density compared to as received material.

TABLE 10

| Example | Material | Bulk Density (mg/mL) | FFC |
|---|---|---|---|
| 5.1 | Avicel® 101 A.R. | 0.33 | 4.3 |
| 5.2 | Avicel® 101 + 1 wt % A200 | 0.43 | 18.7 |
| 5.3 | Avicel® 101 + 1 wt % R972 | 0.43 | 20.4 |
| 5.4 | Avicel® 102 A.R. | 0.33 | 6.95 |
| 5.5 | Avicel® 102 + 1 wt % A200 | 0.43 | 12.6 |
| 5.6 | Avicel® 102 + 1 wt % R972 | 0.42 | 13.5 |
| 5.7 | Avicel® 105 A.R. | 0.36 | 2.49 |
| 5.8 | Avicel® 105 + 1 wt % A200 | 0.44 | 21.9 |
| 5.9 | Avicel® 105 + 1 wt % R972 | 0.47 | 21.6 |

Example 6

Example 6 demonstrates tablet compaction of as received and dry coated excipients. Prosolv® is again used for comparison. The suitability of an excipient intended for a tablet dosage form can be evaluated by its tabletability, compressibility, and compactability. Tabletability, i.e., tablet tensile strength as a function of compaction pressure, is the capability of a powder to gain strength under pressure, and useful to evaluate manufacturability. Within the context of the BABS model by Sun 2011 (referenced above), compressibility and compactability, respectively, assess bonding area and bonding strength. Compressibility, i.e., tablet solid fraction as a function of compaction pressure, evaluates decrease in porosity which corresponds to increase in bonding area due to particle rearrangement, fragmentation, and deformation. Compactability, i.e., tablet tensile strength as a function of tablet solid fraction, evaluates relative bonding strength between various materials and formulations.

Figure 11A:
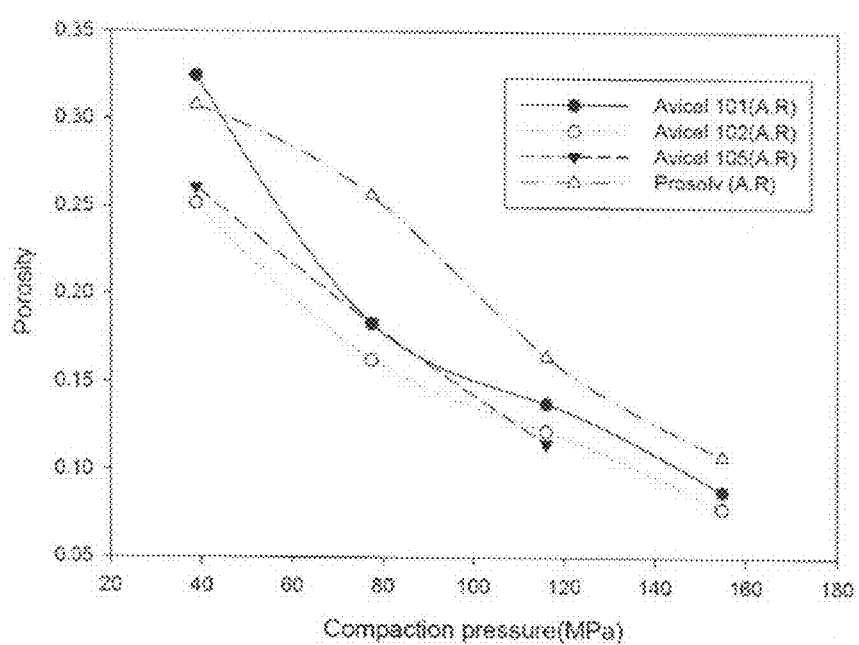
FIG. 11a-d, are, respectively, plots of porosity as a function of compaction pressure for the tablets of FIGS. 10a-d.
Figure 11B:
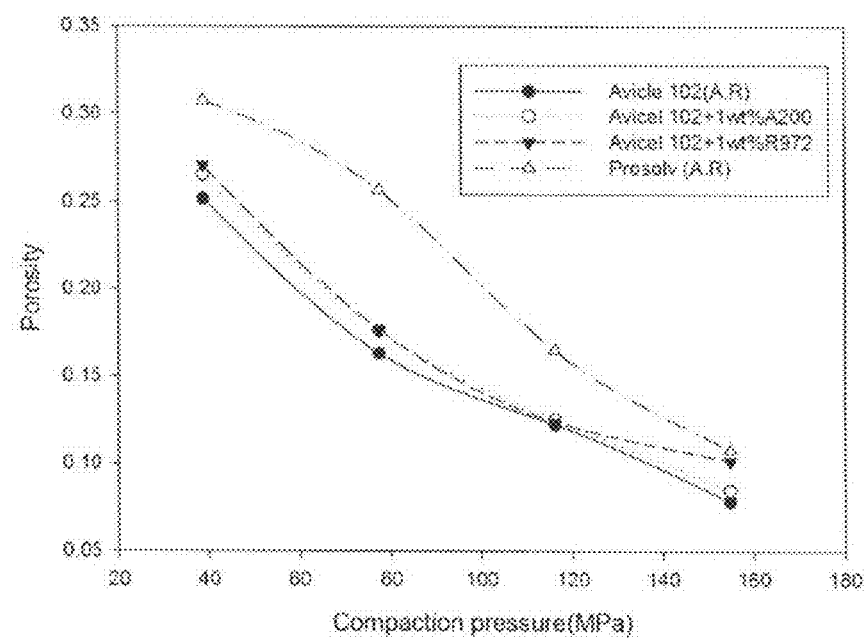
Figure 11C:
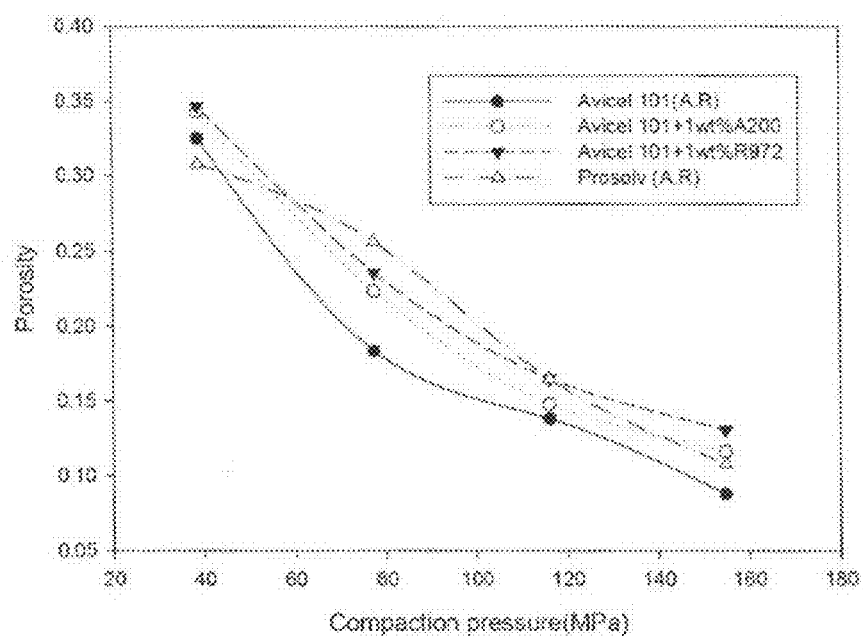
Figure 11D:
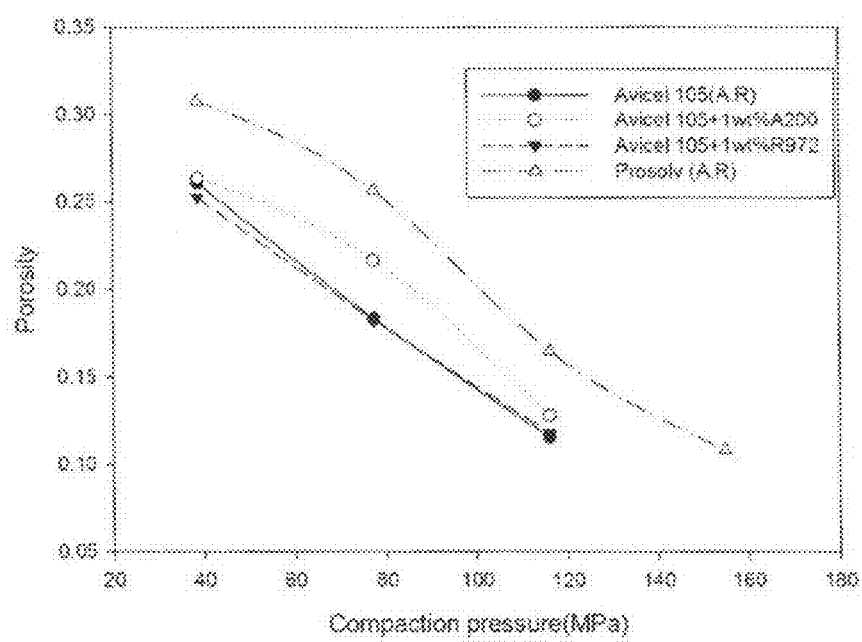
Figure 12A:
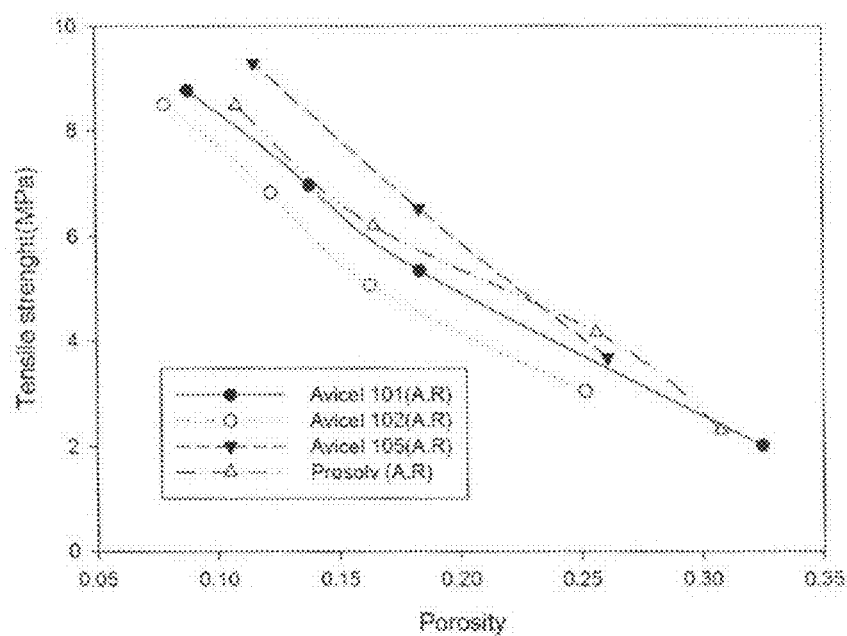
FIG. 12a-d are, respectively, plots of tensile strength as a function of porosity for the tablets of FIGS. 10a-d and 11a-d.
Figure 12B:
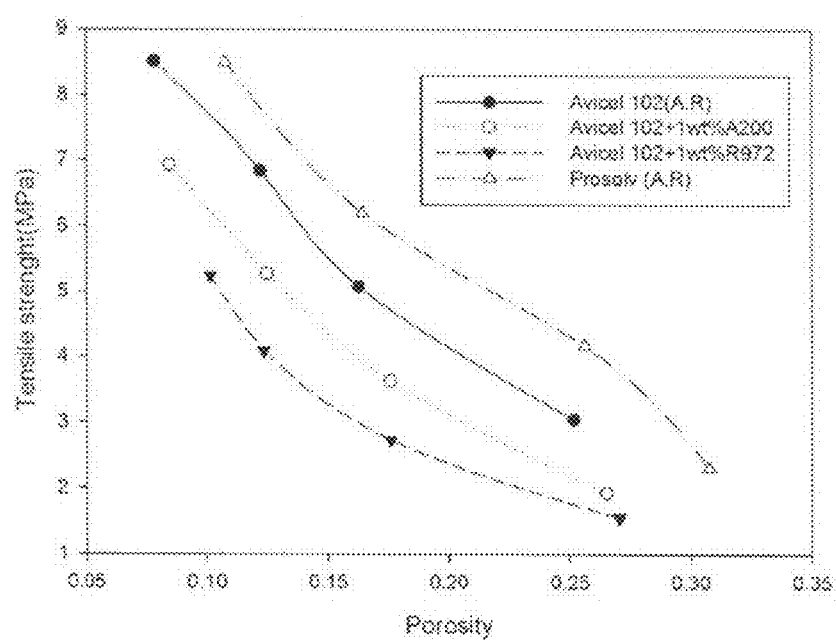
Figure 12C:
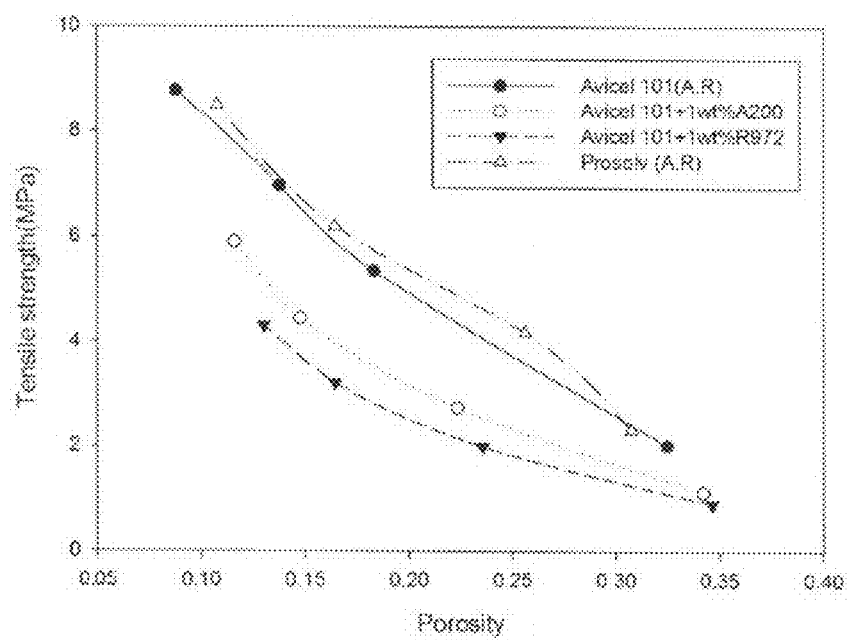
Figure 12:
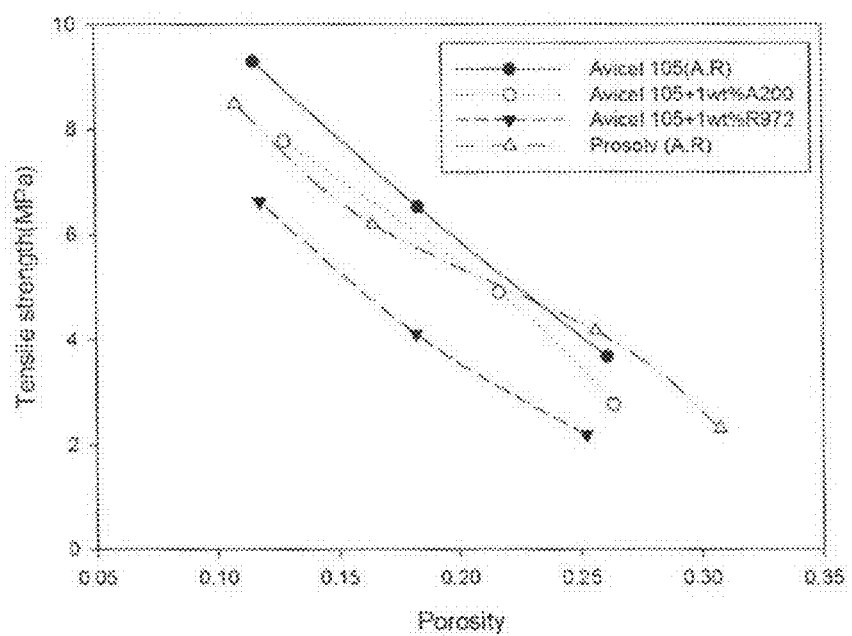

FIGS. 10a-d depicted tabletability of the dry coated excipients of Table 6 in comparison to Prosolv® 90 HD. As shown in FIG. 11a, as received Avicel® 105 had better tabletability than as received coarser grades of Avicel® and Prosolv® 90HD. In FIGS. 11b, as received Avicel® 105, the finest grade of Avicel® studied, had better tabletability than dry coated Avicel® 105. Dry coated Avicel® was as good as or better than Prosolv® 90HD. In FIG. 11c, as received Avicel® 101 had better tabletability than dry coated Avicel® 101. The dry coated Avicel® 101 resulted in weaker tablets, where R972P coated was weakest. In FIG. 11d, as received Avicel® 102, the largest Avicel® grade studied, had tabletability slightly better than that of Prosolv® 90HD. Dry coated Avicel® 102 did not have tabletability as good as Prosolv® 90HD, where coating with A200 was better than that with R972P. Examples 5 and 6 suggest that apart from improved flow and packing, dry coating does not have significant negative impact on tabletability for Avicel® 101, Avicel® 102, and Avicel® 105.

Example 7

Example 7 tests the same excipients as Example 6, except measures compressibility, i.e., porosity as a function of compaction pressure. As shown in FIGS. 11a-d, as received Avicel® grades, as well as dry coated Avicel® grades form less porous tablets compared to Prosolv® 90 HD. Generally, porosity increases slightly after dry coating, where porosity increases slightly more for R972P compared to A200. Example 7 demonstrates that compressibility of Avicel® grades were not significantly by dry coating.

Example 8

Example 8 tests the same excipients as Example 6, except measures compactibility, i.e., tensile strength as a function of porosity. As shown in FIGS. 12a-d, as received Avicel® grades, as well as dry coated Avicel® grades are less compactible compared to Prosolv® 90HD. Example 8 demonstrates that compactibility of Avicel® garages were not significantly impacted by dry coating.

Example 9

Example 9 provides blends of dry coated excipients and an API. Blends of as received excipients and the API are also provided for comparison. The dry coated excipients and as received excipients used in Example 9 have been discussed in prior examples. The dry coated excipients used in example 9 are those provided in Table 10. Better flowing and better compacting excipients are sought to improve performance of API loaded tablets. Preferably, the excipient should enhance the blend properties over a range of API loading amounts such that subsequent processing is improved. The excipient should allow for extending the scope of direct compression tableting using high speed rotary press. Generally, the flow and compaction properties of excipients will be adversely impacted when blended with poorly flowing and poorly compacting APIs. Even the high performance engineered excipients do not allow easy flowing blends with sufficient compaction properties when API loading is increased to about 30 wt % or higher. In example 9, micronized acetaminophen (mAPAP), which is poorly flowing and has poor compaction properties, is used as the API in the blend. Properties of mAPAP are provided in Table 1.

In Example 9, binary blends of mAPAP and various excipients are made and measured at three different API loading amounts, 10 wt %, 30 wt % and 60 wt %, based on the total weight of the binary blend. Binary blends of Prosolv® 90HD were also made and measured using the same range of API loading amounts. The binary blends are identified in Table 11. Each binary blend is made by the following general method. In each blend case, the required amounts of excipients and API were places in a 4 quart vessel and mixed at 25 rpm for 12 minutes in a V blender (Patterson-Kelley, USA).

Figure 13:
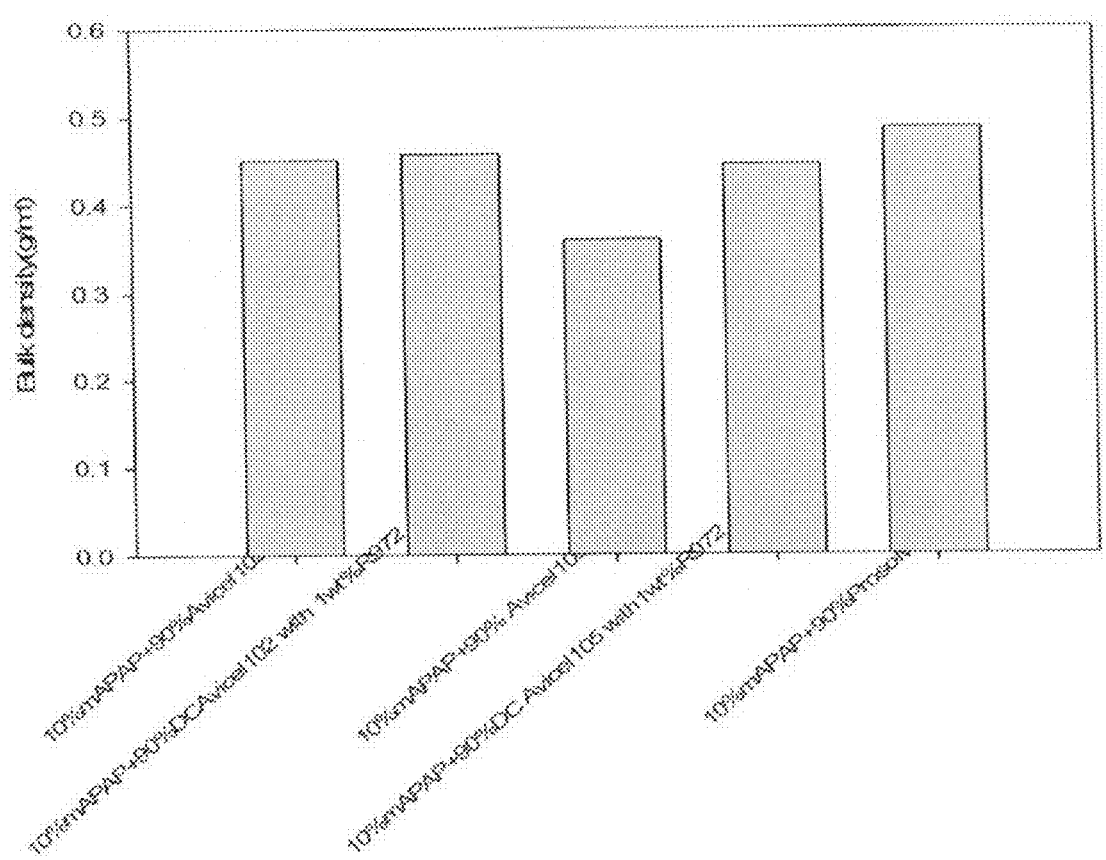
FIG. 13a-c are, respectively bar charts of bulk densities for blends of API and uncoated or dry coated excipients at API loading amounts of 10 wt %, 60 wt % and 30 wt %.
Figure 13:
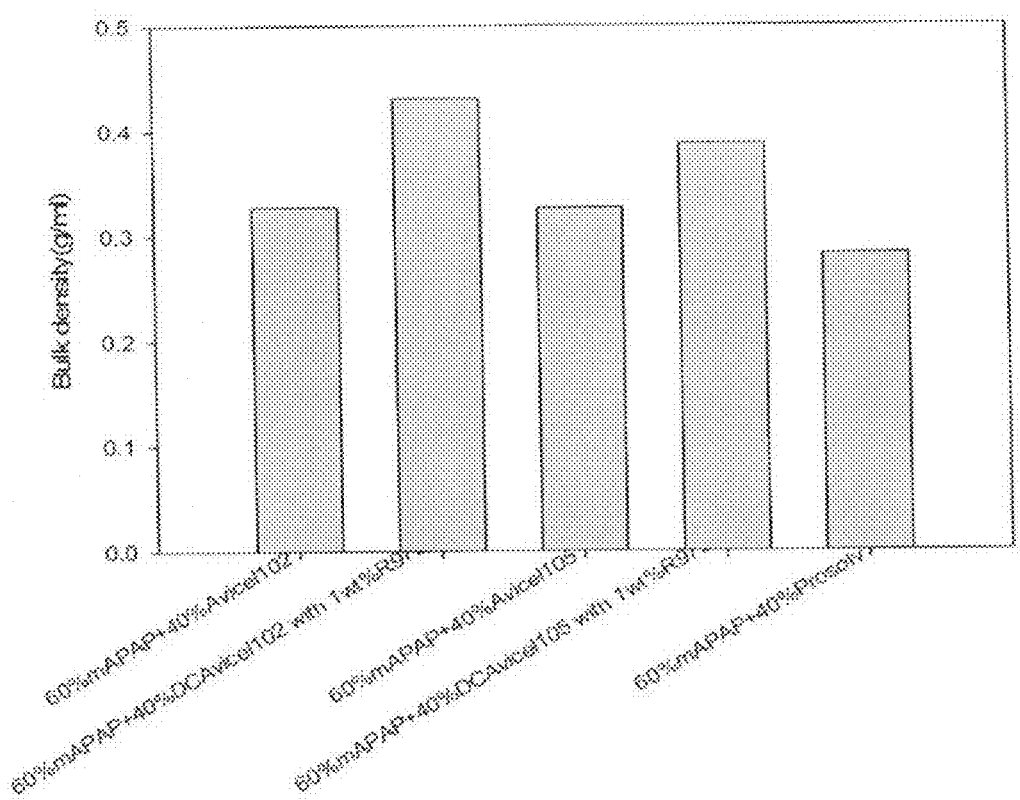
Figure 13C:
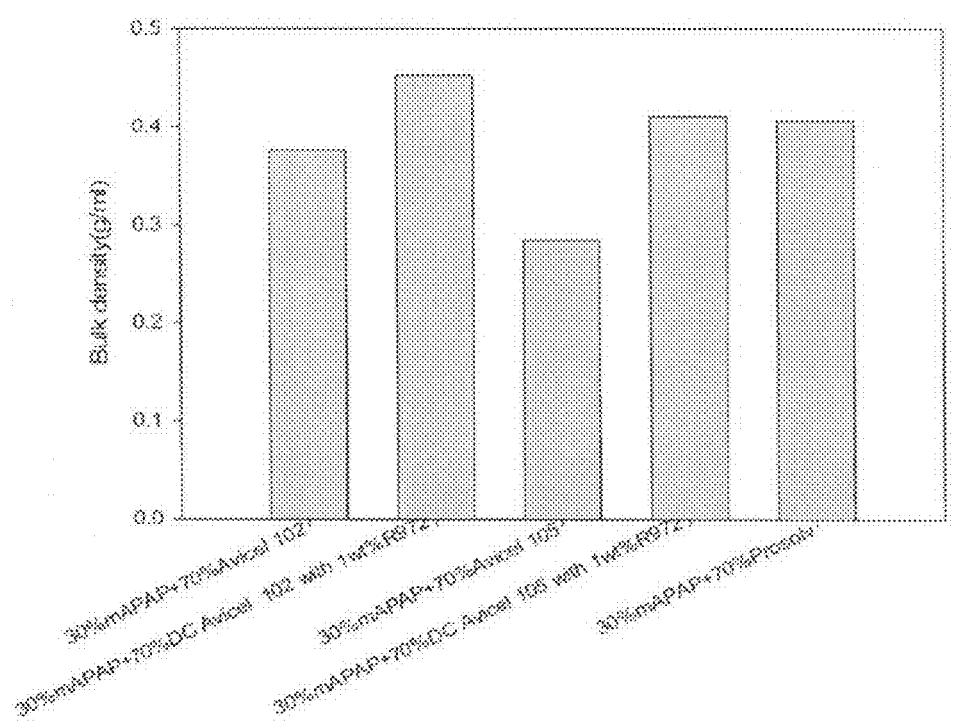
Figure 15A:
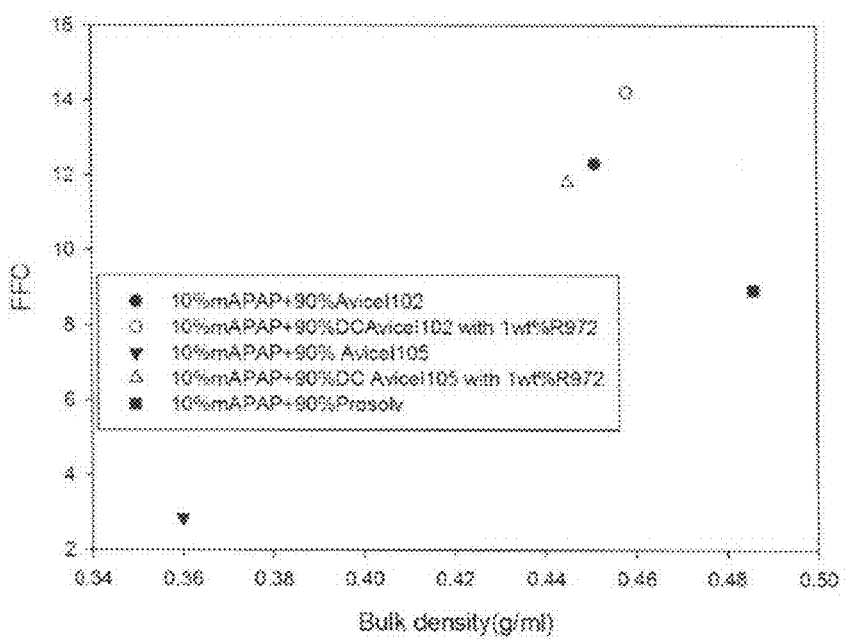
FIGS. 15a-c are, respectively, phase maps of FFC and bulk density for blends of API and uncoated or dry coated excipients at API loading amounts of 10 wt %, 30 wt % and 60 wt %.

In FIGS. 13a-b, show the bulk densities of each binary blend at 10 wt %, 60 wt % and 30 wt % API loading, respectively. In FIG. 13a, each binary blend, except the one using as received Avicel 105® have bulk density above 0.4 g/ml. A bulk density above 0.4 g/mL is generally considered acceptable for direct compaction under good flow conditions. The blend using Prosolv® had the highest bulk density due to the high bulk density of Prosolv® 90HD itself. In FIG. 13b, when 60 wt % mAPAP loading is used, bulk density drop considerably for blends using uncoated Avicel® grades and those using Prosolv® in comparison to the blends using 10 wt % API loading in FIG. 13a. In contrast, the blends using the dry coated Avicel® grades had bulk density, 0.431 g/ml and 0.387 g/ml, using dry coated Avicel® 102 and Avicel 105®, respectively, which was comparable to the bulk density for these dry coated excipients at 10 wt % API loading shown in FIG. 13a. FIG. 13c, which depicts similar blends to FIG. 15a-b, except at 30 wt % API loading shows results consistent with FIGS. 13a-b.

Figure 14A:
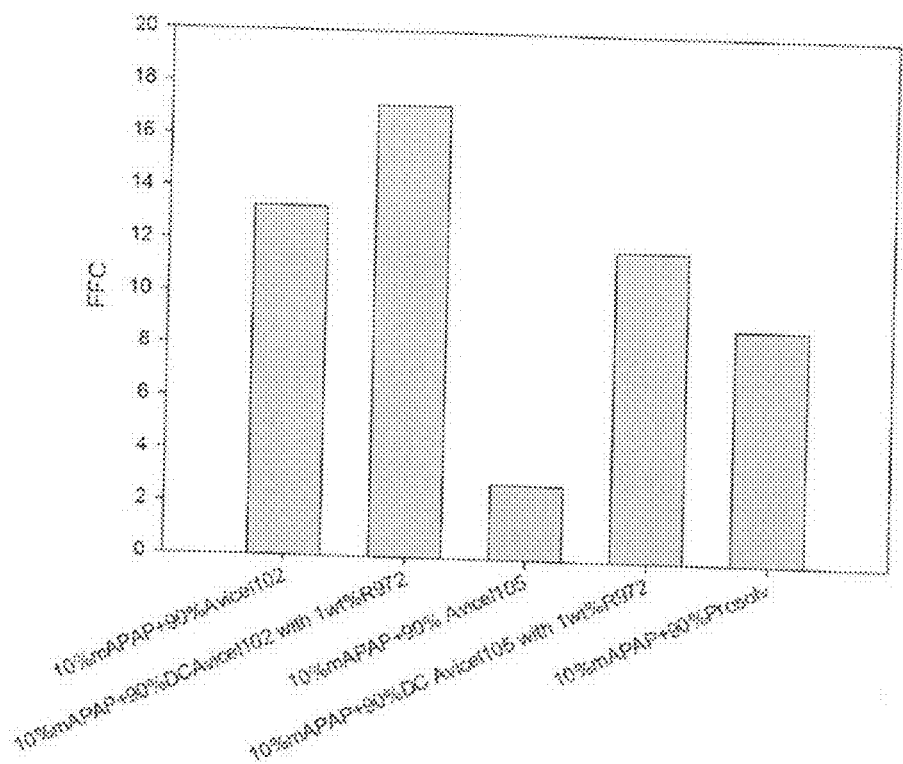
FIG. 14a-c are, respectively, bar charts of flowability for blends of API and uncoated or dry coated excipients at API loading amounts of 10 wt %, 60 wt % and 30 wt %.
Figure 14B:
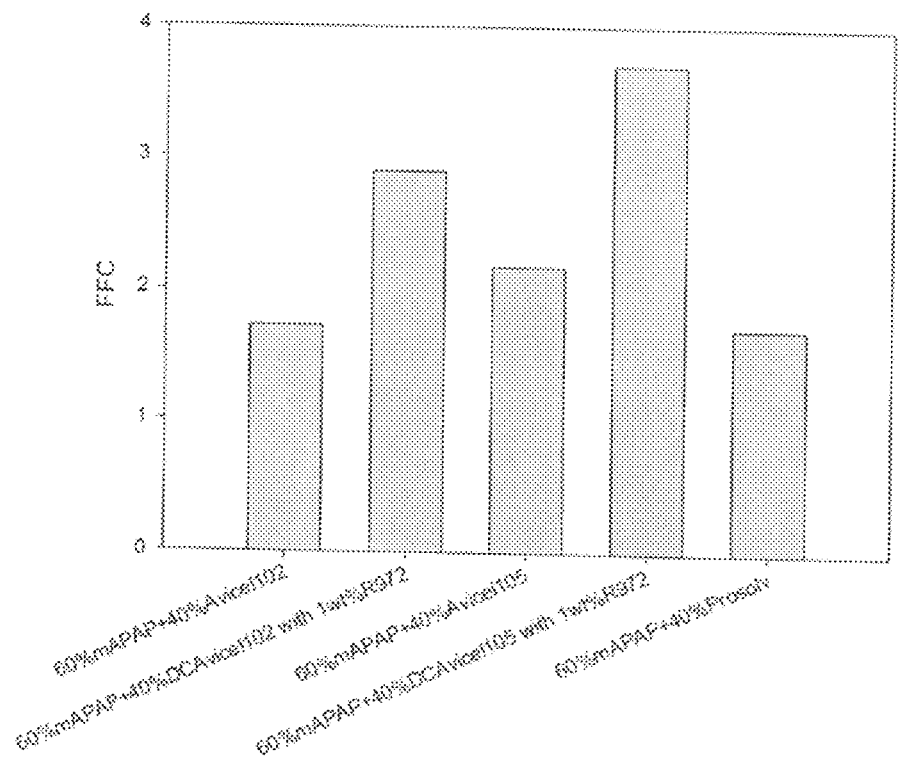
Figure 14C:
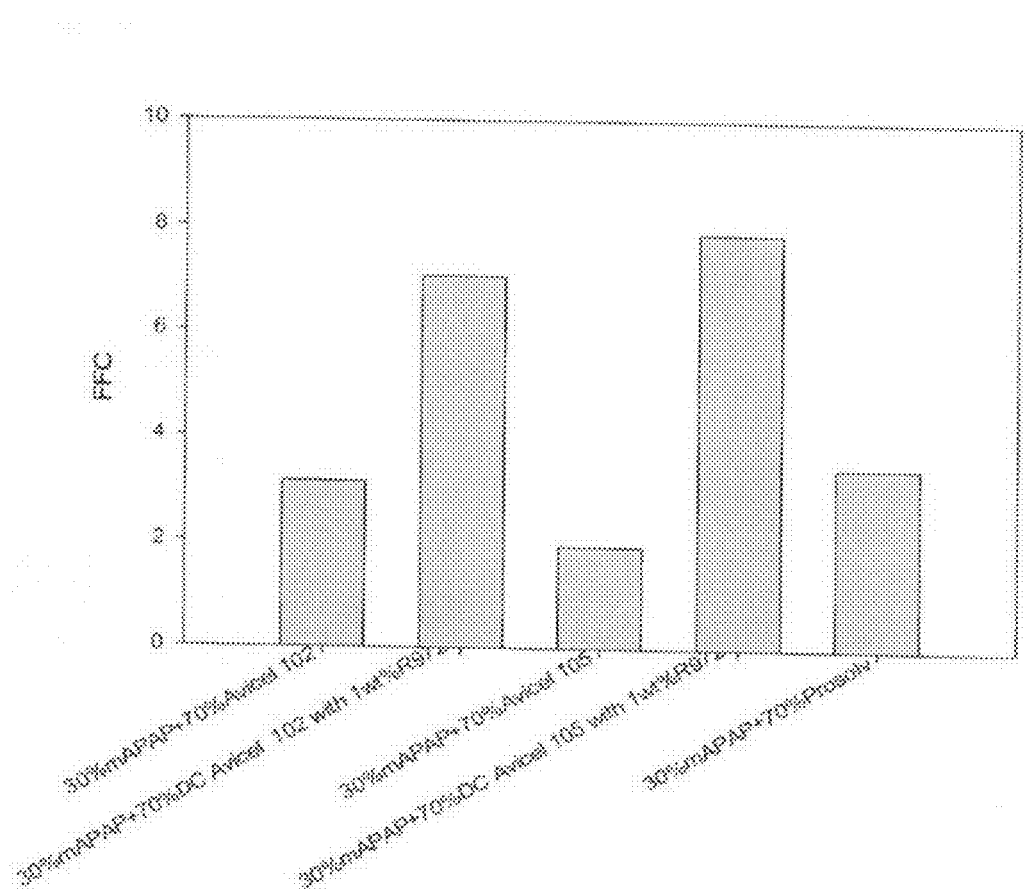

FIGS. 14a-c show flowability of each binary blend at 10 wt %, 60 wt % and 30 wt % API loading, respectively. The flowability was measured using the FT4 shear tester as described herein. The blends using dry coated excipients had improved flowability compared to those using Prosolv® 90HD at each API loading amount as shown in FIGS. 14a-c. This result was unexpected considering that Prosolv® 90HD itself has high flowability. Even at the lowest API loading of 10 wt %, the Prosolv® 90HD containing blend has FFC of only 3.23. In contrast, the blends using dry coated excipients at 10 wt % API loading had FFC above 10 and were in the free flowing regime. At higher API loading of 60 wt % (FIG. 14b), FFC for the blends using dry coated excipients are again higher than those using Prosolv® 90HD, which has FFC of only 1.71 (cohesive regime). These results along with those for flowability of the 30% API loaded blends are summarized in Table 11, and plotted as a 2-D phase map in FIGS. 15a-c. These phase maps show improvement in both bulk density and FFC for the dry coated excipients compared to as received excipients and Prosolv® 90HD. At 10 wt % API blends (FIG. 15a), one of ordinary skill in the art would expect the blend to be dominated by properties of the excipients. However, a cohesive API, such as mAPAP, can have an influence on flowability even at low API loading. At 10 wt % API loading, the dry coated Avicel® blends have mostly retained their properties in comparison to the Prosolv® 90HD blend.

TABLE 11

| Example | mAPAP (wt %) | Excipient (wt %) | Excipient | Bulk Density (mg/mL) | FFC |
|---|---|---|---|---|---|
| 9.1 | 10 | 90 | Ex 5.1 | 0.451 | 12.3 |
| 9.2 | | | Ex 5.3 | 0.458 | 14.2 |
| 9.3 | | | Ex 5.7 | 0.36 | 2.84 |
| 9.4 | | | Ex 5.9 | 0.445 | 11.8 |
| 9.5 | 60 | 40 | Ex 5.1 | 0.327 | 1.72 |
| 9.6 | | | Ex 5.3 | 0.431 | 2.9 |
| 9.7 | | | Ex 5.7 | 0.326 | 2.18 |
| 9.8 | | | Ex 5.9 | 0.387 | 3.71 |
| 9.9 | 30 | 70 | Ex 5.7 | 0.284 | 1.92 |
| 9.10 | | | Ex 5.9 | 0.411 | 7.87 |
| 9.11 | | | Ex 5.1 | 0.376 | 3.14 |
| 9.12 | | | Ex 5.3 | 0.453 | 7.03 |
| 9.13 | 10 | 90 | Prosolv ® 90HD | 0.486 | 8.93 |
| 9.14 | 30 | 70 | Prosolv ® 90HD | 0.406 | 3.43 |
| 9.15 | 60 | 40 | Prosolv ® 90HD | 0.282 | 1.71 |

Figure 15B:
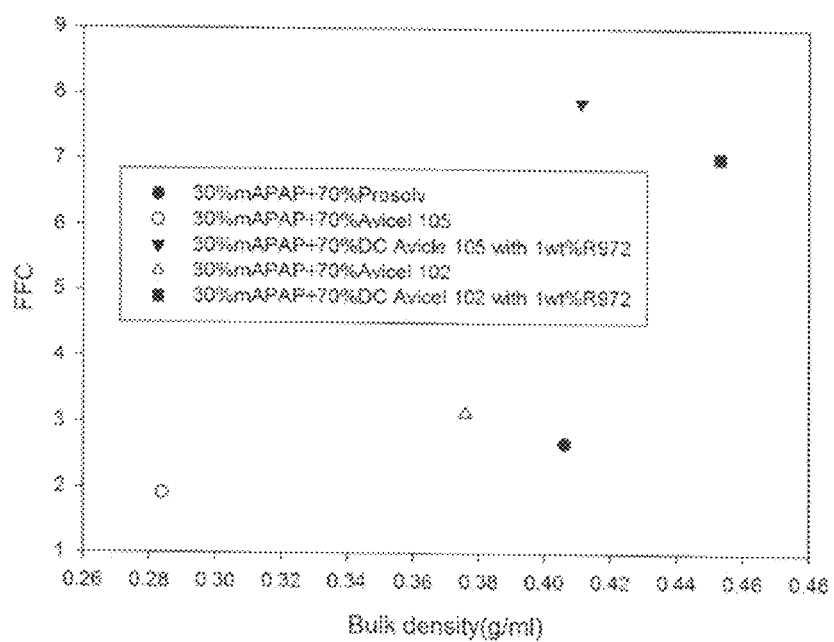
Figure 15C:
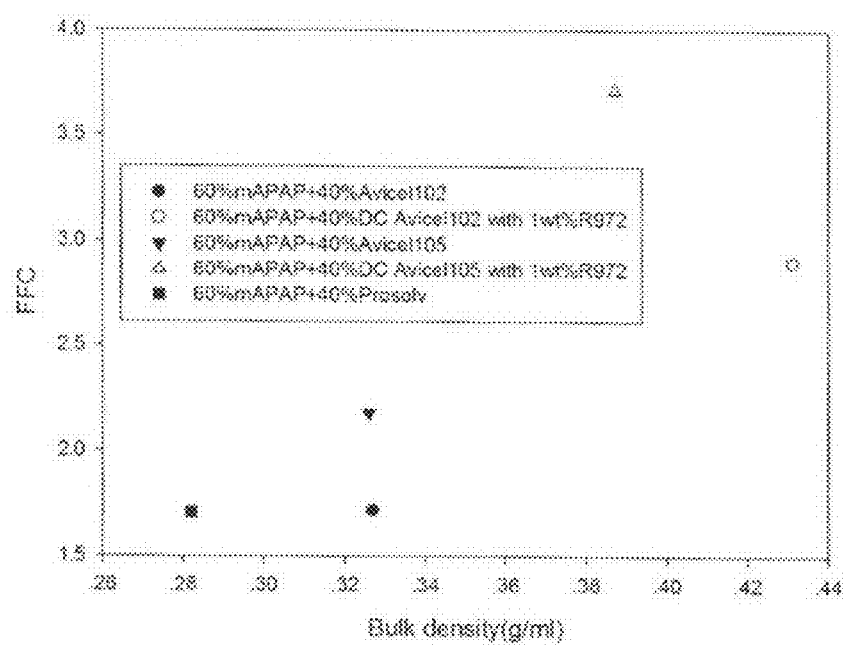

FIG. 15b depicts a 2-D phase map at 30 wt % API loading. As received Avicel® 105 blend has poor flow and bulk density in a blend at 30 wt % API loading, which suggests that wet granulation will be necessary before tableting. However, unexpectedly, the dry coated Avicel® 105 blend was found to have a bulk density is above 0.41 g/ml and an FFC of about 8, which suggests that direct compaction tableting would be feasible and no granulation will be required. In contrast, the Prosolv® blend at 30 wt % API loading has FFC below 4, suggesting that high-speed direct compaction tableting is not possible without granulation. These results show surprising advantageous properties, such as simultaneously improved flow, bulk density, and compaction properties while having very fine size and irregular shapes without the need for wet granulation, of dry coated excipients.

Example 10

Figure 16A:
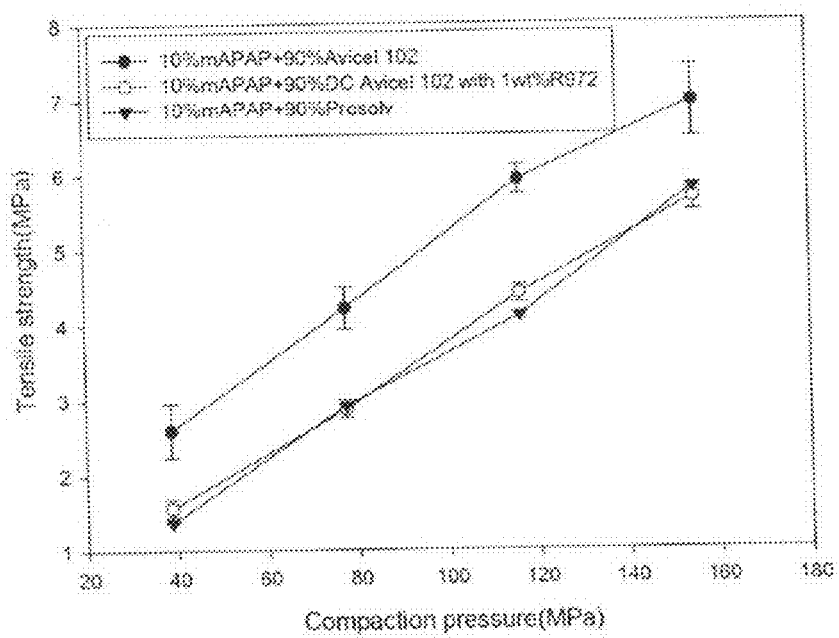
FIG. 16a-d are, respectively, plots of tensile strength as a function of compaction pressure for tablets made from blends of API and uncoated or dry coated excipients in comparison to blends of API and Prosolv® 90 HD at 10 wt % and 60 wt % API loading.
Figure 16B:
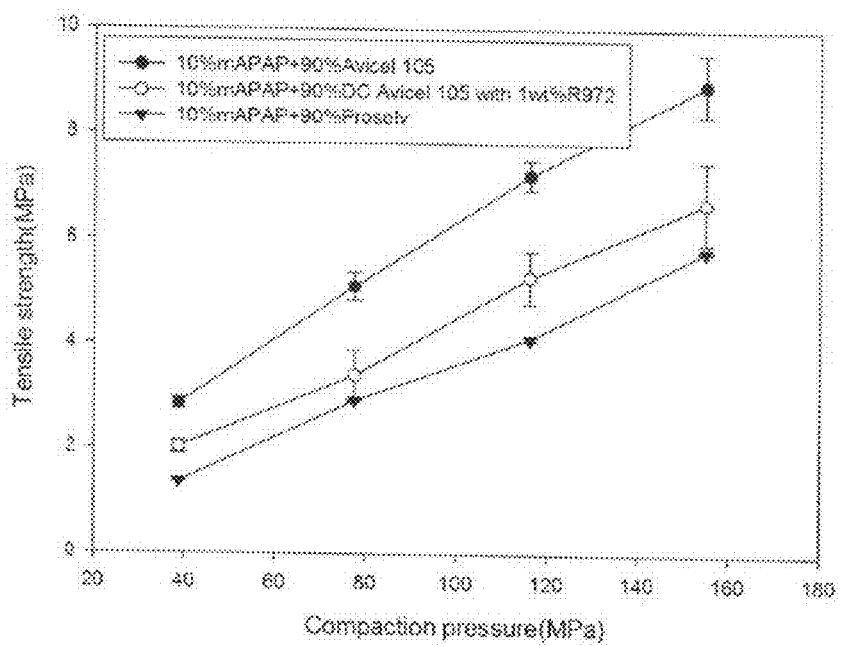
Figure 16C:
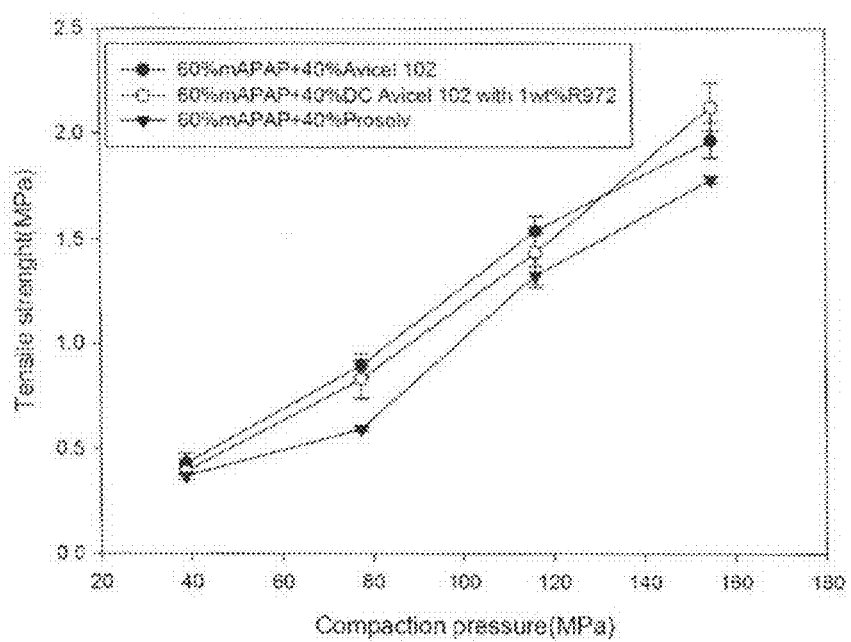
Figure 16D:
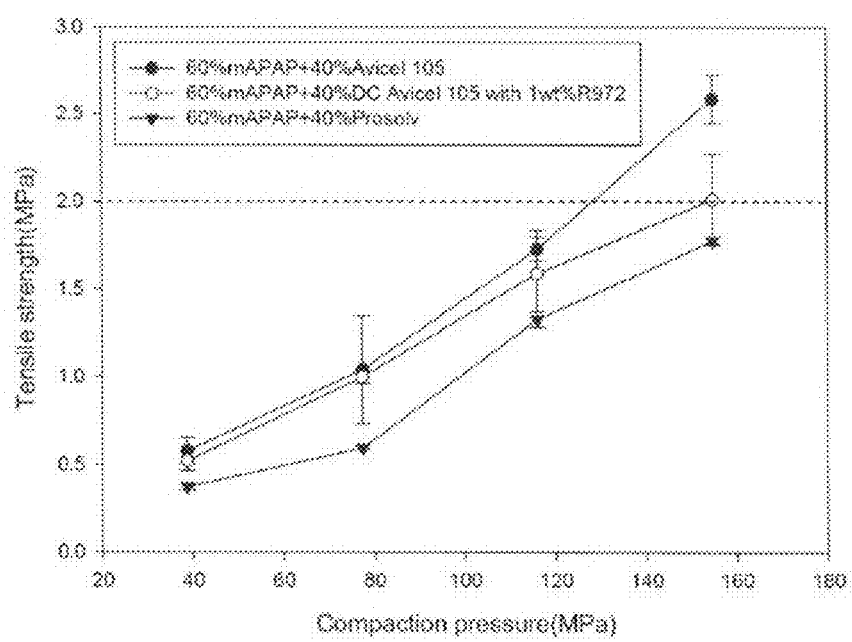
Figure 17:
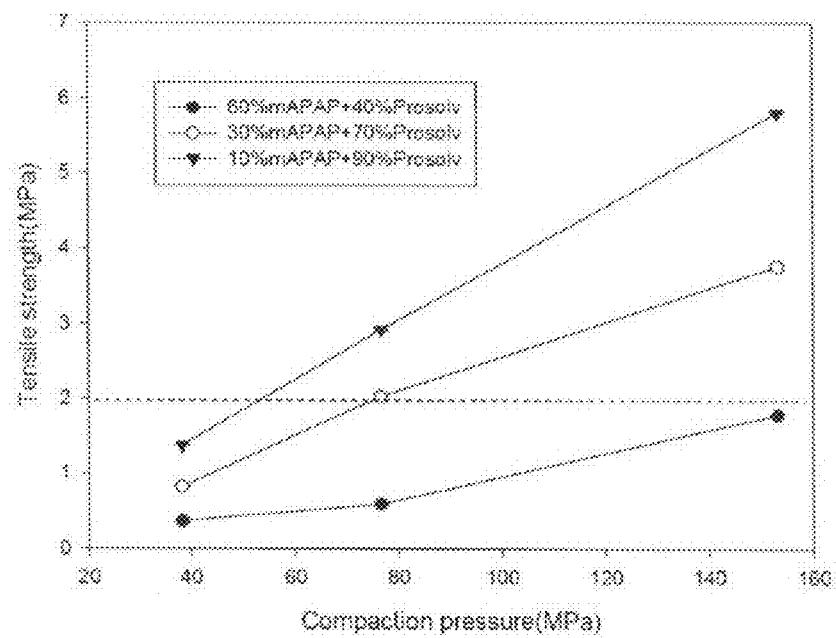
FIG. 17 is a plot of tensile strength as a function of compaction pressure for tablets made from blends of API and Prosolv® 90 HD.
Figure 18A:
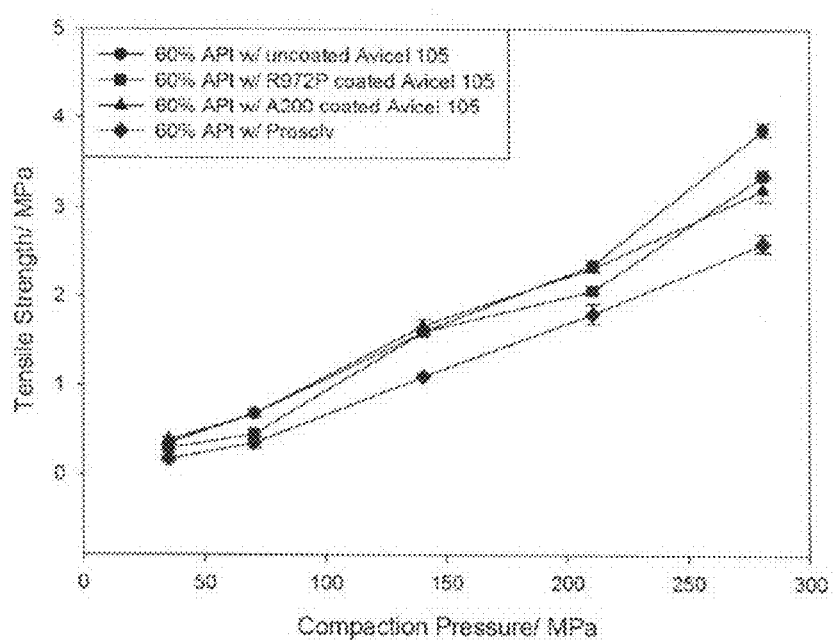
FIGS. 18a-d are, respectively, plots of tensile strength as a function of compaction pressure for tablets made from blends of API and uncoated or dry coated excipients in comparison to blends of API and Prosolve® 90 HD at 60 wt %, 30 wt %, 10 wt %, and 0 wt % API loading.
Figure 18B:
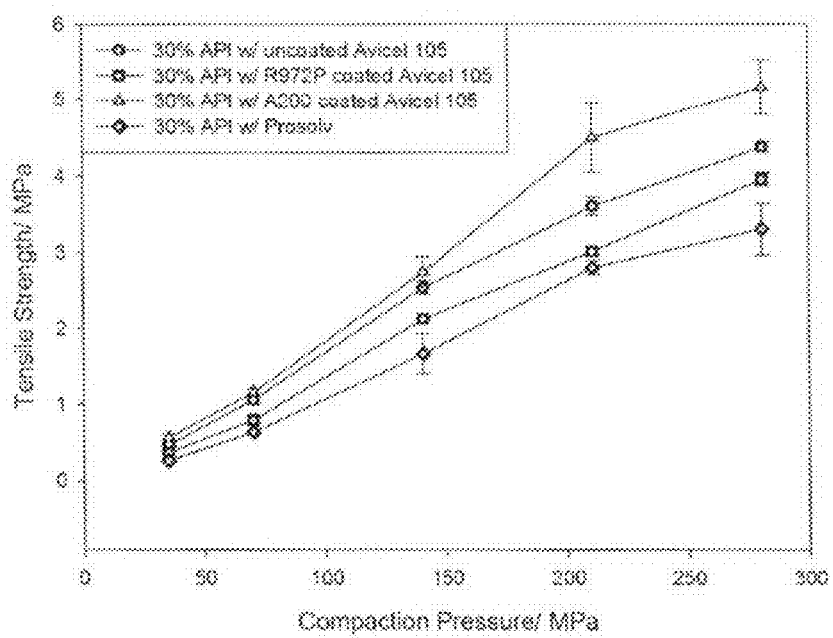
Figure 18C:
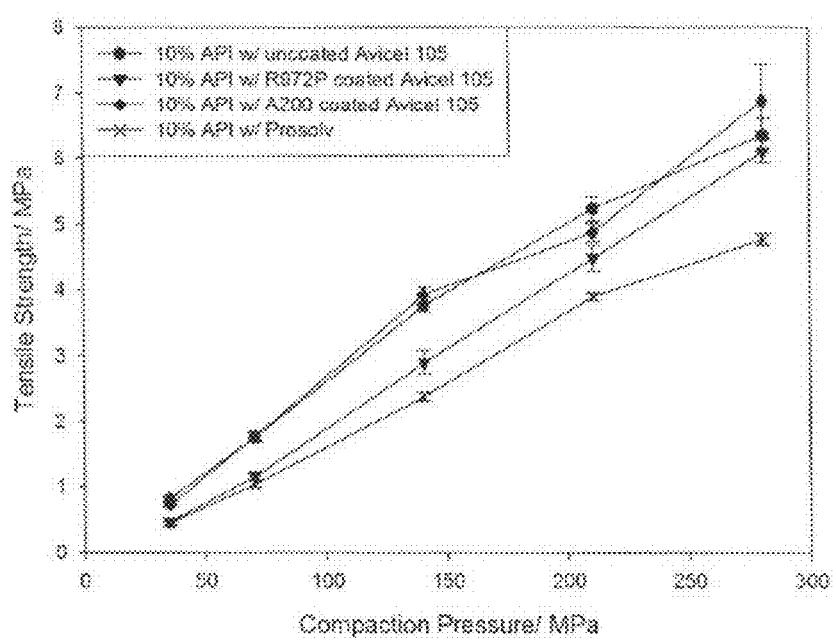
Figure 18D:
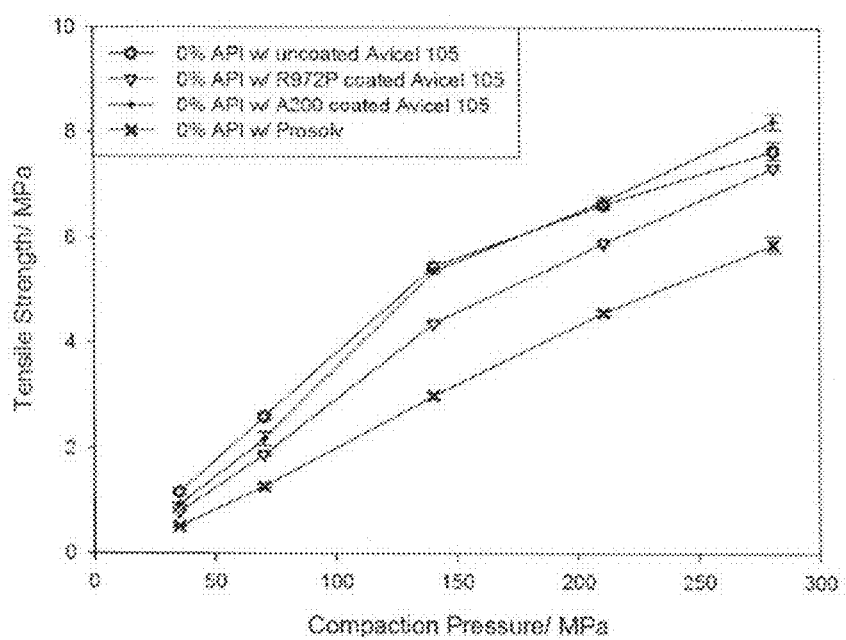
Figure 19A:
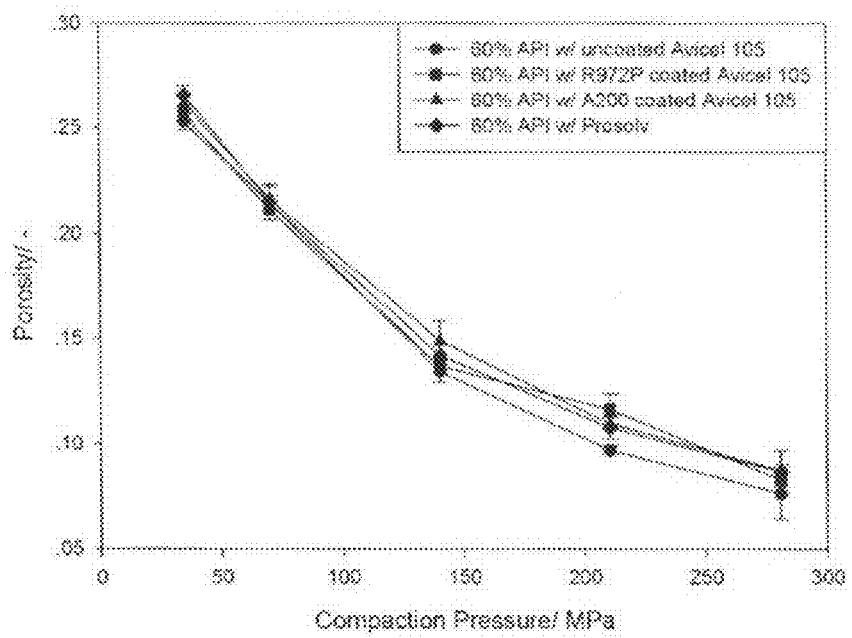
FIGS. 19a-d are, respectively, plots of porosity as a function of compaction pressure for tablets made from blends of FIGS. 18a-d.
Figure 19B:
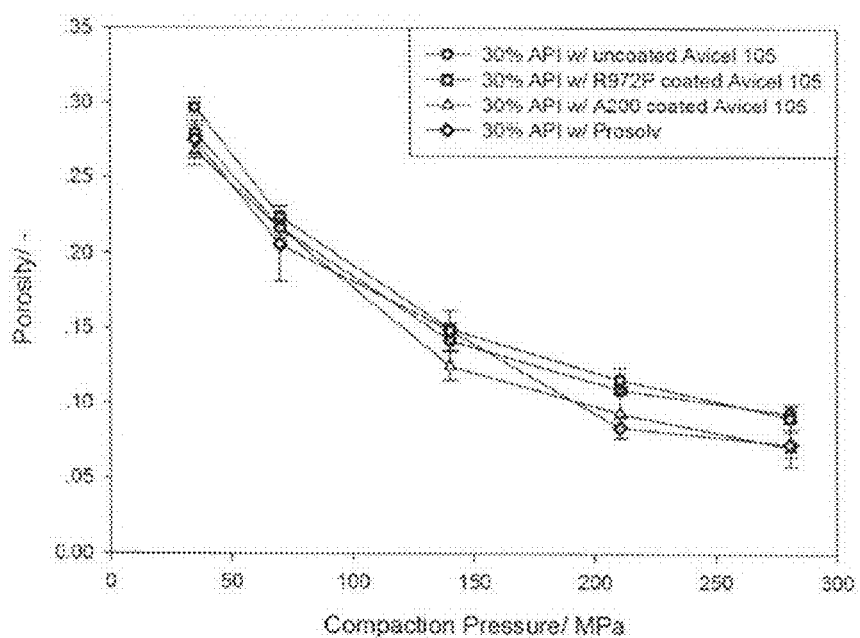
Figure 19C:
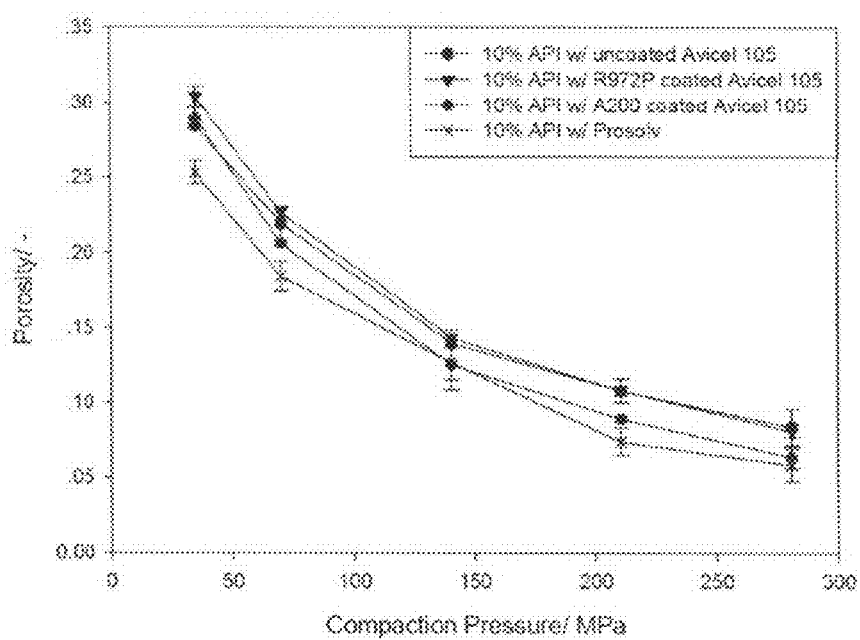
Figure 19D:
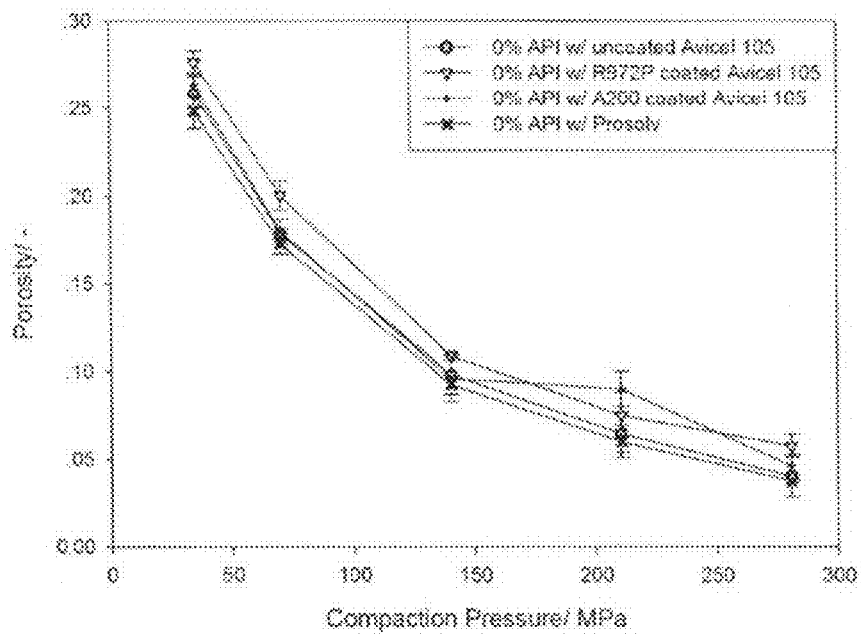
Figure 20A:
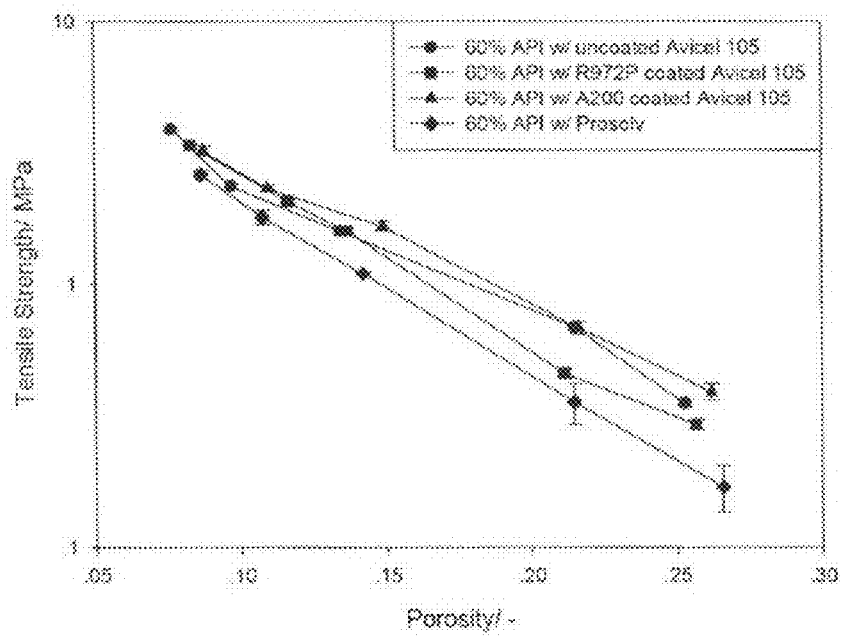
FIGS. 20a-d are, respectively, plots of tensile strength as a function of porosity for tablets made from blends of FIGS. 18a-d.
Figure 20B:
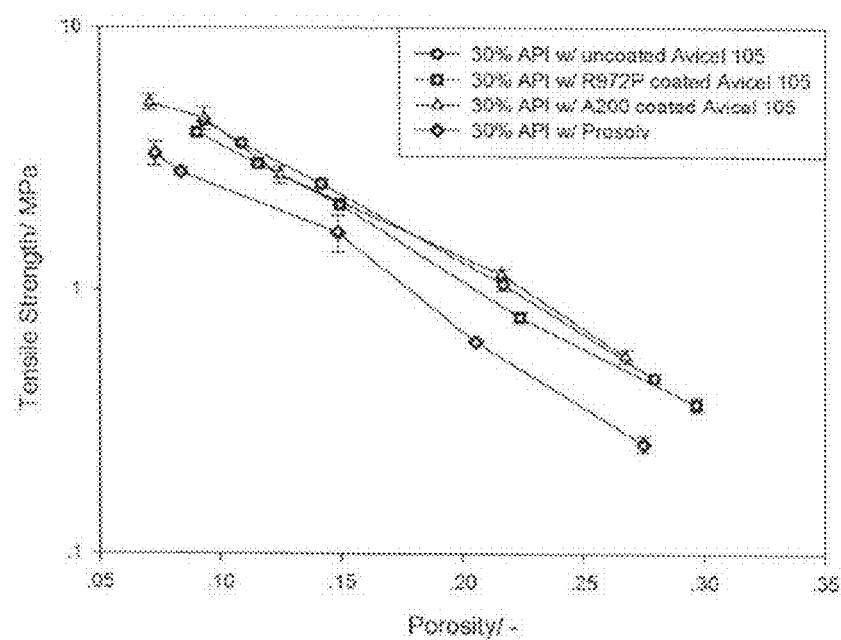
Figure 20C:
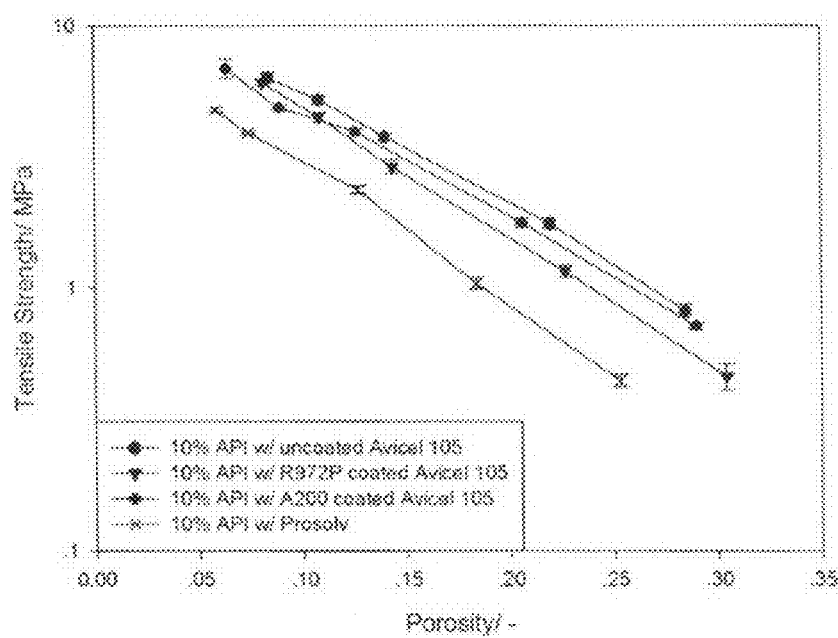
Figure 20D:
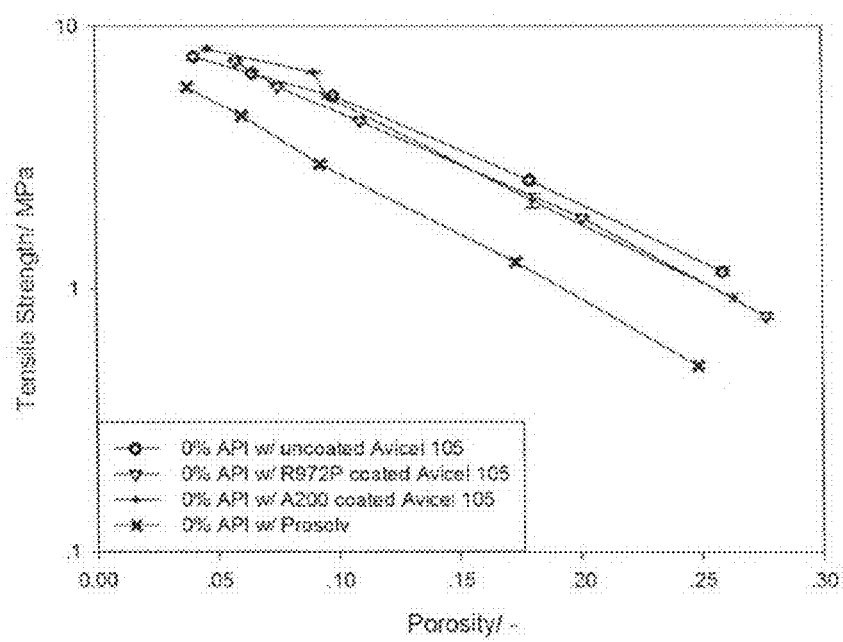

Example 10 evaluates the compaction properties of the blends used in Example 9. Tabletability profiles are shown in FIGS. 16a-d for as received and dry coated Avicel® blends in comparison to those using Prosolv® 90HD. At low API loading (FIG. 16a), the tabletability profiles of dry coated Avicel® 102 blends and those of Prosolv® 90HD were about the same. In contrast, at the same API loading (FIG. 16b), the dry coated Avicel® 105 blend outperformed the Prosolv® 90 HD blend. At high API loading (FIG. 16c), the dry coated Avicel® 102 blend performs better than the Prosolv® 90 HD blend and was comparable to the as received Avicel® 102 blend. This result suggests that any adverse impact of the guest particles on the compaction properties are negated by improved flow and bulk density to attain the same tablet hardness. At high API loading (FIG. 16d), as received and dry coated Avicel® 105 blends had higher tensile strength in comparison to the Prosolv® 90 HD blend. The used of a finer excipient, such as Avicel® 105, can help with tablet hardness. The dashed horizontal line (FIG. 16d) at 2 MPa tensile strength indicates the minimum acceptable tablet strength. The results in FIG. 16d show that higher API blends would not sufficiently compact in the absence of higher compaction forces. Thus, the Prosolv® 90 HD blend at 60 wt % API loading requires even higher compaction pressure than the range used in FIG. 16d to achieve acceptable tablet hardness. FIG. 17 shows tabletability of Prosolv® 90 HD blends at 10 wt %, 30 wt %, and 60 wt % API loading. As API loading increases, compaction properties deteriorate.

Example 11

Example 11 considers blends that use a combination of ductile and brittle excipients as well as disintegrants and lubricants. The disintegrant is crospovidine (trade name Kollidon-CL, BASF Corporation, USA). and the lubricant is magnesium stearate (MgSt, Mallinckrodt Inc., USA). Disintegrants and lubricants are commonly used in for immediate release formulations. The blends measured in Example 11 are provided in Table 12. These blends compare as received and dry coated Avicel® 105 with Prosolv® 90 HD. The blends are prepared as follows mAPAP is combined with as received Avicel® 105, dry coated Avicel® 105 or Prosolv® 90 HD, and Lactose 450, and Crospovidone and blended for about 12 minutes in a V-blender (Patterson-Kelley, USA). Then, MgSt is added for about 75 seconds. The dry coated Avicel® 105 was prepared using Avicel® 105 and 1 wt % silica (R972P or A200) as shown in Table 10 and processed in LabRAM at 75 G vibration intensity (~60 Hz) for 5 min.

TABLE 12

| Example | mAPAP (wt %) | Excipient (wt %) | Lactose 450 (wt %) | Crospovidone (wt %) | MgSt (wt %) |
|---|---|---|---|---|---|
| 11.1 | 0 | Ex 5.7 (47) | 47 | 5 | 1 |
| 11.2 | 10 | Ex 5.7 (42) | 42 | | |
| 11.3 | 30 | Ex 5.7 (32) | 32 | | |
| 11.4 | 60 | Ex 5.7 (17) | 17 | | |
| 11.5a-b | 0 | (a) Ex 5.8 (47) (b) Ex 5.9 (47) | 47 | 5 | 1 |

TABLE 12-continued

| Example | mAPAP (wt %) | Lactose 450 (wt %) | Crospovidone (wt %) | MgSt (wt %) |
|---|---|---|---|---|
| 11.6a-b | 10 | (a) Ex 5.8 (42) | | |
| | | (b) Ex 5.9 (42) | 42 | |
| 11.7a-b | 30 | (a) Ex 5.8 (32) | | |
| | | (b) Ex 5.9 (32) | 32 | |
| 11.8a-b | 60 | (a) Ex 5.8 (17) | | |
| | | (b) Ex 5.9 (17) | 17 | |
| | | Prosolv® 90 HD (wt %) | | |
| Ex 11.9 | 0 | 47 | 47 | 5 | 1 |
| Ex 11.10 | 10 | 42 | 42 | | |
| Ex 11.11 | 30 | 32 | 32 | | |
| Ex 11.12 | 60 | 17 | 17 | | |

FIGS. 18a-d show tabletability of the blends from Table 12 at API loading of 60 wt %, 30 wt %, 10 wt % and 0 wt %, respectively. At 30 wt % and 60 wt % API loading (FIGS. 18a-b), as received and dry coated Avicel® 105 blends have stronger tabletability than those using Prosolv® 90 HD. Blends using dry coated Avicel® 105 with a hydrophilic guest material (A200) at 30 wt % API loading unexpectedly had the highest tabletability. As 10 wt % API loading (FIG. 18c) as received and dry coated Avicel® 105 with A200 had better tabletability than the other cases. A similar trend was observed for 0 wt % API loading, although reduced tabletability for the Prosolv® 90 HD blends was more evident. The results suggest that a ductile dry coated excipient can have beneficial effects when used as a part of ductile-brittle excipient mixture.

FIGS. 19a-d show compressibility of the blends from Table 12 at API loading of 60 wt %, 30 wt %, 10 wt % and 0 wt %, respectively. The variation between the various blends was minimal.

FIGS. 20a-d show compactability of the blends from Table 12 at API loading of 60 wt %, 30 wt %, 10 wt % and 0 wt %, respectively. At the same porosity, Prosolv® 90 HD blends were weakest. The difference became more produced at lower API loading. Though the dry coated Avicil® 105 blends with hydrophobic R972P were weaker than the as received or hydrophilic A200 coated Avicel® 105 blends, the difference was not significant.

Example 12

Figure 21A:
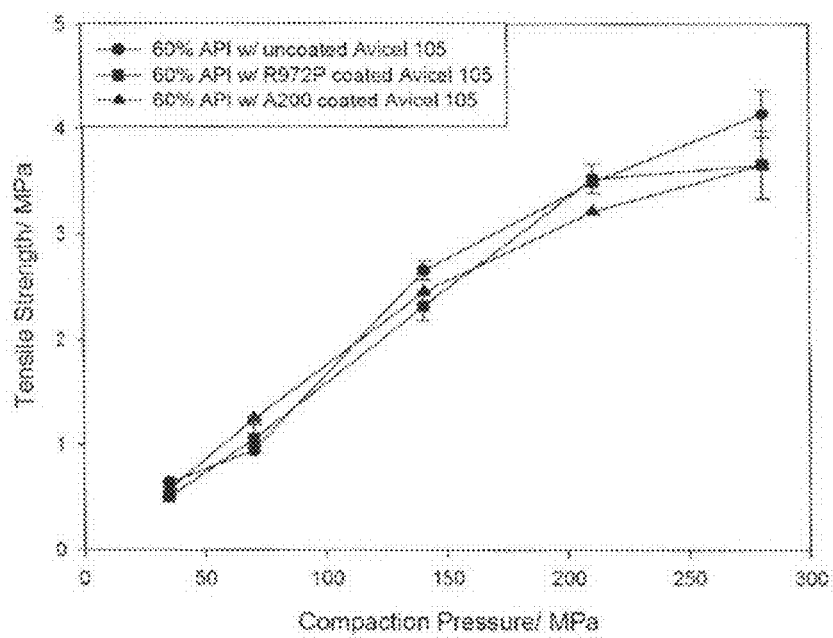
FIGS. 21a-c are, respectively, plots of tensile strength as a function of compaction pressure for tablets made from blends of API and uncoated or dry coated excipients at 60 wt %, 30 wt %, and 10 wt % API loading.
Figure 21B:
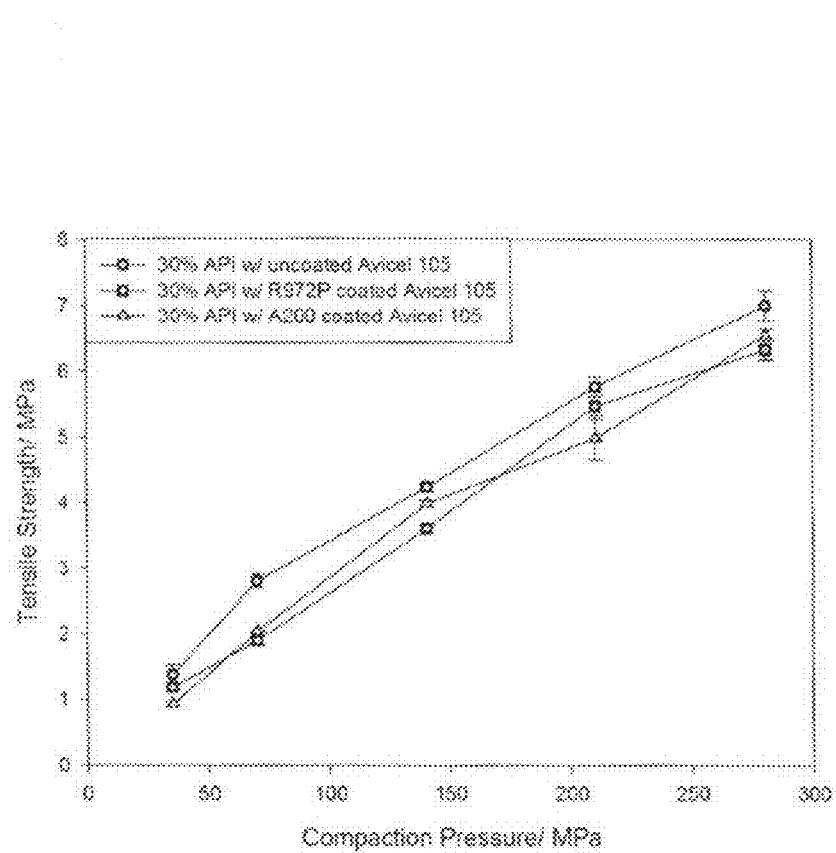
Figure 21C:
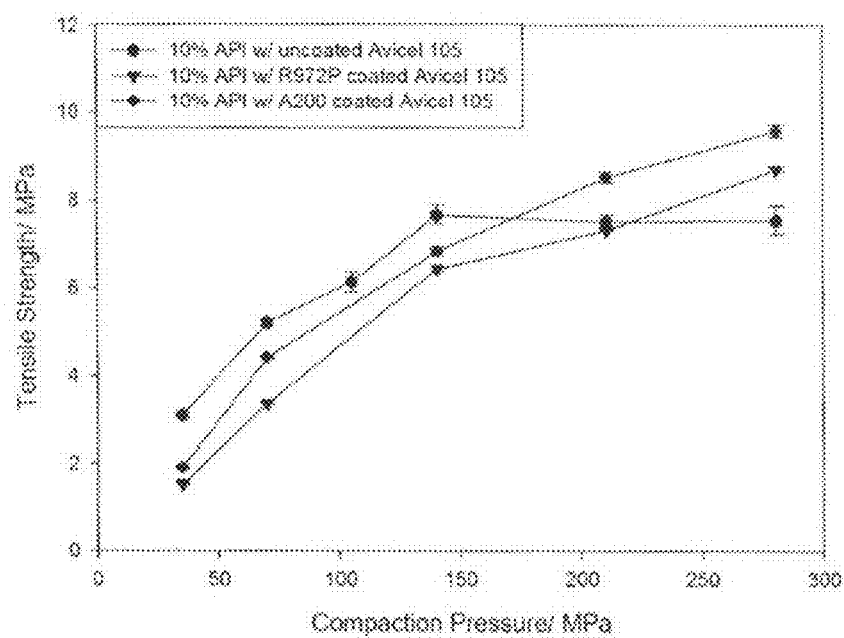

Example 12 generally differs from Example 11 in that the blends of Example 12 do not contain brittle excipients. The blends of Example 12 are summarized in Table 13 and follow similar dry coating and blend mixing protocols used in Example 11. FIGS. 23a-c show tabletability of the blends from Table 9 at API loading of 60 wt %, 30 wt %, and 10 wt %, respectively. At 60 wt % and 30 wt % API loading (FIGS. 21a-b), results indicated that the presence of a guest material does not have a negative effect on tabletability. Generally, the dry coated excipients produce as strong or stronger tablets. At 10 wt % API loading (FIG. 21c), the as received Avicel® 105 blend became overloaded at about 150 MPa, but the dry coated Avicel® 105 blends continued to provide stronger tablets at higher compaction pressures.

Figure 22A:
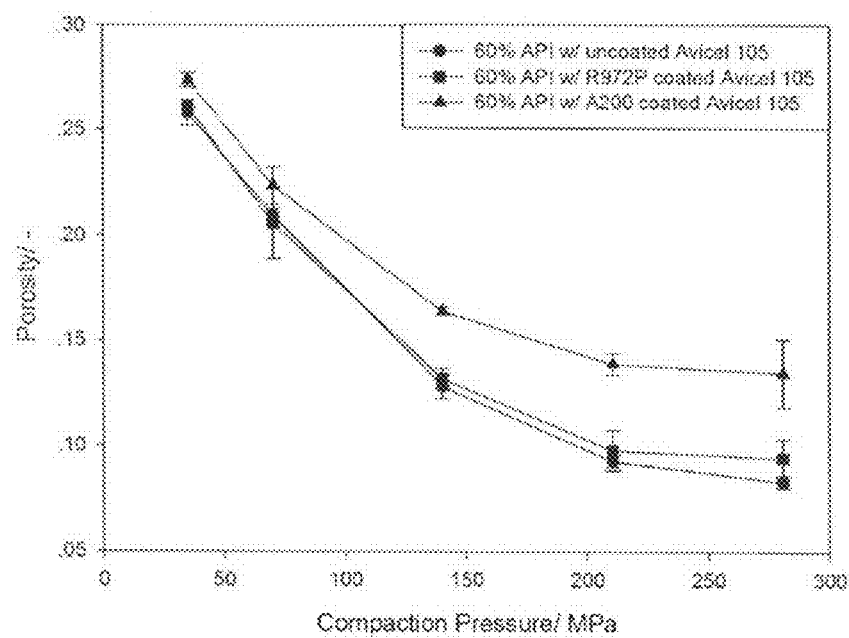
FIGS. 22a-c are, respectively, plots of porosity as a function of compaction pressure for tablets made from blends of FIGS. 32a-c.
Figure 22B:
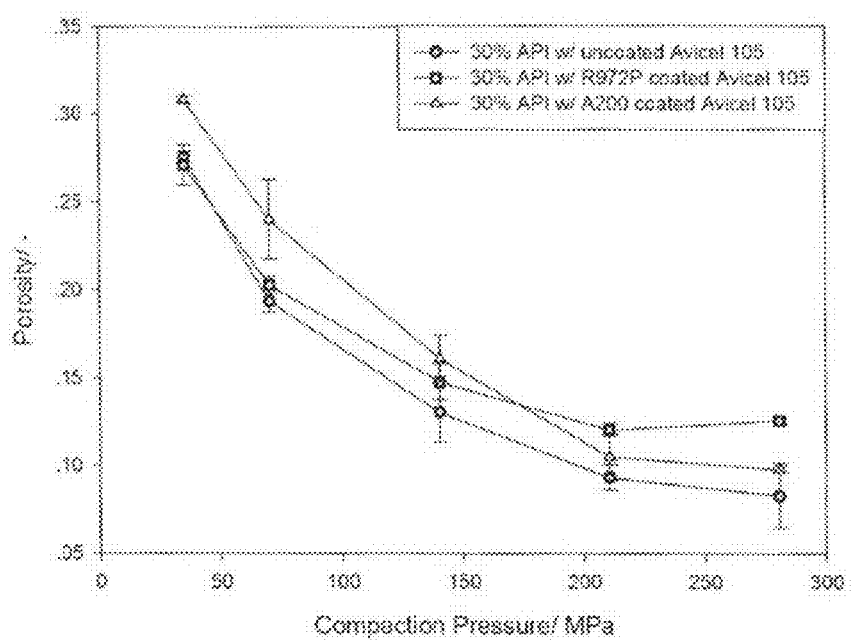
Figure 22C:
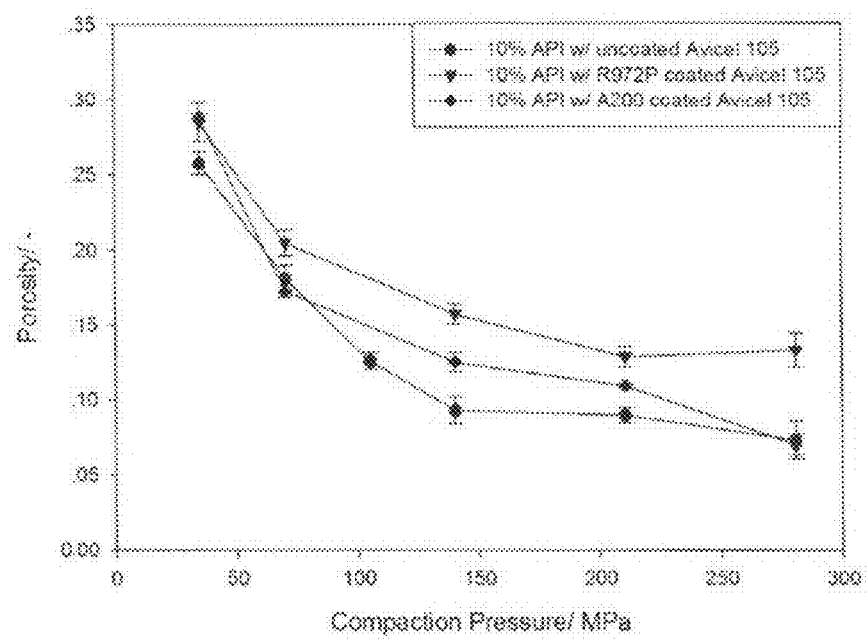

FIGS. 22a-c show tabletability of the blends from Table 9 at API loading of 60 wt %, 30 wt %, and 10 wt %, respectively. The dry coated Avicel® 105 blends generally have higher porosity at the same compaction pressure compared to the remaining blends. Alternatively, as compaction pressure increases, the dry coated Avicel® blends do not compress as much as the as received Avicel® 105 blend.

TABLE 13

| Example | mAPAP (wt %) | Excipient (wt %) | Crospovidone (wt %) | MgSt (wt %) |
|---|---|---|---|---|
| 12.1 | 10 | Ex 5.7 (84) | 5 | 1 |
| 12.2 | 30 | Ex 5.7 (64) | | |
| 12.3 | 60 | Ex 5.7 (34) | | |
| 12.4a-b | 10 | (a) Ex 5.8 (84) | 5 | 1 |
| | | (b) Ex 5.9 (84) | | |
| 12.5a-b | 30 | (a) Ex 5.8 (64) | | |
| | | (b) Ex 5.9 (64) | | |
| 12.6a-b | 60 | (a) Ex 5.8 (35) | | |
| | | (b) Ex 5.9 (34) | | |

Example 13

Figure 23:
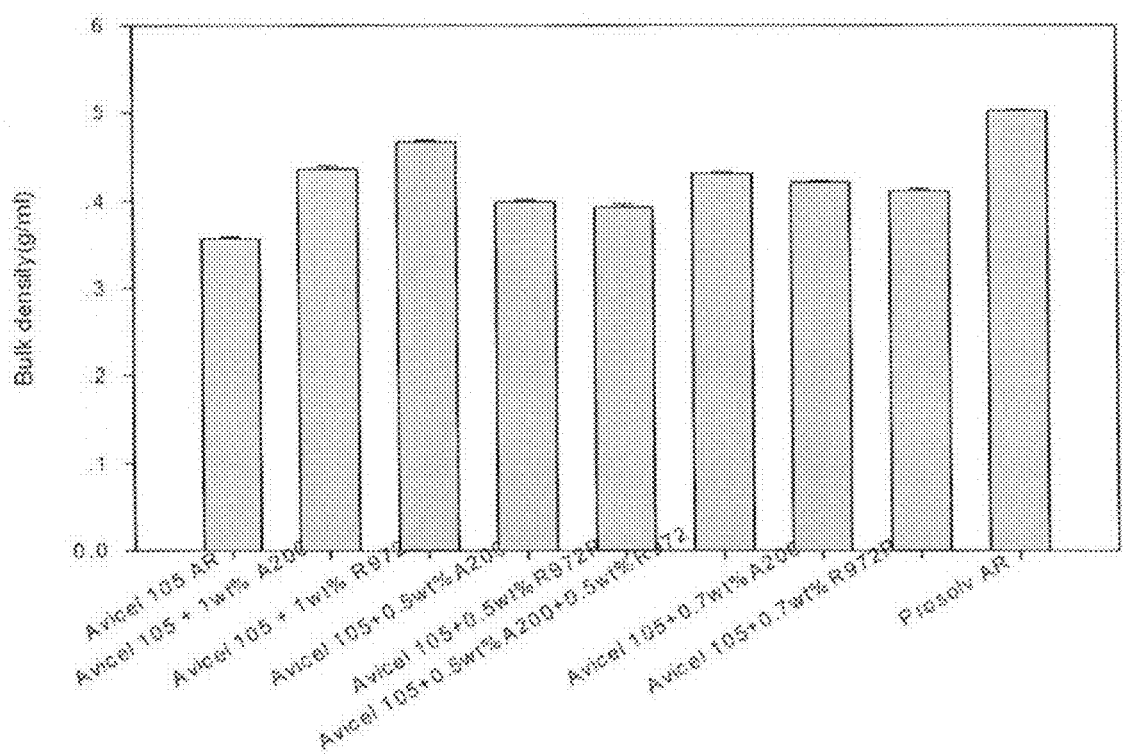
FIG. 23 is a bar graph of bulk density for as received and dry coated Avicel® 105 excipients in comparison to Prosolv® 90 HD.

Example 13 examines flowability and bulk density for dry coated Avicel® 105 when varying type and/or amount of the guest material. The purpose is to examine at what coating level, dry coated Avicel 105® can achieve same of higher bulk density and FFC as what is found for as-received Avicel 102®. The latter (uncoated Avicel 102®) excipient is considered as a benchmark by Sun, C. C., Setting the bar for powder flow properties in successful high speed tableting. Powder Technology 201, 106-108 (2010), for high-speed tableting. In other words, if another excipient has as food or better flow and bulk density, it could be a desirable candidate for consideration in high-speed direct compression tableting. Hydrophilic and hydrophobic guest material (A200 and R972P, respectively) are used individual and in combination as guest materials at 1 wt % silica, 0.5 wt % and 0.7 wt %. As shown in Table 3, these weight amounts indicate differing theoretical surface area coverage for A200 and R972P. Since A200 has finer size, it has a higher theoretical coverage as compared to R972P. Dry coating a fine excipient such as Avicel® 105 does not achieve a high fractional coating coverage efficiency, e.g., ratio of actual coverage estimated via SEM imaging as done in Yang et al., 2005 (referenced above), to theoretical coverage. Therefore, higher theoretical SAC may be required. FIG. 23 depicts bulk density for each excipient. The bulk density improved compared to as received Avicel® 105, even for 0.5 wt % guest material. Generally, the bulk density increases as a function of amount of guest material. A combination of 0.5 weight % each R972P and A200 guest material illustrates how relative hydrophobicity and hence surface energy and bonding strength may be manipulated.

Figure 24:
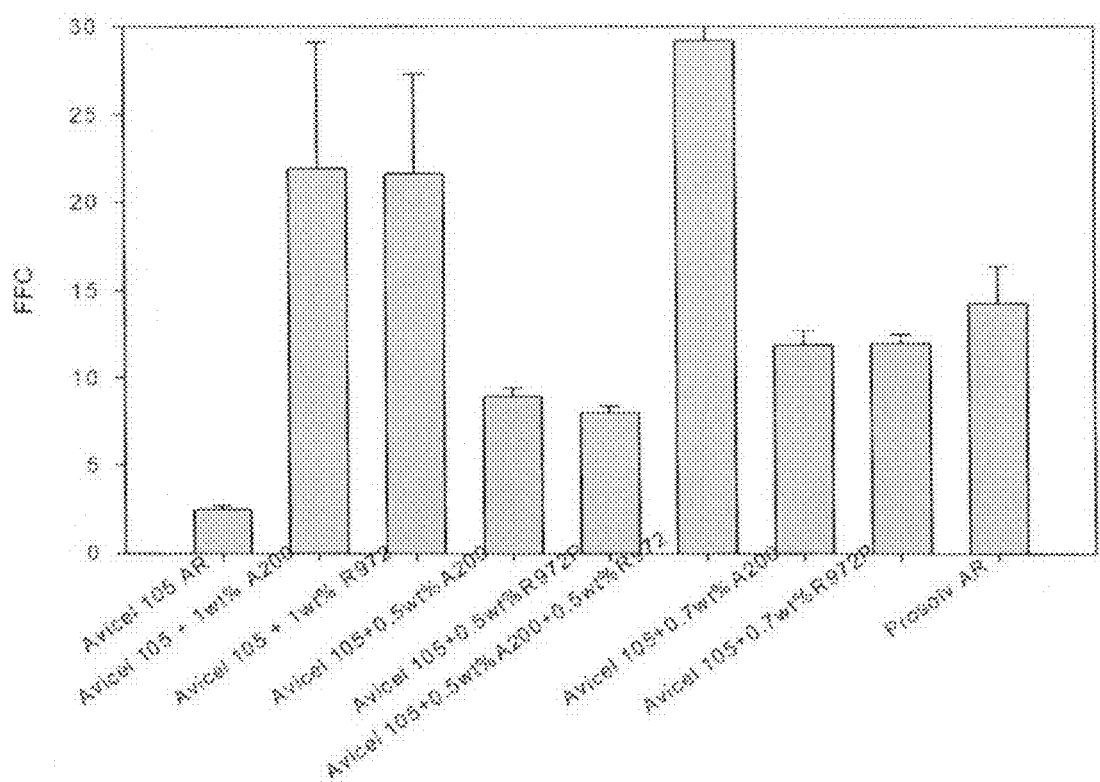
FIG. 24 is a bar graph of FFC for the excipients in FIG. 23

FIG. 24 shows FFC for each excipient. The results indicate that dry coated Avicel® 105 samples using guest material in the amount 0.7 wt % or higher achieve free flow regime, and those with 0.5 wt % achieve easy flow regime. FFC at 0.5 wt % guest material are higher than as received Avicel® 102 (not shown in FIG. 24), which as discussed above, is a benchmark excipient for direct compression tableting by Sun 2010 (referenced above). Bulk Density and FFC for each excipient are summarized in Table 14.

TABLE 14

| Example | Material | Host | Guest (wt %) | Bulk Density (g/mL) | Standard Deviation (SD) | FFC | Standard Deviation (SD) |
|---------|----------|------|--------------|---------------------|-------------------------|------|-------------------------|
| 5.7 | Avicel ® 105 A.R. | Avicel ® 105 | — | 0.357 | 2.00E−03 | 2.49 | 0.215 |
| 5.8 | Avicel ® 105 + 1 wt % A200 | | A200 (1) | 0.436 | 3.00E−03 | 21.9 | 7.23 |
| 5.9 | Avicel ® 105 +1 wt % R972P | | R972P (1) | 0.466 | 2.00E−03 | 21.6 | 5.72 |
| 13.1 | Avicel ® 105 + 0.5 wt % A200 | | A200 (0.5) | 0.399 | 2.00E−03 | 8.95 | 0.45 |
| 13.2 | Avicel 105 + 0.5 wt % R972P | | R972P (0.5) | 0.393 | 3.00E−03 | 8 | 0.4 |
| 13.3 | Avicel ® 105 + 0.5 wt % A200 + 0.5 wt % R972P | | A200 (0.5) R972P (0.5) | 0.43 | 2.00E−03 | 29.2 | 9.15 |
| 13.4 | Avicel ® 105 + 0.7 wt % A200 | | A200 (0.7) | 0.42 | 2.00E−03 | 11.9 | 0.8 |
| 13.5 | Avicel ® 105 + 0.7 wt % R972P | | R972P (0.7) | 0.411 | 2.00E−03 | 12 | 0.5 |
| 13.6 | Prosolv ® 90 HD A.R. | | — | 0.502 | 1.00E−03 | 14.3 | 2.1 |

Compaction properties (Not Shown) for the dry coated Avicel® 105 excipients were evaluated in a manner similar to Examples 6-8. Examples 13.1 through 13.5 were tested and found to be comparable to Examples 5.8 and 5.9 under the same conditions. Loss of tablet strength, compared to as received Avicel® 105 (Example 5.7), decreased as the amount of guest material decreased. Example 13.3, which uses a combination of A200 and R972P had better compaction properties than R972P alone at 1 wt % (Example 5.9). All Examples in Table 14 outperformed as received Avicel® 105 and Prosolv® 90 HD in terms of compaction properties.

Binary blends were made at 10 wt %, 30 wt % and 60 wt % mAPAP loading Examples 13.1 through 13.5 in a similar manner to Example 9. These blends resulted in tablets having higher tensile strength (not shown) in comparison to as received Avicel® 105 and Prosolv® blends.

Example 14

Example 14 measures the surfaces energies of Avicel® 105 and several guest materials, Aerosil 200 (A200), M5P, and R972P. The results for these measurements for various materials are shown in FIG. 1 and tabulated in Table 15. As shown, A200 has the highest dispersive surface energy among the guest materials, while R972P has the lowest dispersive surface energy.

Etzler et al., 2011 (referenced above) proposed a model that if the powders are composed of different materials, the tensile strength can be predicted by using Eq. (9), where $\gamma_1$ and $\gamma_2$ are the surface free energy of two different materials, and a is the material tensile strength.

$$\sigma \propto \gamma_{12} = \gamma_1^{1/2} \gamma_2^{1/2} \qquad (9)$$

According to this model, even a simple mixture of Avicel® 105 and guest material would lead to reduction in tablet strength since surface energy of the guest material is lower than that of Avicel® 105. Thus, it is not possible to avoid reducing the tensile strength if the additives or guest materials have a lower surface energy than the host material in dry coating.

Figure 25:
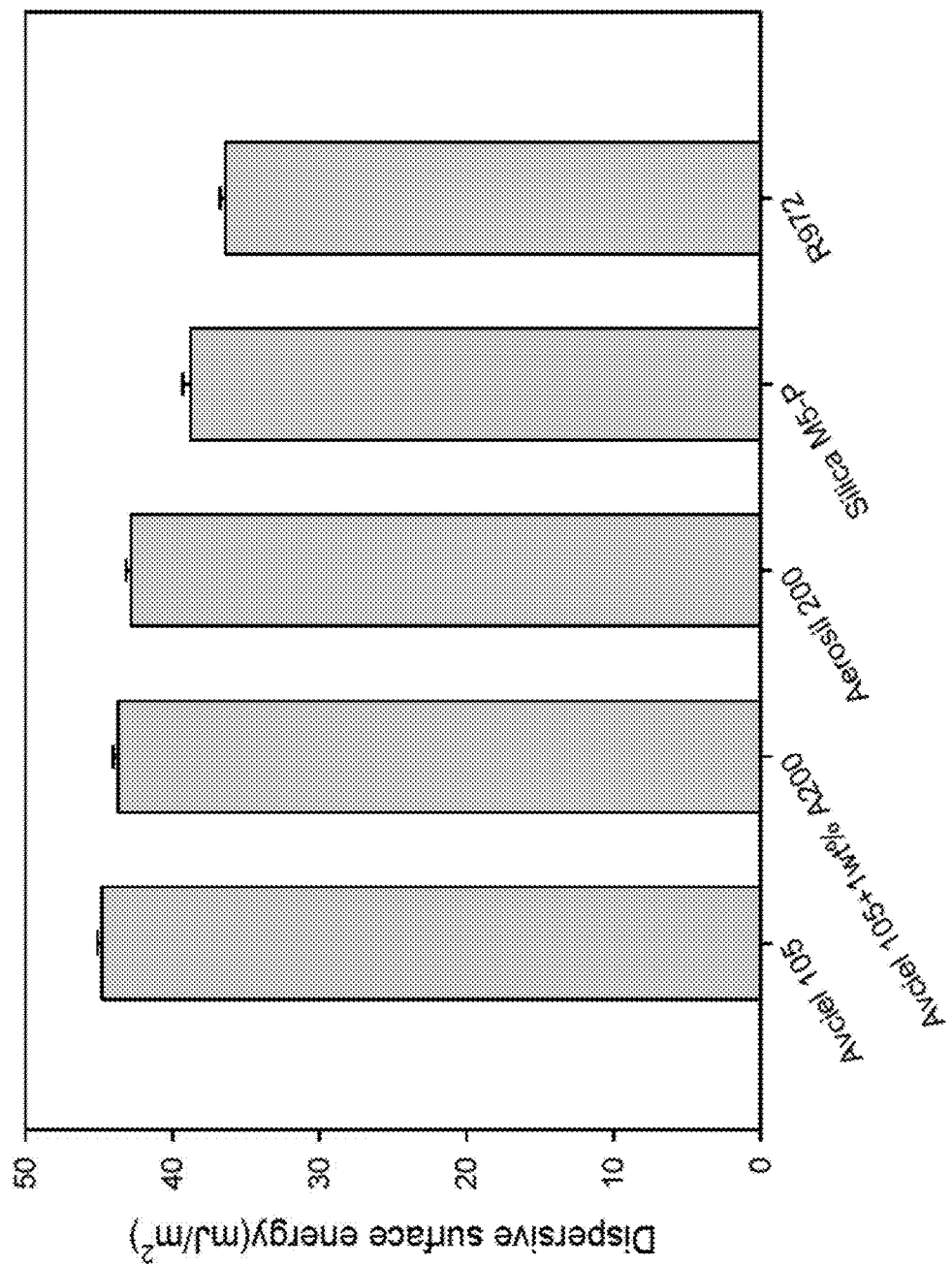
FIG. 25 is a bar graph of dispersive surface energy for uncoated and dry coated excipients, and guest materials.

In order to minimize the loss of the compaction of Avicel® 105 after dry coating, A200 was selected as guest material due to its highest dispersive surface energy among the three types guest materials being measured in Example 14 (see FIG. 25). Example 14.1 was prepared in the same manner as Examples 5.8, except using M5P as the guest material. The dry coated Avicel® 105 with 1 wt % A200 has the highest tensile strength in comparison to the other guest materials as shown in Table 11.

TABLE 15

| Example | Materials | Bulk density (g/ml) | FFC | Dispersive surface energy (mJ/m$^2$) | Tensile strength (MPa) |
|---------|-----------|---------------------|-----|--------------------------------------|------------------------|
| 5.7 | Avicel ® 105 | 0.357 ± 0.003 | 2.53 ± 0.21 | 44.76 ± 0.23 | 9.31 ± 0.31 |
| 5.8 | Avicel ® 105 + 1 wt % A200 | 0.432 ± 0.004 | 21.6 ± 5.43 | 43.71 ± 0.28 | 7.77 ± 0.21 |
| 14.1 | Avicel ® 105 + 1 wt % M5P | 0.425 ± 0.002 | 8.34 ± 1.25 | 41.21 ± 0.37 | 7.24 ± 0.18 |
| 5.9 | Avicel ® 105 + 1 wt % R972P | 0.427 ± 0.003 | 21.9 ± 4.78 | 38.78 ± 0.32 | 6.62 ± 0.28 |

Example 15

Figure 26A:
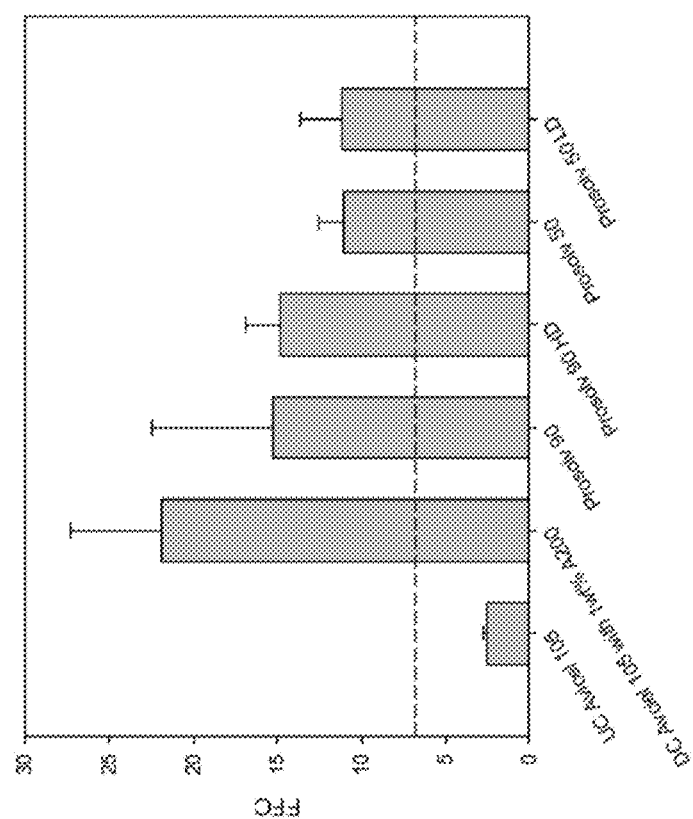
FIGS. 26a-b are, respectively, bar graphs of bulk density and FFC of uncoated and dry coated excipients in comparison to various grades of Prosolv®.

Example 15 compares bulk density and flowability of dry coated Avicel® 105 in comparison to commercially available Prosolv® 90 HD excipients. Fine grade of excipient (e.g., Avicel® 105) typically show good compaction properties due to large bonding surface area (Leuenberger, et al. 1999; Shi, et al, 2011 (both referenced above)). However, the fine particle size (~20 µm) makes it very cohesive, leading to relatively low bulk density, flowability (Castellanos, et al. 2005; Chen, et al., 2010; Geldart, et al., 2009; Han, et al., 2013; Huang et al., 2015 (all referenced above)). Consequentially, handling and feeding problems can occur during processing. As received Avicel® 105 had a very rough surface and irregular shape as determined by SEM (not shown). Such highly non-spherical, irregular shape is expected to negatively affect flow properties and bulk density (Maghsoodi, M., et al., Improved compaction and packing properties of naproxen agglomerated crystals obtained by spherical crystallization technique. Drug Development and Industrial Pharmacy 33, 1216-1224 (2007); Nokhodchi, A., et al., Preparation of agglomerated crystals for improving flowability and compactibility of poorly flowable and compactible drugs and excipients. Powder Technology 175, 73-81 (2007)). After dry coating with 1 wt % A200, the nano-sized silica particles appeared to be evenly distributed on the surface of the Avicel® 105 particle as determined by SEM (not shown), which appears to have reduced the roughness of the particle surface of Avicel® 105. This can result in reduced cohesion, as shown by contact models in (Chen et al., 2008 (referenced above)). Reduced cohesion can result in better packing density because the particles form weak structures that easily collapse (Abdullah, E. C., et al., The use of bulk density measurements as flowability indicators. Powder Technology 102, 151-165 (1999) compared to uncoated powders (Jallo et al., 2012 (referenced above)). As shown in FIG. 26a, Avicel® 105 attained a bulk density higher than Prosolv® 90, and nearly approaching that of Prosolv® 90 HD, which has the highest bulk density of the group. Considering that both Prosolv® 90 and Prosolv® 90 HD had larger (95 µm to 110 µm) and more spherical particles than Avicel® 105, such high bulk density of Avicel® 105 having average particle size of about 20 □m is unexpected. Improvement in bulk density upon dry coating Avicel® 105 with A200 make it possible to use in high speed direct compaction since it meets the bulk density requirement suggested by (Sun, 2010). (see dotted line in FIG. 26a)

Figure 26B:
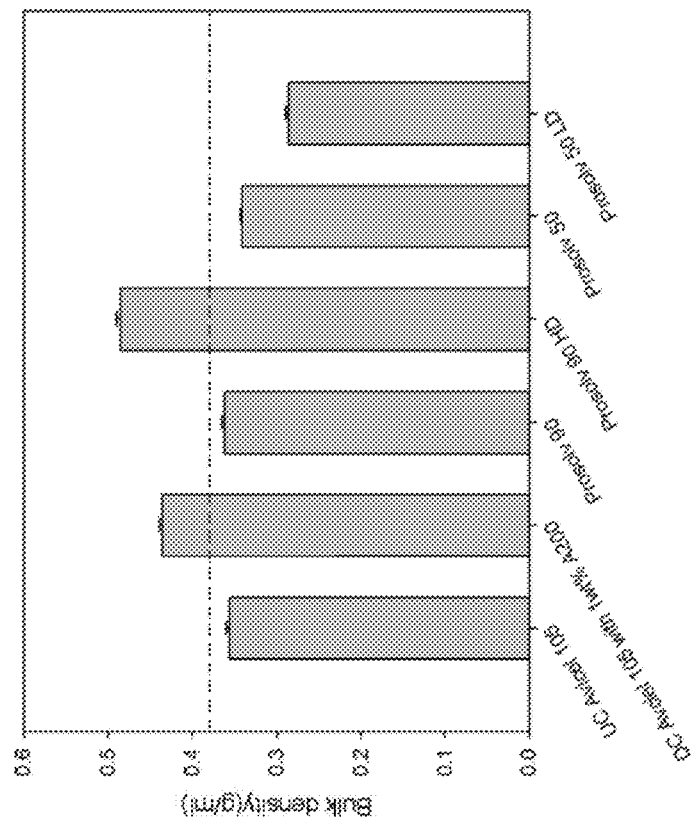

FIG. 26b depicts the flowability of as received and dry coated Avicel® 105 and compares that with the various Prosolv® excipients to examine how dry coated Avicel 105® fares. The FFC of uncoated Avicel® 105 is 2.53, which indicates that it is a very cohesive powder according to the classification of (Schulze, 2008 (referenced above)) The FFC of Avicel® 105 blended with 1 wt % A200 was found to increase to 3.8 (not shown), which was still in the cohesive flow range. However, the dry coated Avicel®105 with 1 wt % A200 showed FFC in free-flowing regime where FFC is in excess of 10, i.e., 21.9 as shown in FIG. 26b and Table 1. Thus, simply adding a glidant, e.g., A200 during normal blending is not sufficient to achieve the desired flowability. The improvement between blending and dry coating was expected based on the inter-particle adhesion models that indicate over an order of magnitude reduction in adhesion forces after dry coating (Chen et al. 2008; Yang et al. 2005 (both referenced above)) When compared with finer grades of Prosolv®, i.e., Prosolv® 50 and Prosolv® 50 LD, the dry coated Avicel® 105 exhibits better flowability even though it is finer than Prosolv® 50 grades.

Figure 27:
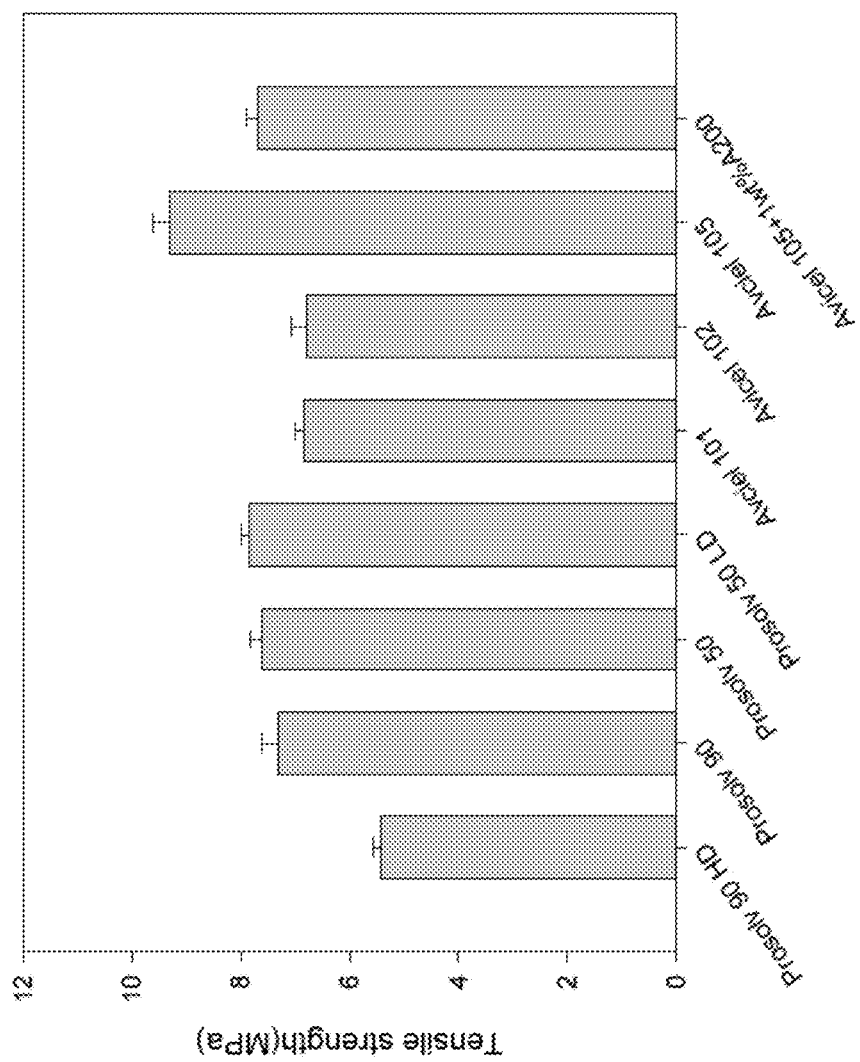
FIG. 27 is a bar graph of tensile strength for tablets made from uncoated or dry coated excipients in comparison to various grades of Prosolve®.

The tensile strength of the as received and dry coated Avicel® 105, other grades of Avicel®, and various grades of Prosolv® was determined in the same manner as described for prior examples. FIG. 27, which depicts the results of these tensile strength measurements, shows that the dry coated Avicel® 105 is comparable in tensile strength to the various grades of Prosolv® and coarser grades of Avicel®. Expectedly, there is a drop off in tensile strength in the dry coated Avicel® 105 in comparison to the as received Avicel® 105.

Example 16

Figure 28B:
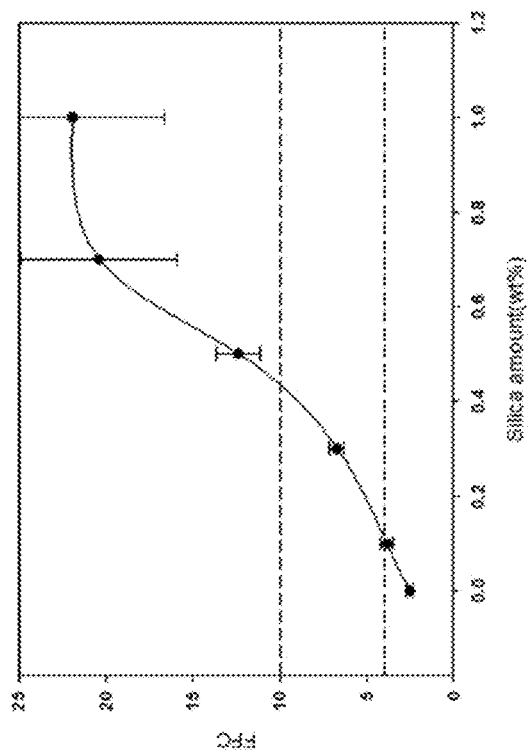
FIGS. 28a-c are, respectively, bulk density, FFC, and tensile strength as a function of guest material loading.
Figure 28A:
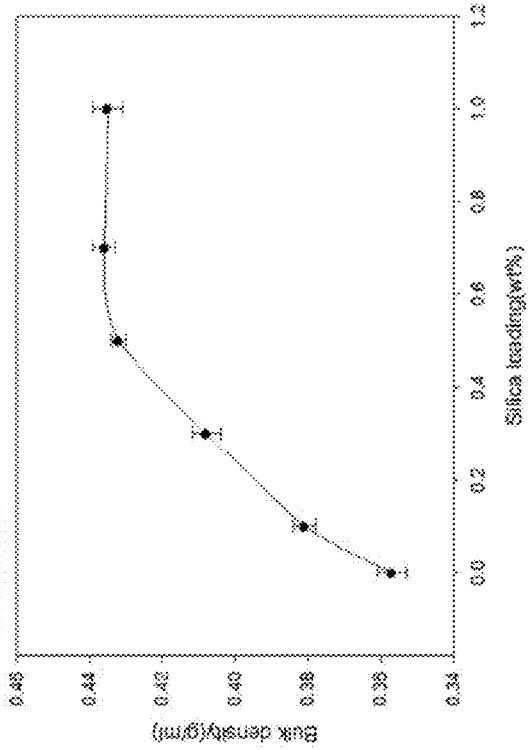
Figure 28C:
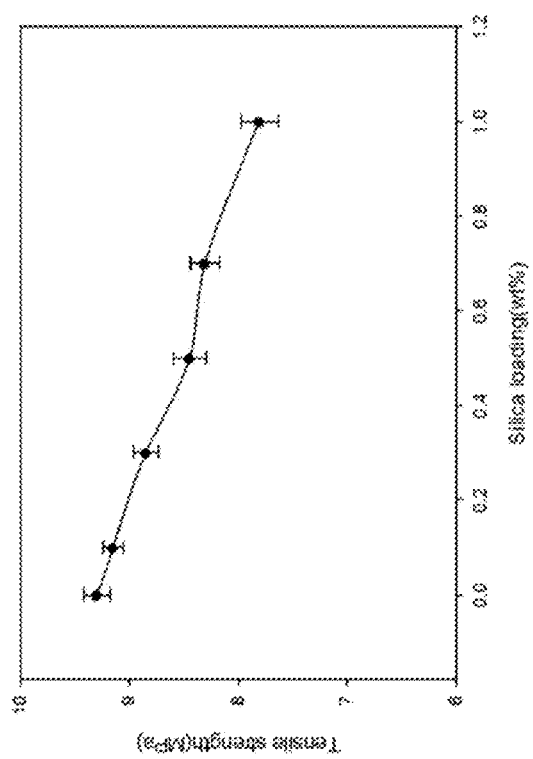

Example 16 determines effects of guest material amount on bulk density, flowability and tensile strength using dry coated Avicel® 105 at guest material (A200) amounts ranging from 0 wt % to 1 wt %. Unless otherwise noted, the preparation of these samples is the same as prior examples, except adjusting the amount of guest material. FIGS. 28a-c depict the results of Example 16. FIG. 28a shows that as the amount of A200 decreased from 1.0 wt % to about 0.5 wt %, the effect on the bulk density is minimal. Then, bulk density began to drop off more substantially after about 0.5 wt %. It was further confirmed by SEM (not shown) that A200 was generally well covered on the surface of Avicel® 105 at about 0.5 wt % A200. From theoretical calculations based on Eq. (10) and Eq. (11), the equivalent percentage surface area coverage at 0.5 wt % A200 is 96%.

$$Gwt\% = \frac{Nd^3\rho_d}{d^3\rho_D + Nd^3\rho_d} * 100 \quad (10)$$

$$N = \frac{4(D+d)^2}{d^2} \quad (11)$$

Since Avicel® 105 has an irregular shape, the assumptions the above SAC calculation (Yang et al., 2005 (referenced above)), overestimates the actual level of coating. However, the level of coating appears to be adequate to provide guest-guest contact as discussed in (Chen et al., 2008 (referenced above)), assuring high level of cohesion reduction. Overall, SEM (not shown) confirmed that surface area coverage decreased with decreasing amount of guest material.

FIG. 28b shows a similar trend for FFC as that for bulk density. FFC was above 10, and hence free flowing, for up to 0.5 wt % A200. At lower amounts of guest material, FFC dropped more substantially, similar to the behavior for bulk density.

FIG. 28c shows the corresponding behavior for tensile strength. Tensile strength decreased almost linearly with increasing guest material amounts. This trend was expected as the presence of the guest material decreases surface energy. These results showed that the loss of compaction at 0.7 wt % and 0.5 wt % A200 was only 12% and 9%, respectively, relative to 0 wt % A200. Considering the magnitude of flowability and bulk density enhancement at 0.5 wt % A200, 9% loss of tensile strength is a reasonable tradeoff.

Figure 29A:
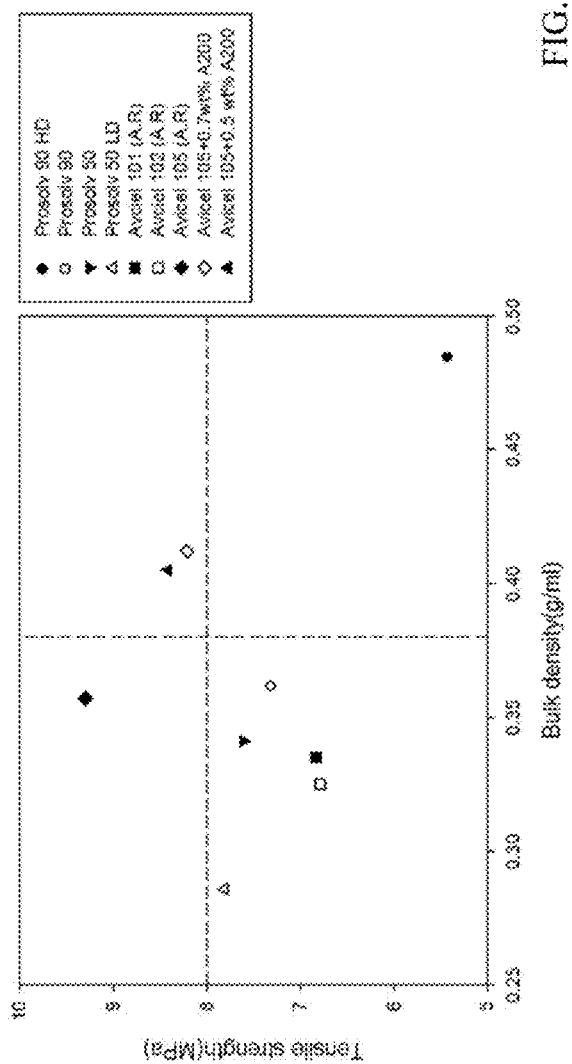
FIGS. 29a-b are, respectively, phase maps of tensile strength as a function of bulk density, and FFC as a function of tensile strength for uncoated and dry coated excipients in comparison to various grades of Prosolve®.
Figure 29B:
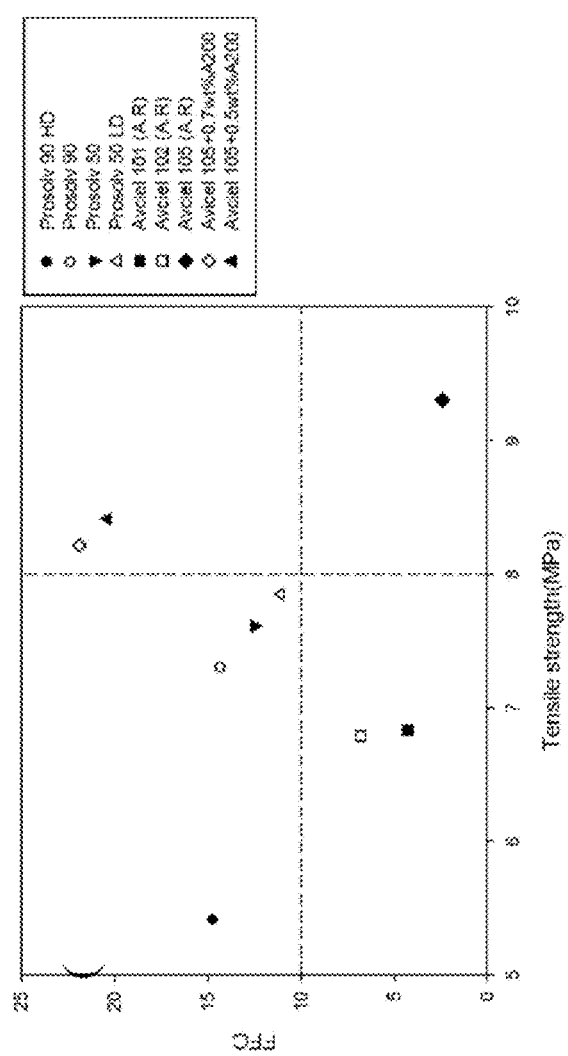

FIGS. 29a-b present tensile strength, bulk density, and flowability in the form of 2-D phase maps for several grades of as received Avicel®, Prosolv®, and some of the dry coated Avicel® 105 excipients of Example 16. In FIGS. 29a-b, vertical and horizontal dashed lines indicate ideal levels of respective properties for use as pharmaceutical excipients. As shown in FIG. 30a, amongst commercially available excipients, Avicel® 105 has the highest tensile strength but a relative low bulk density, Prosolv® 90 HD has the highest bulk density but lowest tensile strength, and Prosolv® 50 LD has a relative high tensile strength but the lowest bulk density. Avicel® 101, Avicel® 102, Prosolv® 50 and Prosolv® 90 have relatively average bulk density and tensile strength. As shown in FIG. 29b, Avicel® 105 shows the best compaction but worst flow, Prosolv® 90 HD has the best bulk density but worst compaction property. Avicel® 101 and Avicel® 102 have relatively low compaction properties and flowability. Prosolv® 50, Prosolv® 50 LD and Prosolv® 90 have a good flow property but relatively average compaction property. These results generally show that one excipient property was sacrificed in order to meet ideal conditions for another property. However, Avicel® 105 dry coated with either 0.5 wt % or 0.7 wt % A200 were able to satisfy all properties conditions.

Example 17

Figure 30:
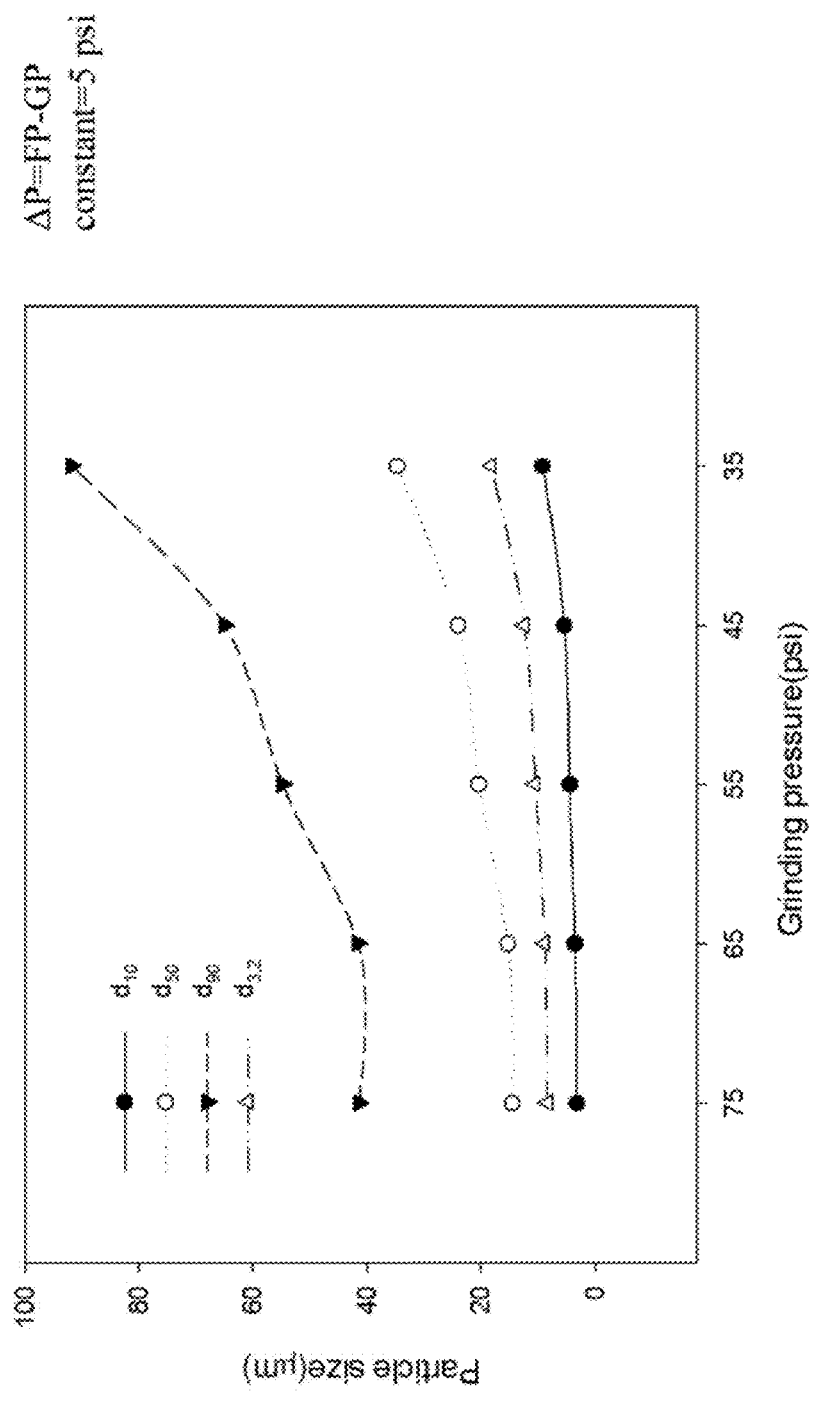
FIG. 30 is a plot of particle size as a function of grinding pressure for a micronization process.

Avicel 102® powder, having median size (d50) of about 122 microns was used as a starting material and was milled using the fluid energy mill (FEM) described here in. A guest material is not used in Example 17. Particle size distributions under different FEM operation conditions (see FIGS. 30-32 for respective operating conditions) were measured using the particle size analyzer described herein. The effect of grinding pressure, feeding pressure and feeding rate were systematic investigated. FIG. 30 shows the effect of grinding pressure at a constant pressure difference between grinding pressure and feeding pressure on particle size. As depicted in FIG. 30, the particle size decreases with increasing of grinding pressure (from 35 psi to 65 psi). The high grinding pressure increases the collisions among the particles which helps a lot for micronization during the milling process. After the grinding pressure reaches 65 psi, there is no effect on particle size distribution. It is because the residence time is too small for the high grinding pressure which leads to certain amount of particles are not grinded during the milling process.

Figure 31:
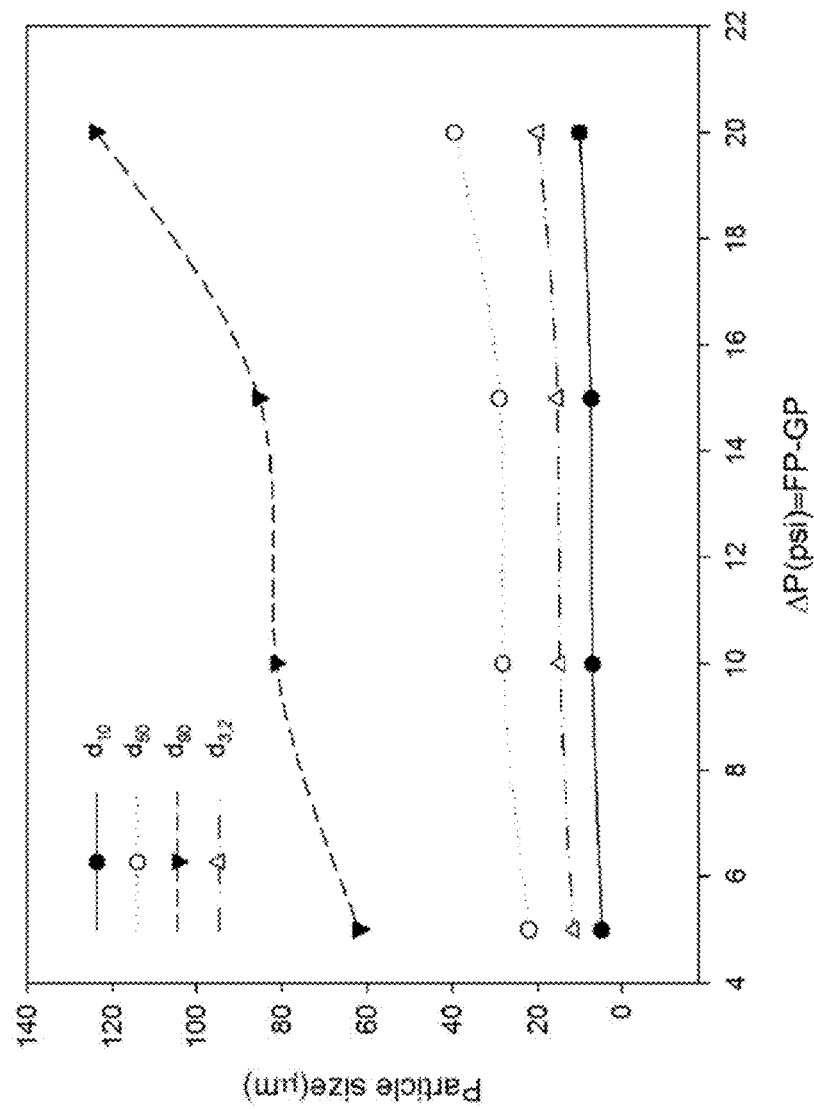
FIG. 31 is a plot of particle size as a function of change in pressure for a micronization process.

FIG. 31 shows the effect of grinding pressure at constant feed pressure and feed rate on particle size. As shown in FIG. 31, the particle size increases with increasing the difference between feeding pressure and grinding pressure. Since the maximum grinding pressure was controlled under 65 psi, the trend is consistent with previous discussion in FIG. 1.

Figure 32:
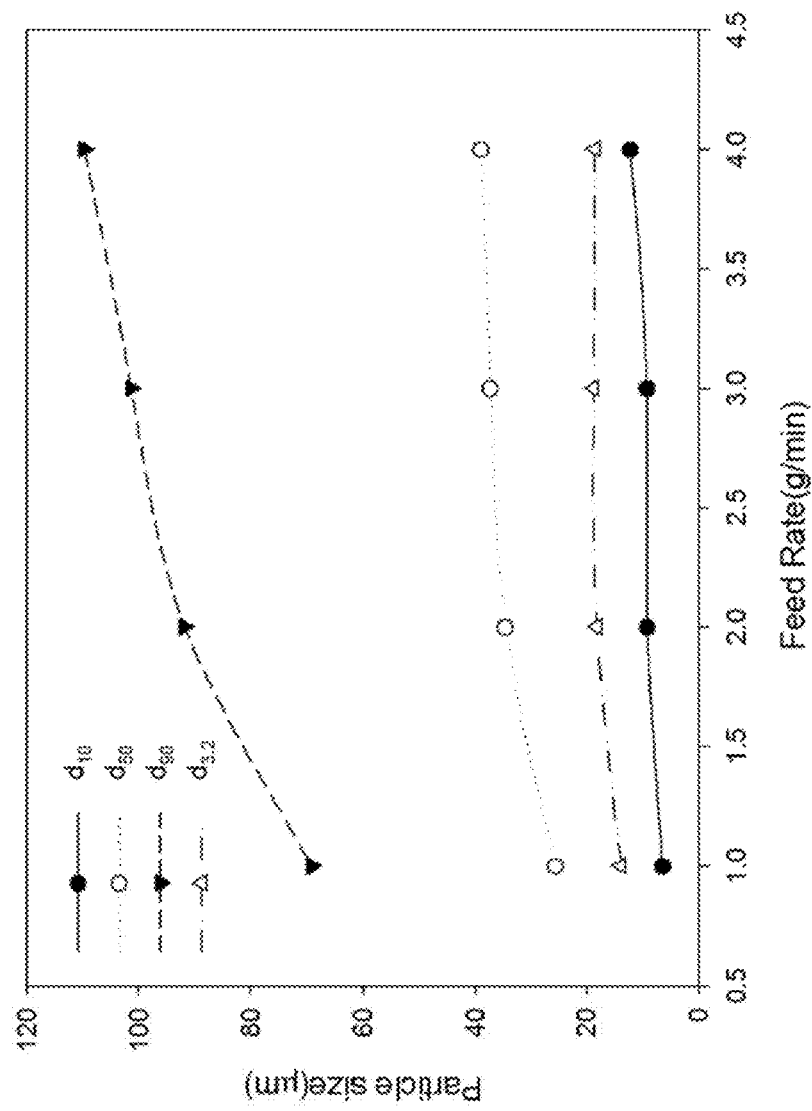
FIG. 32 is a plot of particle size as a function of feed rate for a micronization process.

FIG. 32 shows the effect of feed rate on particle size at a constant feed pressure and grinding pressure. The particle size decreases with increasing the feed rate as shown in FIG. 32. At high feed rate, the total collisions are higher than that of lower feed rate at a constant volume, however, the contribution of the effective collisions for micronization is lower than that of lower feed rate.

Example 18

Using the same host material as Example 17 and the conditions provided in Table 16, Examples 18.1 through 18.15 were made using simultaneous micronization and coating in the FEM. 20.37 μm, 25.54 μm, 31.77 μm, 34.67 μm, 39.11 μm) of particle size were select for bulk density, flowability and compaction study with R972P and A200 during simultaneous micronization and coating process using a fluid energy mill Their corresponding process conditions are described in the table below.

TABLE 16

| Example | Guest material (1 wt %) | Feed Rrate (g/min) | Feed Pressure (psi) | Grinding Pressure (psi) | d50 (μm) |
|---|---|---|---|---|---|
| 18.1 | — | 2 | 60 | 55 | 20.37 |
| 18.2 | R972P | | | | |

TABLE 16-continued

| Example | Guest material (1 wt %) | Feed Rrate (g/min) | Feed Pressure (psi) | Grinding Pressure (psi) | d50 (μm) |
|---|---|---|---|---|---|
| 18.3 | A200 | | | | |
| 18.4 | — | 1 | 40 | 35 | 25.54 |
| 18.5 | R972P | | | | |
| 18.6 | A200 | | | | |
| 18.7 | — | 2 | 40 | 35 | 31.77 |
| 18.8 | R972P | | | | |
| 18.9 | A200 | | | | |
| 18.10 | — | 4 | 50 | 45 | 34.67 |
| 18.11 | R972P | | | | |
| 18.12 | A200 | | | | |
| 18.13 | — | 4 | 40 | 35 | 39.11 |
| 18.14 | R972P | | | | |
| 18.15 | A200 | | | | |

Figure 33:
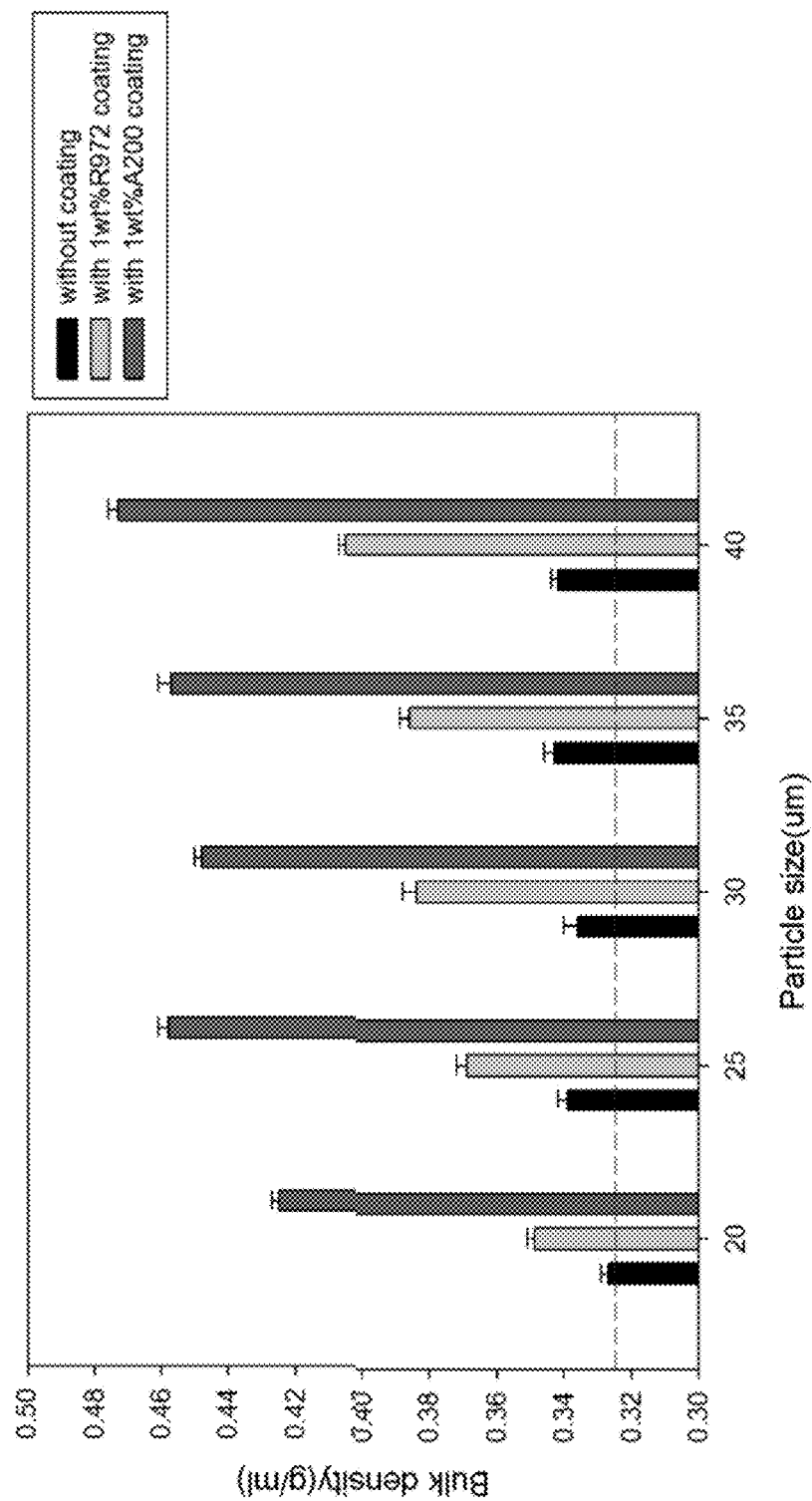
FIG. 33 is a bar graph of bulk density for uncoated and dry coated excipients made using a micronization process.

The effect of simultaneous micronization and coating on bulk density is shown in FIG. 33. The reference line (in FIG. 33) is as received Avicel® 102. As depicted in FIG. 33, the bulk density increases for each of example 18.1 through 18.15 after micronization without coating. However, there is significantly improvement in bulk density after simultaneous micronization and coating, i.e., Examples 18.2-18.3, 18.5-18.6. 18.8-18.9, 18.11-18.12, and 18.14-18.5. After simultaneous micronization and dry coating, nano-sized guest particles which were randomly distributed on the surface of the micronized host particles appear to have reduced roughness of the host particle surface based on SEM imaging (not shown). This observation was further confirmed by higher bulk density and flowability in the coated excipients compared to uncoated.

Figure 34:
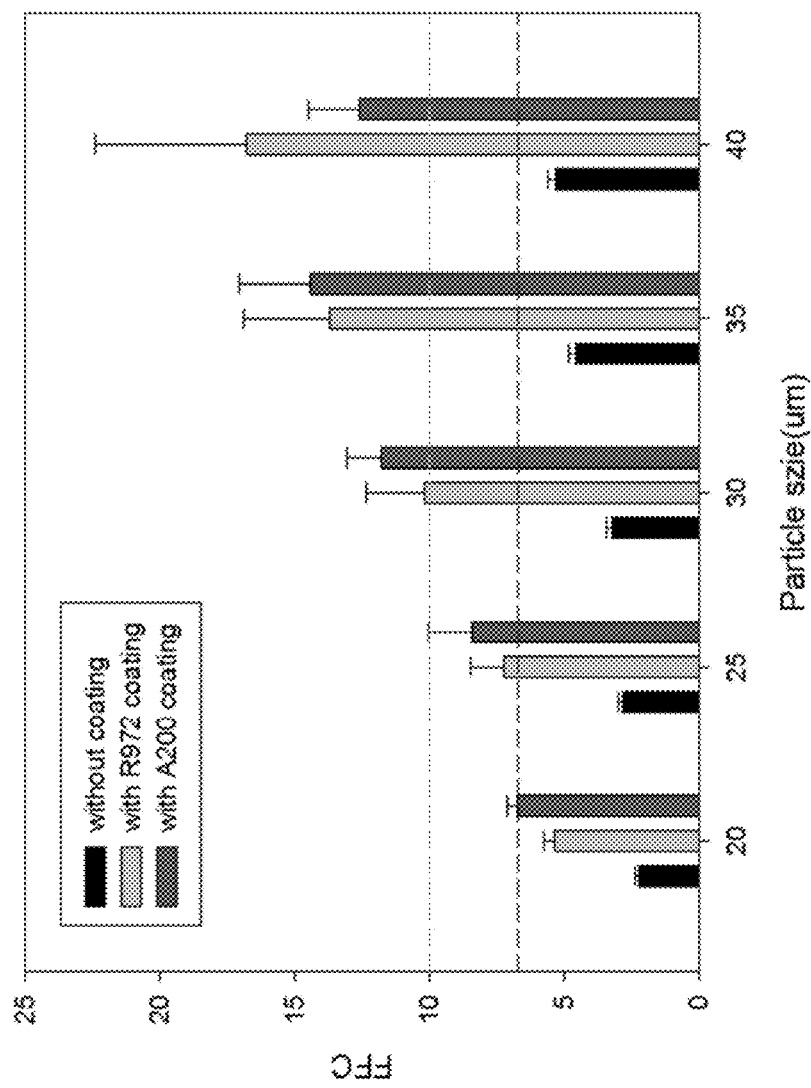
FIG. 34 is a bar graph of FFC for uncoated and dry coated excipients made using a micronization process.

The FFC of micronized uncoated powders are below 4 (FIG. 34) which indicates they are all cohesive powders, except the particles at size 39.11 μm (Example 18.13). However, FFC of micronized and coated powders have a significant improvement for all particle sizes compared to uncoated. Moreover, almost all size groups have higher flow properties than that of as received Avicel® 102 (first reference line between FFC of 5 to 10). A second reference line at the boundary of the free flow condition of FFC>10 is also provided in FIG. 34. Such drastic improvement is expected based on the inter-particle adhesion models that indicate over an order of magnitude reduction in adhesion forces after dry coating (Chen et al., 2008; Yang et al., 2005 (both referenced above)).

Example 19

Figure 35:
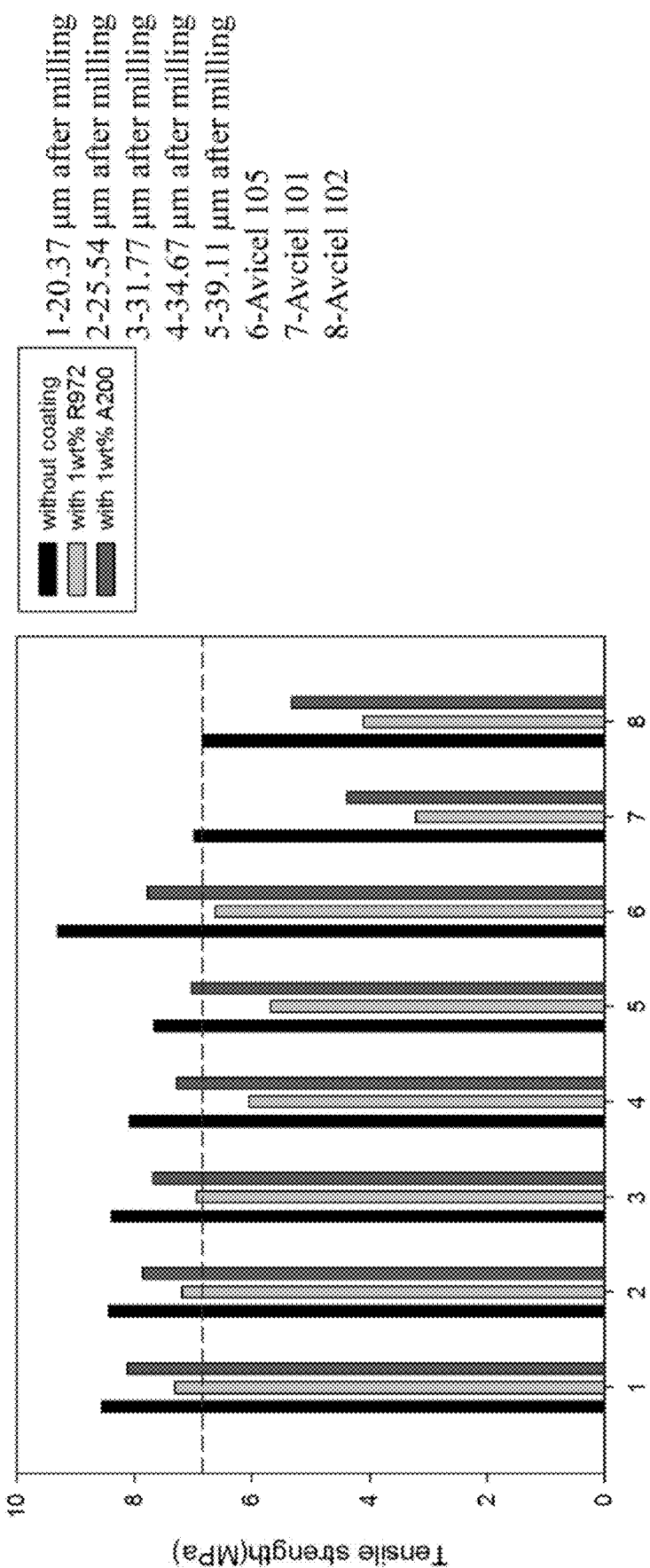
FIG. 35 is a bar graph of tensile strength for uncoated and dry coated excipients made using a micronization process in comparison to uncoated and dry coated excipients made using a different process or as received.
Figure 36:
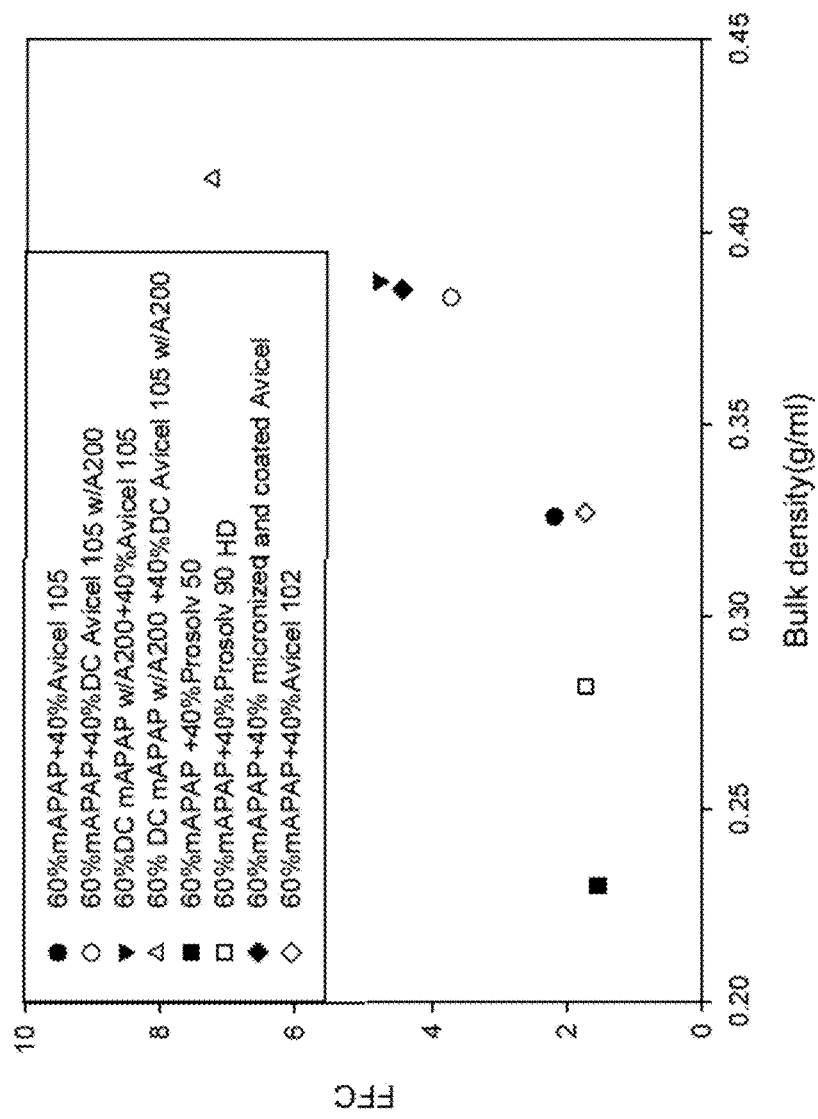
FIG. 36 is a phase map of FFC as a function of bulk density for blends of cohesive and non-cohesive API and uncoated and dry coated excipients.
Figure 37:
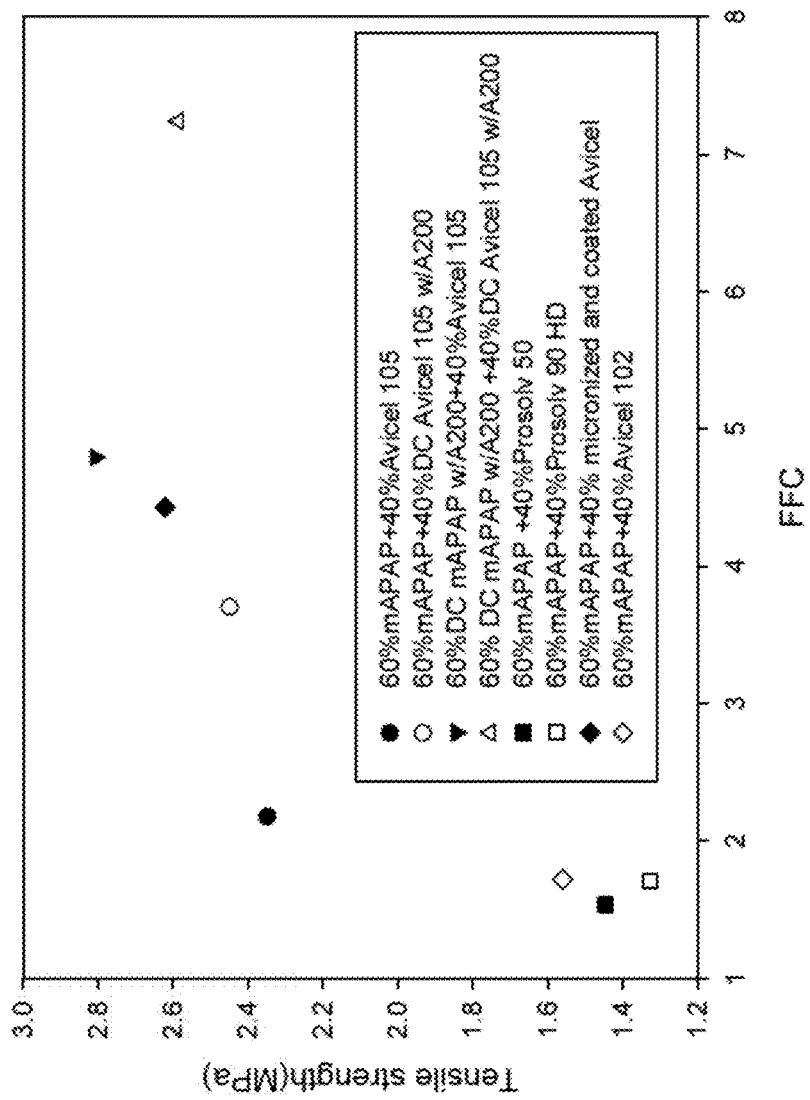
FIG. 37 is a phase map of tensile strength as a function of FFC for blends of cohesive and non-cohesive API and uncoated and dry coated excipients.
Figure 38:
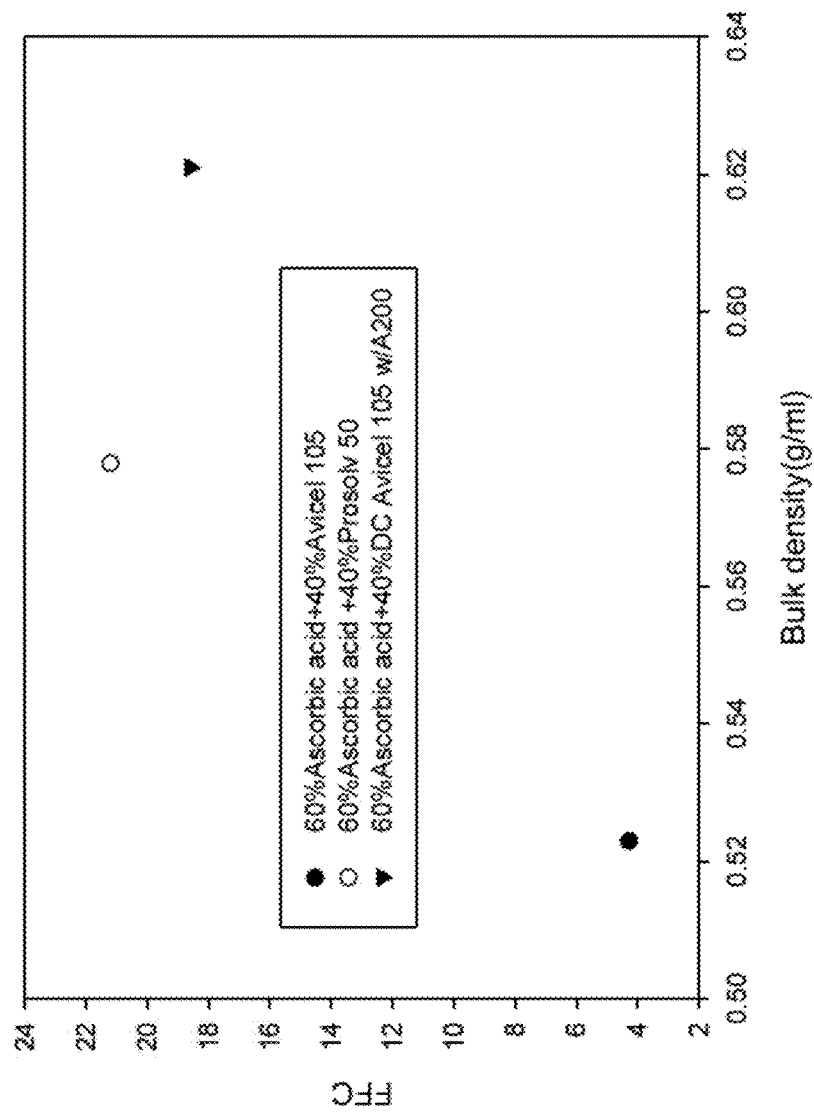
FIG. 38 is a phase map of FFC as a function of bulk density for blends of a non-cohesive API and uncoated and dry coated excipients.
Figure 39:
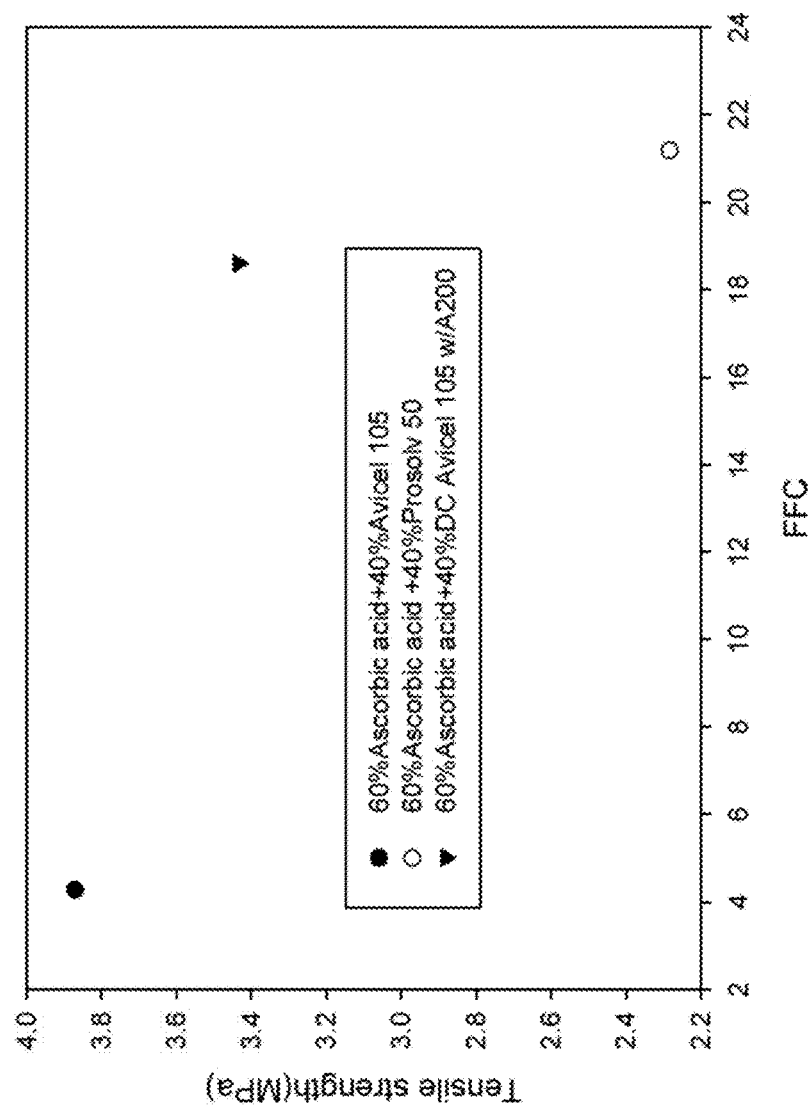
FIG. 39 is a phase map of tensile strength as a function of FFC for blends of a non-cohesive API and uncoated and dry coated excipients.

Example 19 studies compaction properties of the materials in Example 18. Compacted tablets of each excipient are made by methods discussed herein, i.e., tablets containing about 500 mg powder sample and 0.5" inner diameter die, were compressed at about 114 MPa. Results are shown in FIG. 35. The tensile strength is increasing with the decreasing the particle size of the micronized Avicel® 102. A reference line is provided in FIG. 35 for the tensile strength of as received Avicel® 102 is provided in FIG. 36. Non-micronized, coated and uncoated examples of Avicel® 101, 102, and 105 are also provided in FIG. 35. The coating of these non-micronized Avicel® grades is done using LabRAM at the standard conditions discussed in the methods section. And this phenomenon can be explained by BABS model (Sun 2011), the bonding strength does not change since it is the material property, however, the bonding area is increasing with decreasing the particle size. The overall effect on micronization alone leads to increase the tensile strength of powders. On the other hand, the particles intend to be cohesive when the size of the powders is less than 50 μm. However, the combination of simultaneous micronization and dry coating can overcome the negative effect on powder flowability during micronization and still attain the advantages of dry coating on improving the bulk density and flowability as discussed in previous examples. As depicted in FIG. 35, the simultaneous micronization and dry coating by using 1 wt % A200 has a better compaction results compared with as received Avicel® 102.

The results show that the surface engineered excipients not only improved the bulk density and flowability of the processed excipients, but also enhanced the compaction properties of the prepared tablets compared with as received materials. Moreover, the large range of particle size of the surface engineered excipient can meet the critical properties for direct compaction especially for fine APIs to avoid segregation. In addition, the continuous process of fluid energy mill can be easily scaled up in industry.

Example 20

TABLE 16

| Example | API | API (wt %) | Excipient | Excipient (wt %) |
|---|---|---|---|---|
| 20.1 | mAPAP | 60 | Avicel ® 105 | 40 |
| 20.2 | mAPAP | 60 | Avicel ® 105 + 1 wt % A200 | 40 |
| 20.3 | mAPAP + 1 wt % A200 | 60 | Avicel ® 105 | 40 |
| 20.4 | mAPAP + 1 wt % A200 | 60 | Avicel ® 105 + 1 wt % A200 | 40 |
| 20.5 | mAPAP | 60 | Prosolv ® 50 | 40 |
| 20.6 | mAPAP | 60 | Prosolv ® 90 HD | 40 |
| 20.7 | mAPAP | 60 | Ex 18.9 | 40 |
| 20.8 | mAPAP | 60 | Avicel ® 102 | 40 |
| 20.9 | Ascorbic acid | 60 | Avicel ® 105 | 40 |
| 20.10 | Ascorbic acid | 60 | Prosolv ® 50 | 40 |
| 20.11 | Ascorbic acid | 60 | Avicel ® 105 + 1 wt % A200 | 40 |

FIGS. 36 through 39 depict measurements of bulk density, FFC and tensile strength for the binary blends of Examples 20.1 through 20.11 of Table 16. In these examples, mAPAP (as-received) is considered to be a cohesive API, as indicated by its FFC of 1.93 and bulk density of 0.206 g/mL. In contrast, after dry coating mAPAP with 1 wt % silica A200 using LabRAM (at standard conditions described in method section), the dry coated mAPAP becomes "not cohesive", as indicated by its FFC of 3.93 and bulk density of 0.416 g/mL. In addition, coarse grade Ascorbic Acid (Medisca, Inc. Plattsburgh, N.Y., USA) was also used (D50 of 217 microns), and it is also not cohesive because of its FFC of 4.67 and bulk density of 0.896 g/mL. Improvement in bulk density and FFC was obtained when at least one of the API or excipient was dry coated. A comparison of coated API (Example 20.3) compared to uncoated API (Example 20.1) showed an improvement in all three properties. (see FIGS. 36-37) The further addition of a coated excipient (Example 20.4) demonstrated a further improvement in bulk density and FFC compared to only a coated excipient (Example 20.3), but a reduction in tensile strength. Thus, the further inclusion of the coated excipient reduced the tensile strength in the presence of a coated API, e.g., a non-cohesive API. In contrast, the addition of a coated excipient in the presence of a non-coated API, hence cohesive, (Example 20.2) showed improvement in all three properties, including tensile strength compared to a non-coated excipient (Example 20.1). Considering that the coating of the excipient typically reduces tensile strength (e.g., as seen in the comparison of Examples 20.3 and 20.4), the results of improved tensile strength between example 20.2 in comparison to example 20.1 is not expected. More surprisingly, when the API is not dry coated, hence is cohesive, this improvement is even more pronounced in example 20.7, using the dry coated and micronized MCC based novel excipient which is larger than Avicel® 105 in size leads to better tablet strength than using dry coated Avicel® 105 with uncoated API. The results for ascorbic acid as API (non-cohesive in its as received state, FIG. 38-39) show that using dry coated Avicel 105® (Example 20.11) indeed reduces the tablet strength in comparison to as-received Avicel 105® (Example 20.9).

Example 20 illustrates unexpected outcomes of blends of cohesive APIs and dry coated fine excipients. First, tablets made from blends of non-cohesive API (dry coated mAPAP and uncoated ascorbic acid) and dry coated fine excipient (dry coated Avicel 105®) resulted in reduced tablet strength compared to using as-received Avicel 105®. In contrast, when a blend used a cohesive API (mAPAP) in combination with a dry coated fine excipient (dry coated Avicel 105®) tablet strength improved compared to a blend using as-received Avicel 105®. This increase in tablet strength along with the benefit of imparting better flow (FFC) and packing density to blends at high API loading was an unexpected feature of a blend of a cohesive API and a fine dry coated excipient. Second, the use of dry coated and micronized MCC also shows enhanced tablet strength, FFC, and bulk density in high drug loaded cohesive API blends. This outcome suggests that fine dry coated API in size smaller size range, without being too fine is beneficial in blends. Third, dry coated fine excipient (either Avicel 105® or micronized MCC) in a API blends at high drug loading clearly outperforms similar blends made using engineered excipients like Prosolv® 50 or Prosolv® 90 HD, in terms of flow (FFC), bulk density, as well as strength of tablets formed using those blends. This is a remarkable and surprising outcome considering those excipients have been designed to provide improved flow, bulk density and tablet strength. It is important to note that such outcome is independent of the type of API used (cohesive or non-cohesive), demonstrating that a better excipient is that which is finer (under about 40 microns) and has good flow and bulk density.

The results shown here demonstrate that a dry coated excipient in size range of about 20 micron to about 40 micron made from good tablet forming materials like MCC has very desirable properties for use in high drug loaded API blends. Such excipients are even more useful for forming blends of fine, cohesive APIs. Using such excipient is beneficial in pharmaceutical manufacturing because it allows eliminating or minimizing the need for wet granulation for the purpose of tablet making even at higher drug loading. Further, such excipients are expected to allow wider range of cohesive API formulations that can be used in making tablets via high-speed direct compression machines, and would not require dry granulation such as roller compaction Eliminating any form of granulation greatly reduces complexity and cost in pharmaceutical tablet manufacturing and will find greater use in emerging trend of continuous tablet manufacturing via high-speed direct compression.

While exemplary embodiments have been described herein, it is expressly noted that these embodiments should not be construed as limiting, but rather that additions and modifications to what is expressly described herein also are included within the scope of the invention. For example, the systems and processes are applicable to other excipients. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A pharmaceutical blend, consisting essentially of:
a non-coated cohesive active pharmaceutical ingredient (API), wherein the cohesive API is present in an amount ranging from about 30 wt % to about 99 wt % to form a high drug loading;
a dry coated pharmaceutical excipient forming a pharmaceutical blend with the non-coated cohesive API, wherein the pharmaceutical excipient is present in an amount of about 1 wt % to 70 wt %, based on the total weight of the pharmaceutical blend,
the dry coated pharmaceutical excipient includes a core, and a shell surrounding the core of the excipient in a manner as not to cover the entire core; and a dry coating is only disposed on the excipient and not on the API;
wherein the pharmaceutical excipient has a particle size in a range of about 20 microns to about 40 microns for eliminating wet granulation at the high drug loading, and the shell includes a plurality of discrete particles having an average particle size ranging from about 5 nanometers to 35 nanometers disposed on a surface of the core for improvement in bulk density and flowability of the pharmaceutical blend;
the non-coated cohesive API has a bulk density ranging from about 0.05 g/mL to 0.40 g/mL and a flow function coefficient (FFC) ranging from about 0.10 to 3.5 defining a poor flow and a poor bulk density for the non-coated cohesive API;
the blend has a bulk density above 0.41 g/mL and a flow function coefficient (FFC) ranging from about 3.7 to 8.0; and
wherein addition of the coated excipient in presence of the non-coated API, showed improvement in bulk density, FCC, and tensile strength as compared to the blend with a non-coated excipient.

2. The pharmaceutical blend of claim 1, wherein the core is a compound selected from the group consisting of microcrystalline cellulose (MCC), pre-gelatinized starch, lactose, mannitol, dibasic calcium phosphate dehydrate, calcium carbonate, croscarmellose sodium, confectioner sugar, and any combination thereof.

3. The pharmaceutical blend of claim 1, wherein the shell is a compound selected from the group consisting of glidants, lubricants, surfactants, silica, titania, talc, magnesium stearate, steric acid, sodium dodecyl sulfate, and any combination thereof.

4. The pharmaceutical blend of claim 3, wherein the silica is a hydrophilic silica or a functionalized hydrophobic silica, wherein the hydrophilic silica has a specific surface area ranging from 175 $m^2$/g to 225 $m^2$/g, and wherein the functionalized hydrophobic silica has a specific surface area ranging from 90 $m^2$/g to 130 $m^2$/g.

5. The pharmaceutical blend of claim 1, wherein the non-coated cohesive API is hydrophilic or hydrophobic.

6. The pharmaceutical blend of claim 1, wherein the shell is present in an amount ranging from about 0.01 wt % to about 1.95 wt %, based on the weight of the core.

7. The pharmaceutical blend of claim 1, wherein the shell is present in an amount ranging from about 0.05 wt % to about 1.0 wt %, based on the weight of the core.

8. The pharmaceutical blend of claim 1, wherein the non-coated cohesive API is present in an amount of about 99 wt %, based on the total weight of the pharmaceutical blend.

9. The pharmaceutical blend of claim 1, wherein the non-coated cohesive API is present in an amount of about 60 wt %, based on the total weight of the pharmaceutical blend.

10. The pharmaceutical blend of claim 1, wherein the bulk density of the dry coated pharmaceutical excipient ranges from about 0.3 g/mL to about 0.7 g/mL.

11. The pharmaceutical blend of claim 1, wherein a flow function coefficient (FFC) of the coated pharmaceutical excipient ranges from 3 to 30.

12. The pharmaceutical blend of claim 1, wherein the bulk density of the pharmaceutical blend ranges from about 0.41 g/mL to about 0.99 g/mL.

13. The pharmaceutical blend of claim 1, wherein a flow function coefficient (FFC) or flowability of the pharmaceutical blend is about 8.

14. The pharmaceutical blend of claim 1, wherein the shell is present in an amount of about 0.01 wt % to about 1 wt %, based on the total weight of the core.

15. The pharmaceutical blend of claim 14, wherein the plurality of discrete particles is selected from a group consisting of a dry coating nano-silica, a hydrophobic fine additive, a hydrophilic fine additive, and any combination thereof.

16. The pharmaceutical blend of claim 1, wherein the core is a microcrystalline cellulose (MCC).

17. A pharmaceutical blend of claim 16, wherein a pharmaceutical blend with the non-coated cohesive API is a tablet formed by direct compression and the tablet has a porosity ranging from about 0.05 to about 0.35 and a tensile strength ranging from about 1 MPa to about 10 MPa.

18. A pharmaceutical blend of claim 14, wherein the pharmaceutical blend with the non-coated cohesive API is a tablet formed by direct compression and the tablet has a porosity ranging from about 0.05 to about 0.35 and a tensile strength ranging from about 1 MPa to about 10 MPa.

19. The pharmaceutical blend of claim 1, wherein the pharmaceutical blend with the non-coated cohesive API is a tablet formed by direct compression and the tablet has a porosity ranging from about 0.05 to about 0.35 and a tensile strength ranging from about 1 MPa to about 10 MPa.

20. The pharmaceutical blend of claim 1, wherein the pharmaceutical blend with the non-coated cohesive API has a bulk density of about 0.411 g/ml and a FFC of about 7.87 for improved flow and bulk density as compared to the blend with a coated API and a non-coated excipient.

21. The pharmaceutical blend of claim 1, wherein the pharmaceutical blend with the non-coated cohesive API is a tablet formed by direct compression without additional free-flowing excipients, and no wet granulation.

22. The pharmaceutical blend of claim 1, wherein the pharmaceutical blend with the non-coated cohesive API is a tablet formed by direct compression with dry granulation.

* * * * *